(12) United States Patent
Nishiguchi et al.

(10) Patent No.: US 7,557,148 B2
(45) Date of Patent: Jul. 7, 2009

(54) CYCLIC CARBOXYLIC ACID COMPOUND AND USE THEREOF

(75) Inventors: Takahiro Nishiguchi, Ohtake (JP); Naoya Nakamura, Ohtake (JP); Makoto Tsuboi, Ohtake (JP)

(73) Assignee: Chugoku Marine Paints, Ltd., Ohtake-shi (JP)

( * ) Notice: Subject to any disclaimer, the term of this patent is extended or adjusted under 35 U.S.C. 154(b) by 209 days.

(21) Appl. No.: 10/581,039

(22) PCT Filed: Nov. 26, 2004

(86) PCT No.: PCT/JP2004/017624

§ 371 (c)(1),
(2), (4) Date: Jan. 9, 2009

(87) PCT Pub. No.: WO2005/051884

PCT Pub. Date: Jun. 9, 2005

(65) Prior Publication Data

US 2007/0105976 A1    May 10, 2007

(30) Foreign Application Priority Data

Nov. 27, 2003    (JP) .............................. 2003-397921

(51) Int. Cl.
*C07C 62/30* (2006.01)
*C09D 5/16* (2006.01)
(52) U.S. Cl. .................. 523/122; 524/413; 562/510
(58) Field of Classification Search ................ 523/122; 524/413; 562/510
See application file for complete search history.

(56) References Cited

U.S. PATENT DOCUMENTS

| 2,403,038 | A |   | 7/1946  | Aelony |
| 3,047,433 | A |   | 7/1962  | Bavley |
| 3,929,895 | A | * | 12/1975 | Hall ............................ 568/377 |
| 3,981,924 | A | * | 9/1976  | Hall ............................ 568/446 |
| 4,177,170 | A | * | 12/1979 | Cookson et al. ............. 512/136 |
| 4,374,123 | A | * | 2/1983  | Luccarelli et al. ............. 424/49 |
| 6,303,701 | B1 |  | 10/2001 | Isozaki et al. |
| 2003/0158292 | A1 | | 8/2003 | Masuoka et al. |

FOREIGN PATENT DOCUMENTS

| EP | 0 582 489 A1 | 2/2004 |
| GB | 896 039 | 5/1962 |
| JP | 54 103846 | 8/1979 |
| JP | 62 89778 | 4/1987 |
| JP | 8-209005 | 8/1996 |
| JP | 2001-288398 | 10/2001 |
| JP | 2001 323208 | 11/2001 |
| JP | 2003 183351 | 7/2003 |
| JP | 2003 183567 | 7/2003 |
| JP | 2005-15531 | 1/2005 |
| JP | 3914437 | 2/2007 |
| SU | 466210 | 2/1976 |
| TW | 200406473 | 5/2004 |
| TW | 1225884 | 1/2005 |

OTHER PUBLICATIONS

Chemical Abstracts Service, AN 1972:4021, XP-002444512, Matsubara, et al. (1971).
Chemical Abstracts Service, AN 1980:75973, XP-002444513, JP 54 103845 (1979).
Chemical Abstracts Service, AN 1972:153947, XP-002444514, Matsubara, et al. (1971).
Database Crossfire Beilstein, Beilstein Registry No. 21099008, XP 002444515, Patyk et al. (1976).
Database Crossfire Beilstein, Beilstein Registry No. 4865699, XP-002444516, Yamada, et al. (1993).
G. Ohloff, Justus Liebigs Annalen Der Chemie, vol. 606, pp. 100-123, XP008081843 (1957).
Chemical Abstracts Services, AN 1960:56119, XP-002444517, Vil 'Chinskaya, et al. (1959).
Database Crossfire Beilstein, Beilstein Registry No. 2465317, XP-002444518, Matsubara, et al. (1972).
Database Crossfire Beilstein, Beilstein Registry No. 6700878, XP-002444519, Joseph, et al. (1967).
Chemical Abstract Services, AN 1999:77204, XP002444520, Srikrishan, et al. (1999).
Chemical Abstract Service, AN 1996:247660, XP-00244452, Lamotkin, et al. (1995).
Chemical Abstracts Services, AN 1987:102591, XP-002444522, EX 541 929 a1 (1986).

* cited by examiner

*Primary Examiner*—Kriellion A Sanders
(74) *Attorney, Agent, or Firm*—Oblon, Spivak, McClelland, Maier & Neustadt, P.C.

(57) ABSTRACT

A novel cyclic carboxylic acid formed by the addition reaction of an unsaturated carboxylic acid with a conjugated diene compound and a metal salt thereof are disclosed. A compounding agent (A) for an antifouling paint comprising one or more substances selected from the novel cyclic carboxylic acid, a derivative of the cyclic carboxylic acid (except a metal salt), a metal salt of the cyclic carboxylic acid and a metal salt of a derivative of the cyclic carboxylic acid, and an antifouling paint composition comprising the compounding agent (A) and a copolymer (B) for a self-polishing type antifouling paint are also disclosed. The antifouling paint composition can form an antifouling coating film which is a small burden to the environment, is uniformly eroded at a given rate, is capable of maintaining excellent antifouling performance for a long period of time and is applicable to ships or the like used in the highly fouling sea area.

50 Claims, 12 Drawing Sheets

Fig. 1  IR spectrum of AD-1

Fig. 2   IR spectrum of AD-2

Fig. 4 MS spectrum of AD-3

Fig. 5  IR spectrum of AD-4

Fig. 7  MS spectrum of AD-5 (compound A-3)

Fig. 8  IR spectrum of AD-6

Fig. 9   IR spectrum of AD-7

Fig. 10 MS spectrum of AD-7

Fig. 11   IR spectrum of AD-8

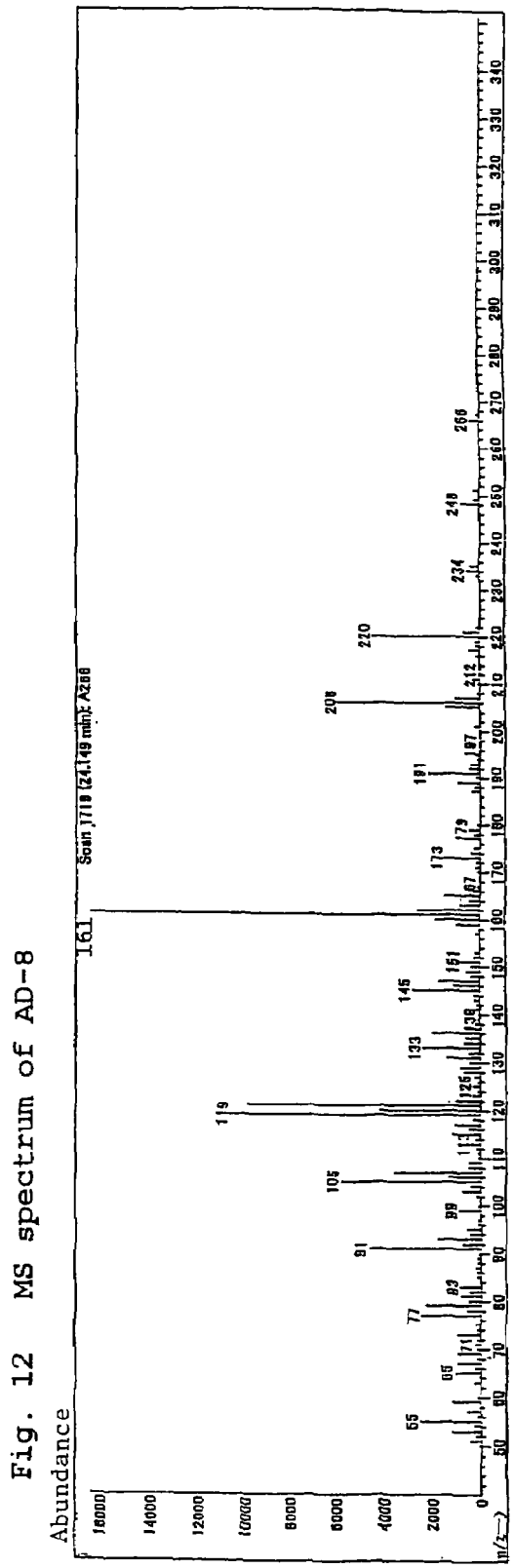
Fig. 12　MS spectrum of AD-8

CYCLIC CARBOXYLIC ACID COMPOUND AND USE THEREOF

TECHNICAL FIELD

The present invention relates to a novel cycloalkenylcarboxylic acid, a novel bicycloalkenylcarboxylic acid, derivatives thereof, a compounding agent for antifouling paint which comprises said acid or derivative, an antifouling paint composition, an antifouling coating film, a ship, an underwater structure, a fishing tackle or a fishing net coated with the antifouling coating film, and an antifouling method for them.

More particularly, the present invention relates to a novel cycloalkenylcarboxylic acid, a novel bicycloalkenylcarboxylic acid, derivatives thereof, a compounding agent for antifouling paint which comprises said acid or derivative, an antifouling paint composition having excellent storage stability and capable of forming an antifouling coating film which is a small burden to the environment, is uniformly eroded at a given rate over a long period of time, can maintain excellent antifouling performance for a long period of time, exhibits excellent antifouling performance in the highly fouling sea area or in the static environment and has an excellent balance of these properties, an antifouling coating film, a ship, an underwater structure, a fishing tackle or a fishing net coated with the antifouling coating film, and an antifouling method for them.

BACKGROUND ART

Bottoms of ships, underwater structures, fishing nets, etc. are exposed to water for a long period of time, so that various aquatic organisms, e.g., animals such as oysters, mussels and barnacles, and plants such as seaweeds and bacteria, are liable to adhere to their surfaces and propagate thereon. If such animals and plants adhere and propagate, not only appearances of the ship-bottoms, underwater structures, fishing nets, etc. are deteriorated but also functions thereof are impaired.

Particularly in the case where such aquatic organisms adhere and propagate on the bottom of ship, surface roughness of the whole ship is increased to sometimes induce lowering of ship velocity and increase of fuel consumption. Further, in the case where bacteria, slime (sludge substances) or larger organisms adhere and propagate on the surfaces of underwater structures such as steel structures, the structures may be corroded or the anti-corrosion coating films on the underwater structures may be damaged, that is, there is a fear that the strength, functions and lifetime of the underwater structures are markedly lowered. For removing such aquatic organisms from the underwater structures, much labor and working time are required.

In order to prevent such damages, coating of the base materials of ships, underwater structures, etc. with antifouling paints has been heretofore carried out. The existing antifouling mechanisms of the antifouling paints are broadly divided into a mechanism of extraction type (diffusion type) wherein an antifouling agent is extracted from a coating film and a mechanism of a self-polishing type wherein a surface of a coating film is renewed to bring a fresh antifouling agent into contact with seawater. The extraction type has disadvantages of increase in surface roughness and a short period of antifouling time.

Therefore, the antifouling paints of self-polishing type are preferably employed for the base materials of ships, underwater structures, etc. which require long-term antifouling property. In case of the antifouling paints of self-polishing type, the surface of the resulting coating film is dissolved little by little, so that the coating film surface can be maintained smooth. Moreover, there is an advantage that by controlling the dissolution rate of the coating film, the elution rate of the antifouling agent can be controlled over a long period of time, and thereby excellent antifouling property can be maintained for a long period of time.

As such an antifouling paint of self-polishing type, an antifouling paint composition comprising rosin which is collected from natural pine and a synthetic resin which serves to reinforce strength of a rosin-based coating film is known.

The rosin is a natural compound containing abietic acid and its isomer as main ingredients, and it is known that the rosin is slightly soluble in seawater. Such rosin is widely employed as a resin for an antifouling paint.

For example, in Japanese Patent Laid-Open Publication No. 30071/1998 (patent document 1), a paint composition containing, as essential ingredients, one or more compounds selected from rosin-based compounds such as rosin, rosin derivatives and rosin metal salts, an organic silyl ester group-containing polymer and an antifouling agent is disclosed. In this publication, it is described that a coating film made of the paint composition does not cause formation of a residue layer on the surface of the film even after long-term immersion, is free from defects such as cracking and peeling, exerts marine organism adhesion-preventing performance over a long period of time and is excellent in recoating property and marine organism adhesion-preventing performance in the outfit time.

However, the rosin-based compounds are derived from natural substances, so that there are a fear of unstable supply and a fear of exhaustion of resources in the future. Moreover, there is a problem that the rosin-based compounds have variability in qualities and composition attributable to growing district, type of tree, purification conditions, storage conditions, etc., so that it is difficult to obtain antifouling paint compositions of excellent and uniform qualities.

Under such circumstances as described above, the present inventors have earnestly studied for the purpose of developing a novel antifouling paint composition capable of forming an antifouling coating film having proper solubility and long-term antifouling property.

By the way, in the development of an antifouling paint composition, the following problems should be taken into consideration.

First, there has been much more desired than before an antifouling paint composition capable of forming a coating film which can exert high antifouling performance over a long period of time even in the highly fouling environment, because in recent years environmental pollution is getting worse and contamination of seawater near the land has become terrible, and for example, ships must stay in such a terribly contaminated sea area for a long period of time when they stop at ports for charging cargos or during the outfit time (period of time for building an interior of a ship on the sea after building of outside plating of the ship in the dock).

Further, the antifouling paint is sometimes stored for a long period of time after it is put on the market, and also in such a case, it is required that property change and deterioration of the paint do not occur.

The present inventors have earnestly studied aiming at development of a paint composition satisfying all of the above requirements, and as a result, they have found that a specific cyclic carboxylic acid formed by the addition reaction of a specific unsaturated carboxylic acid with a specific conjugated diene compound and a metal salt thereof are novel compounds and that one or more compounds (A) selected from the novel cyclic carboxylic acid, the metal salt thereof and a metal salt of a derivative of the cyclic carboxylic acid are preferable as a compounding agent for an antifouling paint which functions as a hydrolysis controlling agent for an antifouling coating film or an elution assistant for an antifouling agent. The present inventors have further found that an antifouling paint composition comprising the compound (A) such as the cyclic carboxylic acid and a copolymer (B) for a self-polishing type antifouling paint, particularly a silyl ester copolymer, has excellent long-term storage stability, and a coating film formed by applying and curing the composition has a favorable hydrolysis rate, is excellent in long-term antifouling property in the static environment or the dynamic environment and has an excellent balance of these properties. Based on the finding, the present invention has been accomplished.

Patent document 1: Japanese Patent Laid-Open Publication No. 30071/1998

DISCLOSURE OF THE INVENTION PROBLEM TO BE SOLVED BY THE INVENTION

The present invention is intended to solve such problems associated with the prior art as described above, and it is an object of the present invention to provide a novel cycloalkenylcarboxylic acid, a novel bicycloalkenylcarboxylic acid, a salt thereof, etc., each of which is employable as a compounding agent for an antifouling paint similarly to rosin and is preferably employable as a compounding agent for an antifouling paint because it can be more stably supplied than rosin and has more uniform quality than rosin.

It is another object of the present invention to provide a compounding agent for an antifouling paint, which comprises the novel cycloalkenylcarboxylic acid, the novel bicycloalkenylcarboxylic acid or the salt thereof and has the above properties.

It is a further object of the present invention to provide an antifouling paint composition having excellent storage stability and capable of forming an antifouling coating film which is a small burden to the environment, is uniformly eroded at a given rate over a long period of time (uniform erodibility of coating film), can maintain excellent antifouling performance for a long period of time (long-term antifouling performance-maintaining property), exhibits excellent antifouling performance particularly in the highly fouling sea area or in the static environment and has an excellent balance of these properties, an antifouling coating film having the above properties, a ship, an underwater structure, a fishing tackle or a fishing net coated with the antifouling coating film, and an antifouling method for them.

MEANS TO SOLVE THE PROBLEM

The novel cycloalkenylcarboxylic acid according to the present invention is represented by the following formula [V], and the novel bicycloalkenylcarboxylic acid according to the present invention is represented by the following formula [VI].

Novel Cycloalkenylcarboxylic Acid [V]:

[Compound 1]

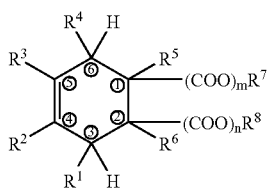

[V]

wherein $R^1$ is a hydrogen atom, a 3-methyl-2-butenyl group (also referred to as a "2-methyl-2-buten-4-yl group") or a 2-methyl-1-propenyl group (also referred to as a "2-methyl-2-propen-3-yl group"), when $R^1$ is a hydrogen atom, $R^2$ is a 4-methyl-3-pentenyl group (also referred to as a "2-methyl-2-penten-5-yl group") and $R^3$ and $R^4$ are each a hydrogen atom, when $R^1$ is a 3-methyl-2-butenyl group (2-methyl-2-buten-4-yl group), $R^2$ is a methyl group and $R^3$ and $R^4$ are each a hydrogen atom, when $R^1$ is a 2-methyl-1-propenyl group (2-methyl-2-propen-3-yl group), $R^2$ is a hydrogen atom and $R^3$ and $R^4$ are each a methyl group, $R^5$ and $R^6$ are each a hydrogen atom or an alkyl group of 1 to 10 carbon atoms, m and n are each a number of 0 or 1 (with the proviso that it does not occur that m and n are 0 at the same time), $R^7$ and $R^8$ are each a hydrogen atom or a hydrocarbon group, when m is 0, $R^7$ is a hydrogen atom, when m is 1, $R^7$ is a hydrogen atom or a hydrocarbon group, when n is 0, $R^8$ is a hydrogen atom, and when n is 1, $R^8$ is a hydrogen atom or a hydrocarbon group (with the proviso that it does not occur that $R^7$ and $R^8$ are hydrocarbon groups at the same time).

Novel Bicycloalkenylcarboxylic Acid [VI]:

[Compound 2]

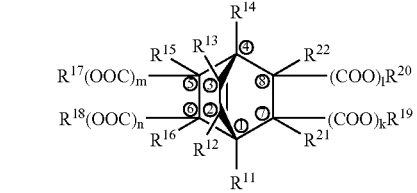

[VI]

wherein any one of $R^{11}$ and $R^{16}$ is an isopropyl group,

[A] in the case where $R^{11}$ is an isopropyl group, $R^{12}$ and $R^{13}$ are each a hydrogen atom, $R^{14}$ is a methyl group, $R^{15}$ and $R^{16}$ are each a hydrogen atom or an alkyl group of 1 to 10 carbon atoms, m and n are each a number of 0 or 1 (with the proviso that it does not occur that m and n are 0 at the same time), preferably one of them is 0 and the other is 1, $R^{17}$ and $R^{18}$ are each a hydrogen atom or a hydrocarbon group, k and l are each 0, $R^{19}$ and $R^{20}$ are each a hydrogen atom, $R^{21}$ and $R^{22}$ are each a hydrogen atom or an alkyl group of 1 to 10 carbon atoms, when m is 0, $R^{17}$ is a hydrogen atom, when m is 1, $R^{17}$ is a hydrogen atom, a hydrocarbon group or a metal atom, when n is 0, $R^{18}$ is a hydrogen atom, and when n is 1, $R^{18}$ is a hydrogen atom or a hydrocarbon group (with the proviso that it does not occur that $R^{17}$ and $R^{18}$ are hydrocarbon groups at the same time), and

[B] in the case where $R^{16}$ is an isopropyl group, $R^{11}$ and $R^{12}$ are each a hydrogen atom, $R^{13}$ is a methyl group, $R^{14}$ is a hydrogen atom, $R^{15}$ is a hydrogen atom or an alkyl group of 1 to 10 carbon atoms, m and n are each 0, $R^{17}$ and $R^{18}$ are each a hydrogen atom, k and l are each a number of 0 or 1 (with the proviso that it does not occur that k and l are 0 at the same time), preferably one of them is 0 and the other is 1, $R^{19}$ and $R^{20}$ are each a hydrogen atom or a hydrocarbon group, $R^{21}$ and $R^{22}$ are each a hydrogen atom or an alkyl group of 1 to 10 carbon atoms, when k is 0, $R^{19}$ is a hydrogen atom, when k is 1, $R^{19}$ is a hydrogen atom or a hydrocarbon group, when l is 0, $R^{20}$ is a hydrogen atom, and when l is 1, $R^{20}$ is a hydrogen atom or a hydrocarbon group (with the proviso that it does not occur that $R^{19}$ and $R^{20}$ are hydrocarbon groups at the same time).

In a preferred embodiment of the present invention, the cycloalkenylcarboxylic acid represented by the formula [V] is desirably represented by the following formula [Va], [Vb], [Vc], [Vd], [Ve], [Vf], [Vg] or [Vh], and the bicycloalkenylcarboxylic acid represented by the formula [VI] is desirably represented by the following formula [VIa], [VIb], [VIc] or [VId]. (If the atom or the group bonded to a carbon atom in the formulas [Va] to [Vh] and the formulas [VIa] to [VId] is a hydrogen atom (H), the hydrogen atom is omitted in these formulas. The same shall apply hereinafter.)

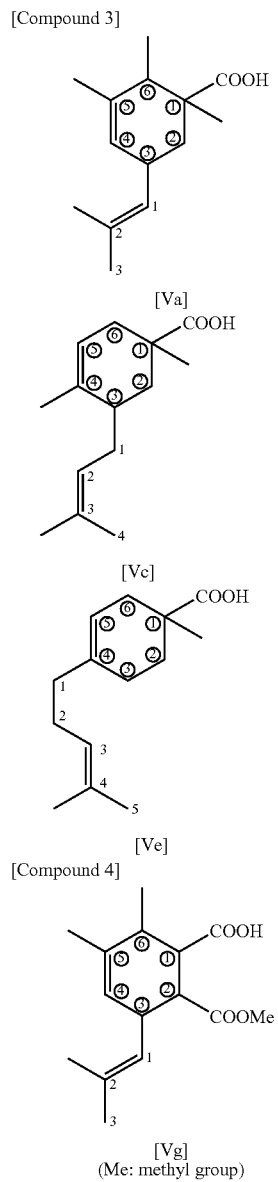

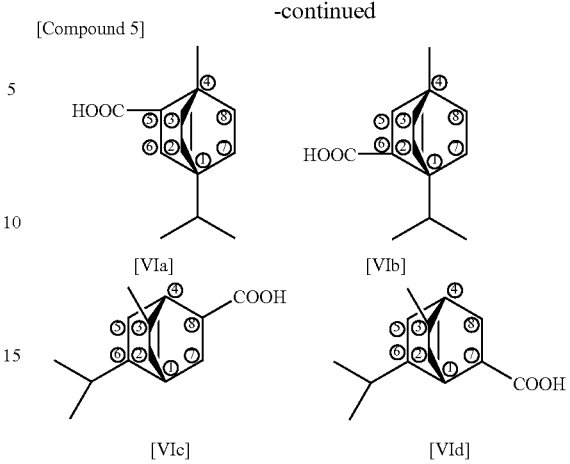

The process for preparing the novel cycloalkenylcarboxylic acid or the novel bicycloalkenylcarboxylic acid according to the present invention comprises subjecting [J] at least one terpene-based diene compound (conjugated diene compound) selected from the group consisting of alloocimene, ocimene, myrcene, α-terpinene and α-phellandrene and [K] at least one unsaturated carboxylic acid selected from α,β-unsaturated monocarboxylic acids and monoesters of α,β-unsaturated dicarboxylic acids to addition reaction.

A metal salt of the novel cycloalkenylcarboxylic acid of the invention or a metal salt of the novel bicycloalkenylcarboxylic acid of the invention is a monocarboxylic acid metal salt obtained by the reaction of a monocarboxylic acid represented by the formula [V] or [VI] with a metal compound, and is generally represented by the formula $(RCOO)_xM$ (M: metal atom, x: valence of metal atom).

The structure, the production process and other details of the metal salt are described later.

The compounding agent (A) for an antifouling paint according to the present invention comprises one or more substances selected from a cyclic carboxylic acid formed by the addition reaction of an unsaturated carboxylic acid with a conjugated diene compound, a derivative of the cyclic carboxylic acid (except a metal salt), a metal salt of the cyclic carboxylic acid, and a metal salt of a derivative of the cyclic carboxylic acid.

In a preferred embodiment of the compounding agent for an antifouling paint according to the invention, the cyclic carboxylic acid, the derivative of the cyclic carboxylic acid (except a metal salt), the metal salt of the cyclic carboxylic acid, or the metal salt of a derivative of the cyclic carboxylic acid is desirably the cycloalkenylcarboxylic acid represented by the formula [V] or the bicycloalkenylcarboxylic acid represented by the formula [VI] or a salt thereof.

The antifouling paint composition according to the present invention comprises (A) the compounding agent for an antifouling paint and (B) a copolymer for a self-polishing type antifouling paint.

The antifouling paint composition of the invention preferably further comprises an antifouling agent (C), and as the antifouling agent (C), copper or a copper compound (C1) is desirably contained.

In the present invention, an organic antifouling agent (C2) (except copper or a copper compound (C1)) may be contained as the antifouling agent (C).

In the present invention, the copolymer (B) for a self-polishing type antifouling paint is preferably a polymerizable unsaturated carboxylic acid hydroxy metal salt-based copolymer.

In the present invention, the copolymer (B) for a self-polishing type antifouling paint is desirably a copolymer having, in a molecule, a constituent unit derived from a polymerizable unsaturated carboxylic acid hydroxy metal compound represented by the following formula [I]:

$$R^1—COO—M—OH \qquad [I]$$

wherein $R^1$ is an unsaturated bond-containing organic group of $CH_2=C(CH_3)—$, $CH_2=CH—$, $HOOC—CH=CH—$ or $HOOC—CH=C(CH_3)—$, $—COOH$ may form a metal salt or an ester, and M is a metal atom, preferably a constituent unit derived from a (meth)acrylic acid hydroxy metal salt, more preferably a constituent unit derived from a (meth)acrylic acid hydroxy zinc salt or copper salt.

In the present invention, the copolymer (B) for a self-polishing type antifouling paint is desirably a polymerizable unsaturated carboxylic acid metal compound-based copolymer having a constituent unit derived from a polymerizable unsaturated carboxylic acid metal compound containing no hydroxyl group bonded to a metal atom, preferably a constituent unit derived from a polymerizable unsaturated carboxylic acid metal compound represented by the following formula [II], more preferably a constituent unit derived from a (meth)acrylic acid metal compound containing no hydroxyl group bonded to a metal atom, particularly preferably a constituent unit derived from a (meth)acrylic acid zinc salt or copper salt containing no hydroxyl group bonded to a zinc atom or a copper atom.

$$R^1—COO—M—L_n \qquad \text{Formula [II]}$$

Wherein $R^1$ is an unsaturated bond-containing organic group of $CH_2=C(CH_3)—$, $CH_2=CH—$, $HOOC—CH=CH—$ or $HOOC—CH=C(CH_3)—$, $—COOH$ may form a metal salt or an ester, M is a metal atom, L is an organic acid residue $—OCOR^2$ ($R^2$ is an alkyl group, a cycloalkyl group, an aromatic hydrocarbon group which may have a substituent, or an aralkyl group), and n is a number of "valence of the metal M(−1)".

In the present invention, the copolymer (B) for a self-polishing type antifouling paint is preferably a polymerizable unsaturated carboxylic acid metal salt-based copolymer which is obtained by copolymerizing (a) a (meth)acrylic acid zinc salt or copper salt monomer and (b) another monomer copolymerizable with the monomer (a), and contains constituent units derived from the (meth)acrylic acid zinc salt or copper salt monomer (a) in amounts of 2 to 50% by weight and constituent units derived from the copolymerizable another monomer (b) in amounts of 50 to 98% by weight (constituent units (a)+constituent units (b)=100% by weight).

In the present invention, the copolymer (B) for a self-polishing type antifouling paint is preferably a polymerizable unsaturated carboxylic acid silyl ester-based copolymer, more preferably a copolymer having, in a molecule, a constituent unit derived from a silyl unsaturated carboxylate monomer represented by the following formula [IIIA] and a constituent unit derived from an unsaturated monomer copolymerizable with the silyl unsaturated carboxylate monomer, particularly preferably a copolymer obtained by copolymerizing silyl (meth)acrylate and an unsaturated monomer copolymerizable with the silyl (meth)acrylate.

$$R^1—COO—Si(L^1L^2L^3) \qquad \text{Formula [IIIA]}$$

Wherein $R^1$ is an unsaturated bond-containing organic group of $CH_2=C(CH_3)—$, $CH_2=CH—$, $HOOC—CH=CH—$ or $HOOC—CH=C(CH_3)—$, $—COOH$ may form a metal salt or an ester, $L^1$, $L^2$ and $L^3$ may be the same or different and are each independently a hydrogen atom, an alkyl group, a cycloalkyl group, an aromatic hydrocarbon group, an aralkyl group or an alkylsilyloxy group, and these groups may have a substituent.

The antifouling coating film according to the present invention is formed from the above-mentioned antifouling paint composition.

The ship and the underwater structure according to the present invention are each coated with a coating film formed from the above-mentioned antifouling paint composition.

The fishing tackle and the fishing net according to the present invention are each coated with a coating film formed from the above-mentioned antifouling paint composition.

The antifouling method for a ship, an underwater structure, a fishing tackle or a fishing net according to the present invention comprises coating a surface of a ship, an underwater structure, a fishing tackle or a fishing net with a coating film comprising the above-mentioned antifouling paint composition.

EFFECT OF THE INVENTION

According to the present invention, there are provided a novel cycloalkenylcarboxylic acid, a novel bicycloalkenylcarboxylic acid and a salt thereof each of which is employable as a hydrolysis controlling agent for an antifouling coating film or an elusion assistant for an antifouling agent similarly to rosin, can be more stably supplied than rosin, has more uniform quality than rosin and is preferably employable as a compounding agent for an antifouling paint.

According to the present invention, there is further provided a compounding agent for an antifouling paint, which comprises the novel cycloalkenylcarboxylic acid, the novel bicycloalkenylcarboxylic acid or the salt thereof, is employable as a hydrolysis controlling agent for an antifouling coating film or an elution assistant for an antifouling agent similarly to rosin, can be more stably supplied than rosin, has more uniform quality than rosin and is preferable for an antifouling coating film.

According to the present invention, there are furthermore provided an antifouling paint composition having excellent storage stability and capable of forming an antifouling coating film which is a small burden to the environment, is uniformly eroded at a given rate over a long period of time (uniform erodibility of coating film), can maintain excellent antifouling performance for a long period of time (long-term antifouling performance-maintaining property), exhibits excellent antifouling performance particularly in the highly fouling sea area or in the static environment and has an excellent balance of these properties, an antifouling coating film having the above properties, a ship, an underwater structure, a fishing tackle or a fishing net coated with the antifouling coating film, and an antifouling method for them.

BRIEF DESCRIPTION OF THE DRAWINGS

FIG. 12 shows a MS spectrum of a compounding agent (AD-8) for an antifouling paint, said compounding agent being used in an example of the invention or a comparative example.

BEST MODE FOR CARRYING OUT THE INVENTION

Figure 1:
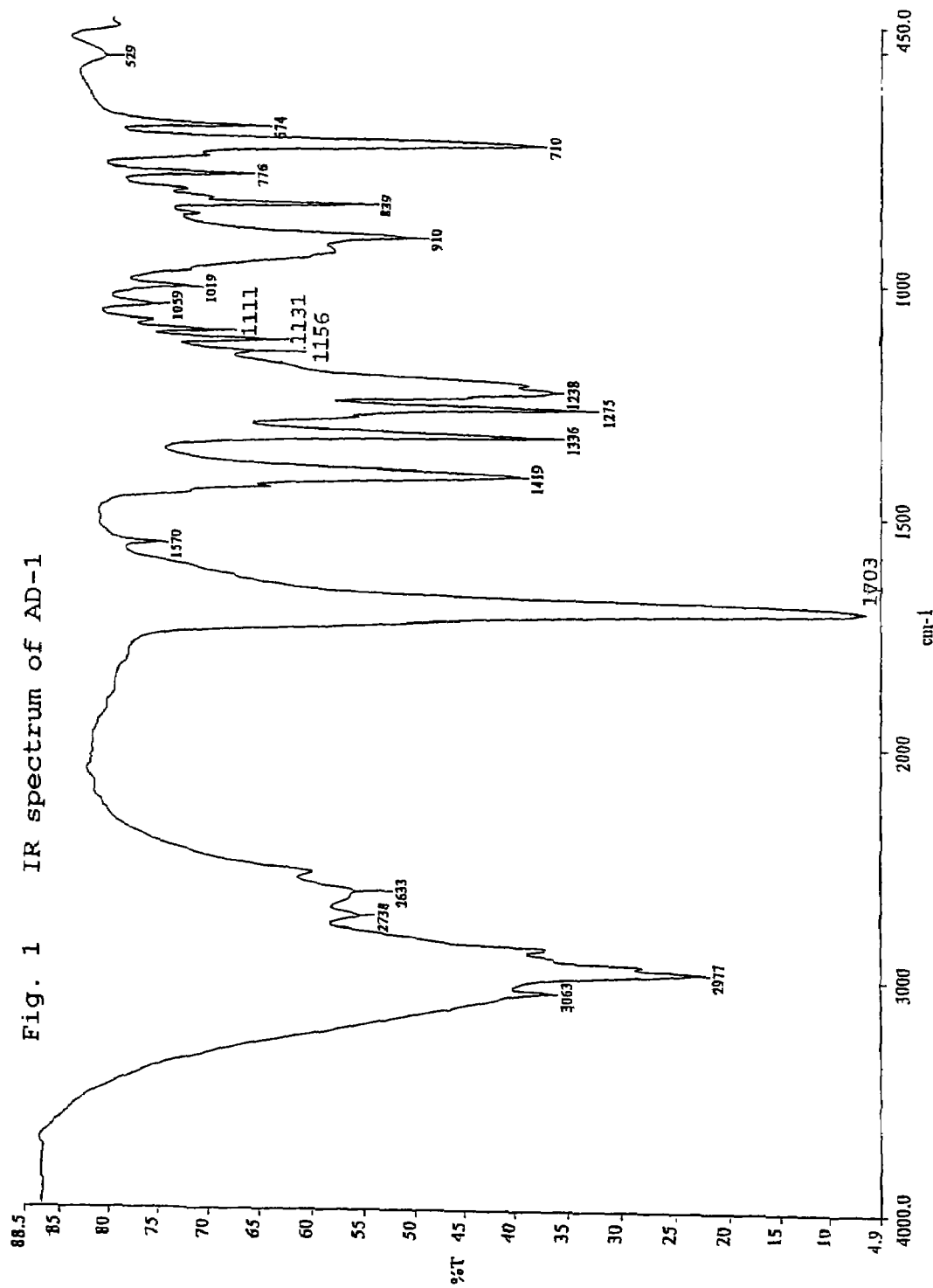
FIG. 1 shows an IR spectrum of a compounding agent (AD-1) for an antifouling paint, said compounding agent being used in an example of the invention or a comparative example.

The novel cycloalkenylcarboxylic acid, the novel bicycloalkenylcarboxylic acid, the derivative thereof, the compounding agent for an antifouling paint which comprises the acid or derivative, the antifouling paint composition, the antifouling coating film, the ship, underwater structure, fishing tackle or fishing net coated with the antifouling coating film, etc. according to the present invention are described in detail hereinafter.

<Novel Cycloalkenylcarboxylic Acid, Novel Bicycloalkenylcarboxylic Acid, Derivative Thereof, and Compounding Agent (A) for Antifouling Paint>

(Novel (Bi)Cycloalkenylcarboxylic Acid and Derivative Thereof)

The novel cycloalkenylcarboxylic acid, the novel bicycloalkenylcarboxylic acid (cycloalkenylcarboxylic acid and bicycloalkenylcarboxylic acid are together referred to as "(bi)cycloalkenylcarboxylic acid" simply) or a derivative thereof is a cyclic carboxylic acid formed by the addition reaction (Diels-Alder addition reaction) of a specific conjugated diene compound with a specific unsaturated carboxylic acid, a derivative of the cyclic carboxylic acid (except a metal salt), a metal salt of the cyclic carboxylic acid or a metal salt of a derivative of the cyclic carboxylic acid.

Of the above compounds, the novel cycloalkenylcarboxylic acid [V] or a salt thereof (the acid and the salt are together referred to as "cycloalkenylcarboxylic acid-based compound [V]") is represented by the following formula [V], and the novel bicycloalkenylcarboxylic acid [VI] or a salt thereof (the acid and the salt are together referred to as "bicycloalkenylcarboxylic acid-based compound [VI]") is represented by the following formula [VI].

The above novel compounds [V] and [VI] are obtained by subjecting,

[J] at least one terpene-based diene compound (conjugated diene compound) selected from the group consisting of alloocimene, ocimene, myrcene, α-terpinene and α-phellandrene which are diene components contained in natural terpene oil and,

[K] at least one unsaturated carboxylic acid selected from α,β-unsaturated monocarboxylic acids, α,β-unsaturated dicarboxylic acids and monoesters thereof to addition reaction (Diels-Alder reaction).

The novel (bi)cycloalkenylcarboxylic acid-based compounds [V] and [VI] may be obtained by, for example, forming salts of the novel (bi)cycloalkenylcarboxylic acids.

Novel Cycloalkenylcarboxylic Acid-Based Compound [V]:

[Compound 6]

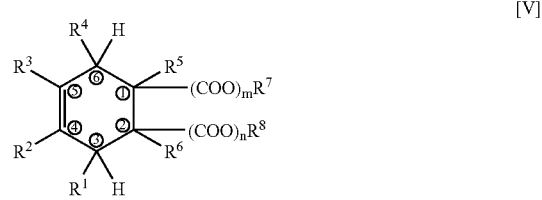

[V]

In the formula [V], $R^1$ is a hydrogen atom, a 3-methyl-2-butenyl group (2-methyl-2-buten-4-yl group) or a 2-methyl-1-propenyl group (2-methyl-2-propen-3-yl group), $R^2$ is a hydrogen atom, a methyl group or a 4-methyl-3-pentenyl group (2-methyl-2-penten-5-yl group), $R^3$ and $R^4$ are each a hydrogen atom or a methyl group, when $R^1$ is a hydrogen atom, $R^2$ is a 4-methyl-3-pentenyl group (2-methyl-2-penten-5-yl group) and $R^3$ and $R^4$ are each a hydrogen atom, when $R^1$ is a 3-methyl-2-butenyl group (2-methyl-2-buten-4-yl group), $R^2$ is a methyl group and $R^3$ and $R^4$ are each a hydrogen atom, when $R^1$ is a 2-methyl-1-propenyl group (2-methyl-2-propen-3-yl group), $R^2$ is a hydrogen atom and $R^3$ and $R^4$ are each a methyl group, $R^5$ and $R^6$ are each a hydrogen atom or an alkyl group of 1 to 10 carbon atoms, m and n are each a number of 0 or 1 (with the proviso that it does not occur that m and n are 0 at the same time), $R^7$ and $R^8$ are each a hydrogen atom or a hydrocarbon group, when m is 0, $R^7$ is a hydrogen atom, when m is 1, $R^7$ is a hydrogen atom or a hydrocarbon group, when n is 0, $R^8$ is a hydrogen atom, and when n is 1, $R^8$ is a hydrogen atom or a hydrocarbon group (with the proviso that it does not occur that $R^7$ and $R^8$ are hydrocarbon groups at the same time).

In more detail, $R^1$ in the formula [V] is a hydrogen atom, a 3-methyl-2-butenyl group (2-methyl-2-buten-4-yl group) or a 2-methyl-1-propenyl group (2-methyl-2-propen-3-yl group).

When $R^1$ is a hydrogen atom, $R^2$ is a 4-methyl-3-pentenyl group (2-methyl-2-penten-5-yl group) and $R^3$ and $R^4$ are each a hydrogen atom, as indicated in the following formula [Ve] (5a) or [Vf](5b).

When $R^1$ is a 3-methyl-2-butenyl group (2-methyl-2-buten-4-yl group), $R^2$ is a methyl group and $R^3$ and $R^4$ are each a hydrogen atom, as indicated in the following formula [Vc](4a) or [Vd](4b).

When $R^1$ is a 2-methyl-1-propenyl group (2-methyl-2-propen-3-yl group), $R^2$ is a hydrogen atom and $R^3$ and $R^4$ are each a methyl group, as indicated in the following formula [Va] (3a) or [Vb](3b).

$R^5$ and $R^6$ are each a hydrogen atom or an alkyl group of 1 to 10 carbon atoms, preferably 1 to 5 carbon atoms, particularly preferably 1 to 3 carbon atoms.

The alkyl group is, for example, a branched alkyl group, a chain alkyl group or a cyclic alkyl group (6 or more carbon atoms) which may have a substituent such as the above alkyl group. Above all, a chain alkyl group is preferable from the viewpoints of ease of preparation, inexpensiveness, optimization of hydrolysis rate of an antifouling coating film containing it, optimization of elution rate of an antifouling agent, etc. Examples of such alkyl groups include methyl, ethyl, n-propyl, i-propyl, n-butyl, t-butyl, n-pentyl, n-hexyl and cyclohexyl. Of these, preferable are alkyl groups satisfying the above requirements.

m and n are each a number of 0 or 1 (with the proviso that it does not occur that m and n are 0 at the same time, as described later).

That is to say, when m or n is 0, $—(COO)_m$ and $—(COO)_n$ are each a single bond (—), and when m or n is 1, $—(COO)_m$ and $—(COO)_n$ are each a carbonyloxy group (—COO—). (Also in case of k and l which are described later, the same shall apply.)

$R^7$ and $R^8$ are each a hydrogen atom or a hydrocarbon group.

In more detail, $R^7$ and $R^8$ are each a hydrogen atom or a hydrocarbon group, such as an alkyl group of 1 to 10 carbon atoms, preferably an alkyl group of 1 to 5 carbon atoms.

In the present invention, when m of the $—(COO)_m R^7$ part in the formula [V] is 0, $R^7$ is a hydrogen atom (H), and when m is 1, $R^7$ is a hydrogen atom or a hydrocarbon group (e.g., alkyl group of 1 to 10 carbon atoms, preferably alkyl group of 1 to 5 carbon atoms).

That is to say, when m is 0 and $R^7$ is H (hydrogen atom), the $—(COO)_m R^7$ in the formula [V] is —H, when m is 1 and $R^7$ is H (hydrogen atom), it is a carboxyl group (—COOH), and when m is 1 and $R^7$ is a hydrocarbon group, it is —COOR$^7$ (ester).

In the present invention, however, it does not occur that m and n in the formula [V] are 0 at the same time, as described above. If m and n are 0 at the same time (m=n=0), $—(COO)_m R^7$ and $—(COO)_n R^7$ are each —H, and the compound [V] is neither a carboxylic acid nor a derivative thereof (e.g., ester, salt). Such a compound is not included in the compound [V] of the invention.

The $—(COO)_m R^8$ in the formula [V] is similar to the above-mentioned $—(COO)_m R^7$. That is to say, when n is 0, $R^8$ is a hydrogen atom (H), and when n is 1, $R^8$ is a hydrogen atom or the same hydrocarbon group as described above.

Accordingly, when n is 0 and $R^8$ is H (hydrogen atom), the $—(COO)_n R^8$ is —H, when n is 1 and $R^8$ is H (hydrogen atom), it is a carboxyl group (—COOH), and when n is 1 and $R^8$ is a hydrocarbon group, it is —COOR$^8$ (ester).

In the present invention, it does not occur that $R^7$ and $R^8$ in the formula [V] are hydrocarbon groups at the same time.

That is to say, the cycloalkenylcarboxylic acid-based compound [V] is a carboxylic acid or a derivative thereof, and examples of the carboxylic acids include such monocarboxylic acids as represented by the formulas (3a) to (5b) and such monocarboxylic acids (monoesters of dicarboxylic acids) as represented by the formulas (8a) and (8b). Examples of the carboxylic acid derivatives include metal salts of these carboxylic acids.

Preferred embodiments of the novel cycloalkenylcarboxylic acid-based compounds [V] of the invention represented by the formula [V] include compounds represented by the following formulas:

[Va]   (1,5,6-trimethyl-3-(2-methyl-1-propenyl)-4-cyclohexen-1-yl-carboxylic acid),

[Vb]   (1,4,5-trimethyl-2-(2-methyl-1-propenyl)-3-cyclohexen-1-yl-carboxylic acid),

[Vc] (1,4-dimethyl-3-(3-methyl-2-butenyl)-3-cyclohexen-1-yl-carboxylic acid),

[Vd] (1,3-dimethyl-2-(3-methyl-2-butenyl)-3-cyclohexen-1-yl-carboxylic acid),

[Ve] (1-methyl-4-(4-methyl-3-pentenyl)-4-cyclohexen-1-yl-carboxylic acid),

[Vf] (1-methyl-3-(4-methyl-3-pentenyl)-3-cyclohexen-1-yl-carboxylic acid),

[Vg]   (2-methoxycarbonyl-3-(2-methyl-1-propenyl)-5,6-dimethyl-4-cyclohexen-1-yl-carboxylic acid), and

[Vh] (methyl 2-carboxy-3-(2-methyl-1-propenyl)-5,6-dimethyl-4-cyclohexen-1-yl-carboxylate).

These novel cycloalkenylcarboxylic acid-based compounds [V] represented by the above formulas [Va] to [Vh] are readily produced, can be inexpensively produced with uniform qualities, can be added to an antifouling paint as an agent for controlling elution rate of an antifouling agent, and can be used as a compounding agent for an antifouling paint. The compound [V] is desirably contained in an antifouling coating film from the viewpoints of optimization of hydrolysis rate of the antifouling coating film, optimization of elution rate of an antifouling agent and improvement of antifouling property.

The above compounds of the invention are each obtained as a mixture of isomers in the course of the production reaction, and it is very difficult to isolate them. In the mixture, various isomers are present, and therefore, in the use of the compound as a compounding agent for an antifouling paint, there are advantages that crystallization of the compound in a coating paint or a coating film is suppressed and a coating film having excellent adhesion to an adherend and having plasticity is obtained.

Rosin having been widely used heretofore is a substance composed of many kinds of isomers similarly to the novel cycloalkenylcarboxylic acid-based compound [V] (compounding agent for antifouling paint) of the invention and is characterized by having the above-mentioned advantages. The cycloalkenylcarboxylic acid-based compound [V] resembles the rosin.

[Compound 7]

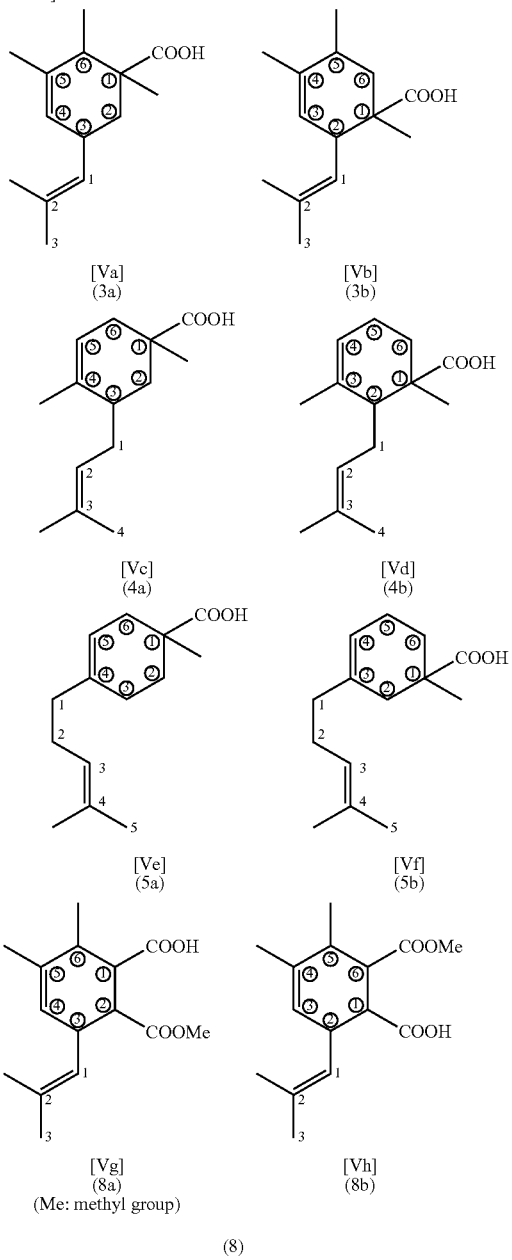

The novel bicycloalkenylcarboxylic acid [VI] (bicycloalkenylcarboxylic acid-based compound [VI]) of the invention is represented by the following formula [VI].

Novel Bicycloalkenylcarboxylic Acid-Based Compound [VI]:

[Compound 9]

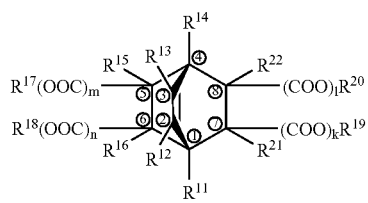

In the formula [VI], $R^{11}$ is a hydrogen atom or an isopropyl group, $R^{12}$ is a hydrogen atom, $R^{13}$ and $R^{14}$ are each a hydrogen atom or a methyl group, $R^{15}$ and $R^{16}$ are each a hydrogen atom or an alkyl group of 1 to 10 carbon atoms (particularly, $R^{16}$ is sometimes an isopropyl group), m, n, k and l are each a number of 0 or 1, $R^{17}$, $R^{18}$, $R^{19}$ and $R^{20}$ are each a hydrogen atom or a hydrocarbon group (preferably alkyl group of 1 to 10 carbon atoms, more preferably alkyl group of 1 to 5 carbon atoms, particularly preferably alkyl group of 1 to 3 carbon atoms; the same shall apply hereinafter with respect to the hydrocarbon group), when m, n, k or l is 0, $R^{17}$, $R^{18}$, $R^{19}$ or $R^{20}$ is a hydrogen atom correspondingly thereto, when m, n, k or l is 1, $R^{17}$, $R^{18}$, $R^{19}$ or $R^{20}$ is a hydrogen atom or a hydrocarbon group (preferably the aforesaid group) correspondingly thereto, and the following requirements (i) and (ii) are satisfied:

(i) in the case where $R^{11}$ is an isopropyl group, $R^{12}$ and $R^{13}$ are each a hydrogen atom (H), $R^{14}$ is a methyl group, k=l=0, and $R^{19}$ and $R^{20}$ are each a hydrogen atom (H), and (ii) in the case where $R^{16}$ is an isopropyl group, $R^{11}$, $R^{12}$ and $R^{14}$ are each a hydrogen atom (H), $R^{13}$ is a methyl group, and m=n=0 (in each embodiment, it does not occur that $R^{17}$ and $R^{18}$ are hydrocarbon groups at the same time, and it does not occur that $R^{19}$ and $R^{20}$ are hydrocarbon groups at the same time, and it does not occur that m, n, k and l are 0 at the same time).

$R^{21}$ and $R^{22}$ are each a hydrogen atom or an alkyl group of 1 to 10 carbon atoms.

In a preferred embodiment of the invention, any one of $R^{11}$ and $R^{16}$ in the formula [VI] is an isopropyl group, and $R^{11}$ to $R^{22}$ (except $R^{11}$), m, n, k and l in the formula [VI] desirably satisfy the following relationships.

Preferred embodiments of the invention in a case [A] where $R^{11}$ in the formula [VI] is an isopropyl group and in a case [B] where $R^{16}$ in the formula [VI] is an isopropyl group are described below in detail.

[A] Case where $R^{11}$ is Isopropyl Group

In the case where $R^{11}$ is an isopropyl group, $R^{12}$ to $R^{22}$, m, n, k and l in the formula [VI] are as follows.

That is to say, in the formula [VI], $R^{12}$ and $R^{13}$ are each a hydrogen atom, $R^{14}$ is a methyl group, $R^{15}$ and $R^{16}$ are each a hydrogen atom or an alkyl group of 1 to 10 carbon atoms similarly to $R^5$ and $R^6$ in the formula [V], preferably the same group as described for $R^5$ and $R^6$, m and n are each a number of 0 or 1 (with the proviso that it does not occur that m and n are 0 at the same time), preferably one of them is 0 and the other is 1, and $R^{17}$ and $R^{18}$ are each a hydrogen atom or a hydrocarbon group (preferably the aforesaid group) similarly to $R^7$ and $R^8$ in the formula [V] (with the proviso that it does not occur that $R^{17}$ and $R^{18}$ are hydrocarbon groups at the same time).

In the formula [VI], k and l are each 0, and $R^{19}$ and $R^{20}$ are each a hydrogen atom.

That is to say, —(COO)$_k$R$^{19}$ and —(COO)$_l$R$^{20}$ in the formula [VI] are each —H. Therefore, taking it into consideration that it does not occur that m and n are 0 at the same time as previously described, the number of carbonyloxy groups (COO) or carboxyl groups (COOH) present in the formula [VI] is up to 1 or 2, and an embodiment containing 3 or 4 groups is not included.

Consequently, in the case where $R^{11}$ is an isopropyl group, the bicycloalkenylcarboxylic acid-based compound [VI] is a monocarboxylic acid or a metal salt thereof similarly to the cycloalkenylcarboxylic acid-based compound [V].

(In case of m=n=0, —(COO)$_m$R$^{17}$ and —(COO)$_m$R$^{18}$ both become —H, and taking it into consideration that —(COO)$_k$R$^{19}$ and —(COO)$_l$R$^{2}$ are each —H as described above, the compound [VI] is not a carboxylic acid, and such a compound is not included in the compound [VI] of the invention.)

R$^{21}$ and R$^{22}$ are each a hydrogen atom or an alkyl group of 1 to 10 carbon atoms similarly to R$^5$ and R$^6$ in the formula [V].

In the present invention, when m of the —(COO)$_m$R$^{17}$ part in the formula [VI] is 0, R$^{17}$ is a hydrogen atom, and when m is 1, R$^{17}$ is a hydrogen atom or a hydrocarbon group (preferably the aforesaid group).

Accordingly, when m is 0 and R$^{17}$ is H (hydrogen atom), the —(COO)$_m$R$^{17}$ is —H, when m is 1 and R$^{17}$ is H (hydrogen atom), it is a carboxyl group (—COOH), and when m is 1 and R$^{17}$ is a hydrocarbon group, it is —COOR$^{17}$ (ester), similarly to the —(COO)$_m$R$^7$ in the formula [V].

When n of the —(COO)$_n$R$^{18}$ part in the formula [VI] is 0, R$^{18}$ is a hydrogen atom, and when n is 1, R$^{18}$ is a hydrogen atom or a hydrocarbon group (preferably the aforesaid group).

Accordingly, the —(COO)$_n$R$^{18}$ is —H, a carboxyl group (—COOH) or an ester (—COOR$^8$), similarly to the —(COO)$_n$R$^8$ (or —(COO)$_m$R$^7$) in the formula [V].

(However, it does not occur that R$^{17}$ and R$^{18}$ are hydrocarbon groups at the same time.)

As described above, in the case [A] where R$^{11}$ is an isopropyl group, the —(COO)$_k$R$^{19}$ and —(COO)$_l$R$^{20}$ parts of the four parts —(COO)$_m$R$^{17}$, —(COO)$_n$R$^{18}$, —(COO)$_k$R$^{19}$ and —(COO)$_l$R$^{20}$ which can have a carbonyloxy group (COO) in the formula [VI] are each —H, so that the bicycloalkenylcarboxylic acid-based compound [VI] can become a monocarboxylic acid or its derivative (salt), but it does not become a di-, tri- or tetracarboxylic acid.

In the formula [VI], further, it does not occur that R$^{17}$ and R$^{18}$ are hydrocarbon groups at the same time, as described above. Therefore, when the bicycloalkenylcarboxylic acid-based compound [VI] is an ester, it is a monocarboxylic acid ester or a monoester of a dicarboxylic acid, and a diester (except cyclic diester) of a dicarboxylic acid is not included.

[B] Case where R$^{16}$ is Isopropyl Group

In the case where R$^{16}$ is an isopropyl group, R$^{12}$ to R$^{22}$ (except R$^{16}$), m, n, k and l in the formula [VI] are as follows.

That is to say, in the formula [VI], R$^{11}$ and R$^{12}$ are each a hydrogen atom, R$^{13}$ is a methyl group, R$^{14}$ is a hydrogen atom, and R$^{15}$ is a hydrogen atom or an alkyl group of 1 to 10 carbon atoms similarly to the above.

In the formula [VI], m and n are each 0, and R$^{17}$ and R$^{18}$ are each a hydrogen atom.

k and l are each a number of 0 or 1 (with the proviso that it does not occur that k and l are 0 at the same time), preferably one of them is 0 and the other is 1.

That is to say, —(COO)$_m$R$^{17}$ and —(COO)$_n$R$^{18}$ in the formula [VI] are each —H. Therefore, taking it into consideration that it does not occur that k and l are 0 at the same time as previously described, the number of carbonyloxy groups (COO) or carboxyl groups (COOH) present in the formula [VI] is up to 1 or 2, and an embodiment containing 3 or 4 groups is not included, not only in the case where R$^{11}$ is an isopropyl group but also in the case where R$^{16}$ is an isopropyl group.

Consequently, also in the case where R$^{16}$ is an isopropyl group, the bicycloalkenylcarboxylic acid-based compound [VI] is the same compound as previously described, such as a monocarboxylic acid or a metal salt thereof.

R$^{19}$ and R$^{20}$ are each a hydrogen atom or the same hydrocarbon group as above, similarly to R$^{17}$ and R$^{18}$ in the case where R$^{11}$ is an isopropyl group (or R$^5$ and R$^6$ in the formula [V]).

R$^{21}$ and R$^{22}$ are each a hydrogen atom or an alkyl group of 1 to 10 carbon atoms, similarly to R$^{15}$ and R$^{16}$ in the case where R$^{11}$ is an isopropyl group (or R$^5$ and R$^6$ in the formula [V]).

In the present invention, further, when k of the —(COO)$_k$R$^{19}$ part in the formula [VI] is 0, R$^{19}$ is a hydrogen atom, and when k is 1, R$^{19}$ is a hydrogen atom or the same hydrocarbon group as previously described.

Accordingly, when k is 0 and R$^{19}$ is H, the —(COO)$_k$R$^{19}$ is —H, when k is 1 and R$^{19}$ is H, it is a carboxyl group (—COOH), and when k is 1 and R$^{19}$ is a hydrocarbon group, it is —COOR$^{19}$ (ester), similarly to the —(COO)$_m$R$^7$ in the formula [V].

When l of the —(COO)$_n$R$^{20}$ part in the formula [VI] is 0, R$^{20}$ is a hydrogen atom, and when l is 1, R$^{20}$ is a hydrogen atom or the same hydrocarbon group as previously described.

Accordingly, the —(COO)$_l$R$^{20}$ is —H, a carboxyl group (—COOH) or an ester (—COOR$^8$), similarly to the —(COO)$_m$R$^{17}$ in the formula [VI] in the case where R$^{11}$ is an isopropyl group.

(Also in the case where R$^{16}$ is an isopropyl group, however, it does not occur that R$^{19}$ and R$^{20}$ in the formula [VI] are hydrocarbon groups at the same time, similarly to the case where R$^{11}$ is an isopropyl group.)

As described above, also in the case [B] where R$^{16}$ is an isopropyl group, the —(COO)$_k$R$^{19}$ and —(COO)$_l$R$^{20}$ parts of the four parts which can have a carbonyloxy group (COO) in the formula [VI] are each —H, so that the bicycloalkenylcarboxylic acid-based compound [VI] can become a monocarboxylic acid or its derivative (salt), but it does not become a di-, tri- or tetracarboxylic acid, similarly to the case [A] where R$^{11}$ is an isopropyl group.

As is clear from the above descriptions of m, n, k and l in the formula [VI], when at least one of m and n is 1, both of k and l become 0, and when at least one of k and l is 1, both of m and n become 0. Consequently, in the compounds of the formula [VI], a monocarboxylic acid and its salt are included, but a poly-(di- or higher) carboxylic acid such as a di-, tri- or tetracarboxylic acid is not included. Therefore, an ester and a salt of the tri- or tetracarboxylic acid are not included. Further, when the bicycloalkenylcarboxylic acid-based compound [VI] represented by the formula [VI] is an ester of a dicarboxylic acid, it indicates a half ester (monoester), and a diester is not included.

Preferred embodiments of the novel bicycloalkenylcarboxylic acid-based compounds [VI] of the invention represented by the formula [VI] include compounds represented by the following formulas:

[VIa] (1-i-propyl-4-methyl-bicyclo[2,2,2]2-octen-5-yl-carboxylic acid),

[VIb] (1-i-propyl-4-methyl-bicyclo[2,2,2]2-octen-6-yl-carboxylic acid),

[VIc] (6-i-propyl-3-methyl-bicyclo[2,2,2]2-octen-8-yl-carboxylic acid), and

[VId] (6-i-propyl-3-methyl-bicyclo[2,2,2]2-octen-7-yl-carboxylic acid).

The novel bicycloalkenylcarboxylic acid-based compounds [VI] represented by the above formulas [VIa] to [VId] have advantages such as ease of preparation, inexpensiveness and uniform qualities and can be added to an antifouling paint as a compounding agent for an antifouling paint, particularly as an agent for controlling elution rate of an antifouling agent. The compound [VI] is desirably contained in an antifouling coating film from the viewpoints of optimization of hydrolysis rate of the antifouling coating film and optimization of elution rate of an antifouling agent.

[Compound 10]

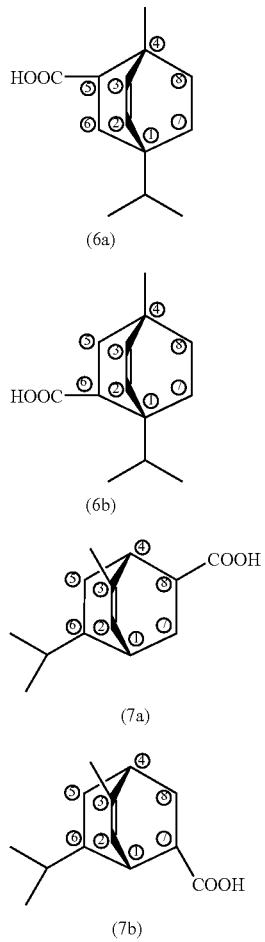

(6a) [VIa]

(6b) [VIb]

(7a) [VIc]

(7b) [VId]

Compounding Agent (A) for Antifouling Paint

The compounding agent (A) for an antifouling paint according to the invention comprises one or more substances selected from a cyclic carboxylic acid formed by the addition reaction (Diels-Alder addition reaction) of an unsaturated carboxylic acid with a conjugated diene compound, and derivatives of the cyclic carboxylic acid (e.g., esters and metal salts of the cyclic carboxylic acid).

In a preferred embodiment of the compounding agent for an antifouling paint according to the invention, the cyclic carboxylic acid or the derivative of the cyclic carboxylic acid (e.g., ester or metal salt of the cyclic carboxylic acid) is desirably the novel cycloalkenylcarboxylic acid [V], the novel bicycloalkenylcarboxylic acid [VI] or a salt thereof.

Preparation of Novel Cycloalkenylcarboxylic Acid, Novel Bicycloalkenylcarboxylic Acid and Derivative Thereof.

In the process of the invention for preparing cyclic carboxylic acids and esters or salts thereof including the novel cycloalkenylcarboxylic acid, the novel bicycloalkenylcarboxylic acid (both acids being together referred to as "cyclic carboxylic acid") of the invention and salts thereof,

[J] at least one terpene-based diene compound (conjugated diene compound) selected from the group consisting of alloocimene, ocimene, myrcene, α-terpinene and α-phellandrene and

[K] at least one unsaturated carboxylic acid, ester thereof or salt thereof (unsaturated carboxylic acid-based compound) selected from α,β-unsaturated monocarboxylic acids, α,β-unsaturated dicarboxylic acids and monoesters thereof are subjected to addition reaction.

In the present invention, it is possible that the terpene-based diene compound [J] and an unsaturated carboxylic acid as the unsaturated carboxylic acid-based compound [K] are allowed to react with each other first and then esterification or formation of a salt is carried out.

The cyclic carboxylic acids, esters thereof and salts thereof obtained by the above process, such as the novel cyclic carboxylic acids and salts thereof, can be favorably used as compounding agents for antifouling paints, etc. for the aforesaid reasons.

In the present invention, cyclic carboxylic acids other than the above-mentioned ones, esters thereof and salts thereof can be also favorably used as compounding agents for antifouling paints, and these compounds can be also prepared by utilizing the addition reaction (Diels-Alder addition reaction) of an unsaturated carboxylic acid with a conjugated diene compound.

Examples of the conjugated diene compounds employable for the synthesis of the cyclic carboxylic acids including the novel compounds [V] and [VI] of the invention include chain compounds, such as butadiene, isoprene, 1,3-pentadiene, alloocimene, ocimene and myrcene, and cyclic compounds, such as furan, cyclopentadiene, 1,3-cyclohexadiene, α-terpinene and α-phellandrene.

Of the above conjugated diene compounds, butadiene, cyclopentadiene, alloocimene, myrcene and α-terpinene are preferable in the invention.

From the viewpoints of antifouling property and proper erodibility of the resulting coating film, the conjugated diene compound is preferably conjugated diene having a molecular weight of 54 to 600.

Examples of the unsaturated compounds (dienophiles) which are employable for the synthesis of the cyclic carboxylic acids including the novel compounds [V] and [VI] of the invention and added to the conjugated diene include unsaturated carboxylic acids and various compounds of unsaturated carboxylic acids.

Examples of the unsaturated carboxylic acids include:
unsaturated monocarboxylic acids, such as (meth)acrylic acid, linoleic acid, linolenic acid, oleic acid and propiolic acid (HC≡CCOOH); and monoalkyl esters (number of carbon atoms of alkyl group: 1 to 20) which are half esters of unsaturated dicarboxylic acids, such as monomethyl maleate, monoethyl maleate, monopropyl maleate, monobutyl maleate, monophenetyl maleate, monomethyl fumarate, monoethyl fumarate, monopropyl fumarate, monobutyl fumarate, monopentyl fumarate, monomethyl itaconate, monoethyl itaconate, monopropyl itaconate, monobutyl itaconate, monpentyl itaconate, monomethyl citraconate, monoethyl citraconate and monobutyl citraconate; and monoaryl esters which are half esters of unsaturated dicarboxylic acids, such as monophenyl maleate and monopentachlorophenyl fumarate.

Of the above unsaturated carboxylic acids, (meth)acrylic acid is preferable.

As another dienophile, p-benzoquinone is available.

As the dienophiles for use in the invention, compounds having active groups, such as carbonyl group (compound having this group: e.g., p-benzoquinone), nitrile group, nitro group, halogen group, acetoxy group, phenyl group, sulfone group, oxymethyl group, aminomethyl group and cyanomethyl group, which are adjacent to unsaturated bonds, are also available in addition to the above-mentioned unsaturated carboxylic acids.

Examples of the cyclic carboxylic acids formed by the addition reaction (Diels-Alder reaction) of the conjugated diene compound with the unsaturated carboxylic acid that is one dienophile include:

monocyclic carboxylic acids represented by the following formula (1) and formed by the addition reaction of cyclopentadiene (CPD) with acrylic acid (AA), such as bicyclo[2,2,1]2-hepten-6-yl-carboxylic acid (compound A-1, weight of 1 mol (Mw): 138), monocyclic carboxylic acids represented by the following formula (2) and formed by the addition reaction of cyclopentadiene (CPD) with methacrylic acid (MAA), such as 6-methyl bicyclo[2,2,1]2-hepten-6-yl-carboxylic acid (compound A-2, Mw: 152), monocyclic carboxylic acids represented by the following formula (3) and formed by the addition reaction of alloocimene with methacrylic acid (MAA), such as 1,5,6-trimethyl-3(2-methyl-1-propenyl)-4-cyclohexen-1-yl-carboxylic acid (compound A-3a, Mw: 222) and 1,4,5-trimethyl-2(2-methyl-1-propenyl)3-cyclohexen-1-yl-carboxylic acid (compound A-3b, Mw: 222), monocyclic carboxylic acids represented by the following formula (4) and formed by the addition reaction of ocimene with methacrylic acid (MAA), such as 1,4-dimethyl-3(3-methyl-2-butenyl)4-cyclohexen-1-yl-carboxylic acid (compound A-4-a, Mw: 222) and 1,3-dimethyl-2(3-methyl-2-butenyl)3-cyclohexen-1-yl-carboxylic acid (compound A-4b, Mw: 222), monocyclic carboxylic acids represented by the following formula (5) and formed by the addition reaction of myrcene with methacrylic acid (MAA), such as 1-methyl-4(4-methyl-3-pentenyl)4-cyclohexen-1-yl-carboxylic acid (compound A-5a, Mw: 222) and 1-methyl-3(4-methyl-3-pentenyl)3-cyclohexen-1-yl-carboxylic acid (compound A-5b, Mw: 222), dicyclic carboxylic acids represented by the following formula (6) and formed by the addition reaction of α-terpinene with acrylic acid (AA), such as 1-i-propyl-4-methyl-bicyclo[2,2,2]2-octen-5-yl-carboxylic acid (compound A-6a, Mw: 208) and 1-i-propyl-4-methyl-bicyclo[2,2,2]2-octen-6-yl-carboxylic acid (compound A-6b, Mw: 208), and dicyclic carboxylic acids represented by the following formula (7) and formed by the addition reaction of α-phellandrene with acrylic acid (AA), such as 6-i-propyl-3-methyl-bicyclo[2,2,2]2-octen-8-yl-carboxylic acid (compound A-7a, Mw: 208) and 6-i-propyl-3-methyl-bicyclo[2,2,2]2-octen-7-yl-carboxylic acid (compound A-7b, Mw: 208).

Further, also available are monocyclic carboxylic acids represented by the following formula (8) and formed by the addition reaction of alloocimene with monomethylmaleic acid, such as [Vg]: 2-methoxycarbonyl-3-(2-methyl-1-propenyl)-5,6-dimethyl-4-cyclohexen-1-yl-carboxylic acid (compound A-8a, Mw (mole weight): 266) and [Vh]: methyl 2-carboxy-3-(2-methyl-1-propenyl)-5,6-dimethyl-4-cyclohexen-1-yl-carboxylate (compound A-8b, Mw (mole weight): 266).

These compounds (cyclic carboxylic acids) are usually obtained as mixtures containing various isomers, and taking into consideration difficulty in isolation and excellent properties given when a mixture of isomers is used as a compounding agent for an antifouling paint, such as properties that crystallization in a paint or a coating film is suppressed and a coating film having excellent adhesion and plasticity is obtained, they are often used in the form (state) of isomer mixtures.

The synthesis of the cyclic carboxylic acid can be carried out utilizing publicly known Diels-Alder reaction. In the synthesis, a publicly known catalyst such as a solid acid can be used when needed. Although the reaction product can be used without being purified, it may be purified by a known method such as vacuum distillation or recrystallization.

The cyclic carboxylic acid can be synthesized by Diels-Alder reaction of a conjugated diene compound with an unsaturated carboxylic acid. In the reaction of the conjugated diene compound with the unsaturated carboxylic acid, a catalyst is preferably employed, and the catalyst is, for example, a solid acid such as activated clay or heteropoly-acid. In the reaction, to the conjugated diene compound and the unsaturated carboxylic acid, a catalyst such as activated clay is added in an amount of 0.01 to 2% by weight, preferably 0.05 to 0.5% by weight, based on the amount of the conjugated diene compound, and they are reacted under the conditions of a reaction temperature of 60 to 100° C., preferably 70 to 90° C., a reaction time of 6 to 60 hours, preferably 12 to 40 hours, and a pressure of 0.8 to 10 atm, preferably 0.9 to 5 atm, whereby a reaction product containing the cyclic carboxylic acid (usually isomer mixture) of the invention can be obtained.

The reaction product can be used as it is without being purified, as described above, but if necessary, it can be used after removal of insolubilities by filtration or removal of low-boiling point substances such as unreacted substances by distillation (unreacted substances usually have lower boiling point than the desired cyclic carboxylic acid of the invention). The reaction product may be purified by a known method such as rectification, vacuum distillation, recrystallization or solvent fractionation.

[Compound 11]

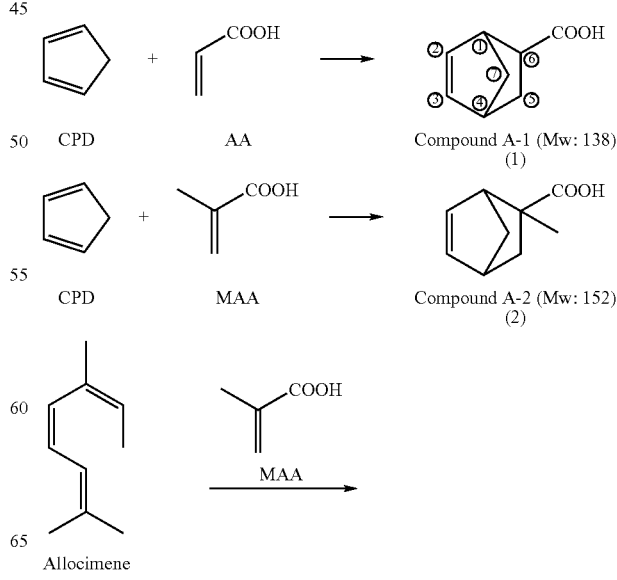

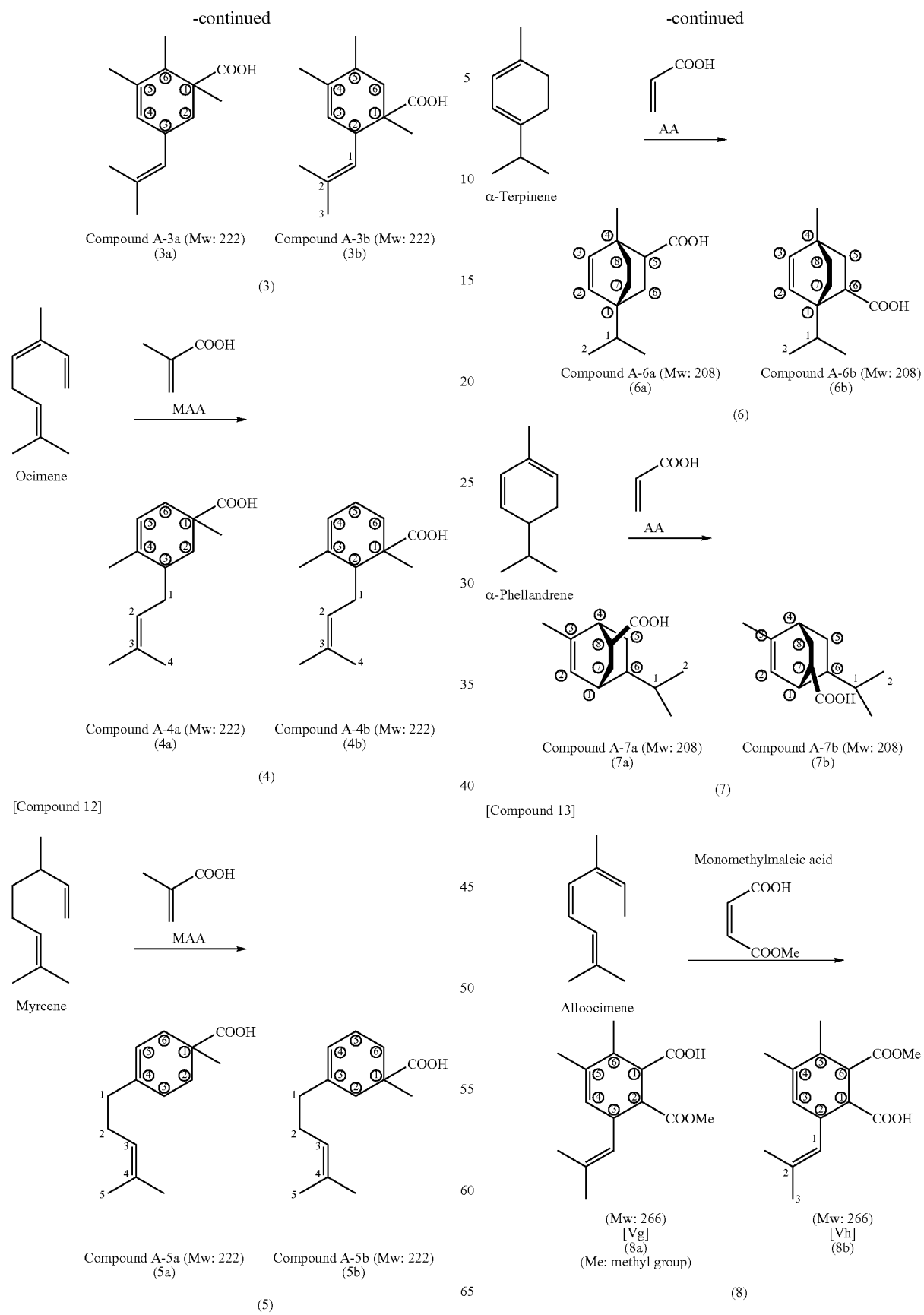

Of the above cyclic carboxylic acids, the compounds (2), (3), (5) and (8) are particularly preferable from the viewpoints of antifouling property and proper erodibility of the resulting antifouling coating film.

In case of, for example, the carboxylic acid represented by the formula (1) or (2) (compound A-1 or compound A-2), the following four isomers are present depending upon direction and position of the addition of (meth)acrylic acid to cyclopentadiene (CPD) that is a raw material used, or production of endo form/exo form.

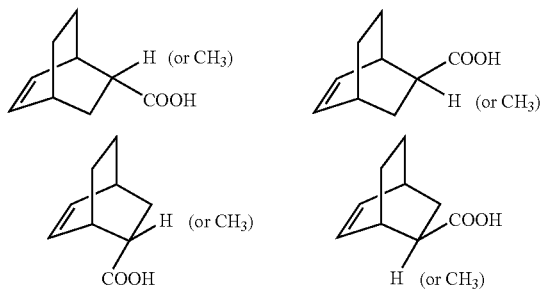

The same shall apply also to the later-described preparation examples of carboxylic acids (AD-1) and (AD-3).

In the case where alloocimene is used as a raw material for preparing the carboxylic acid, the alloocimene itself is a mixture of the following three isomers.

[Compound 15]

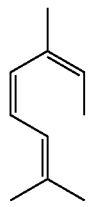

Alloocimene(1)

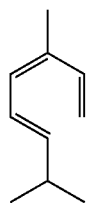

Alloocimene(2)

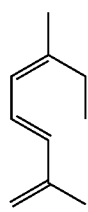

Alloocimene(3)

Therefore, it can be thought that there are the following 24 isomers in the resulting compound A-3 (carboxylic acid). The same shall apply also to the later-described preparation examples of carboxylic acids (AD-4) and (AD-5).

[Compound 16]

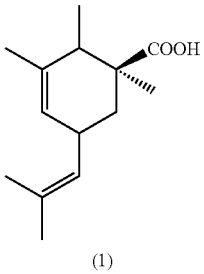 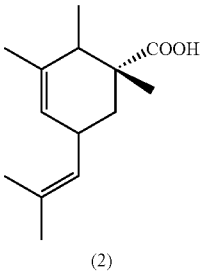

(1) (2)

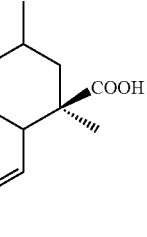 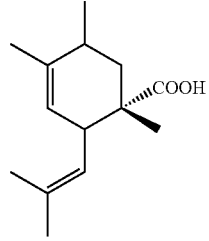

(3) (4)

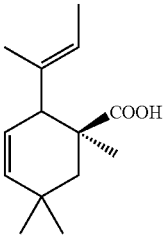 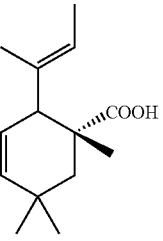

(5) (6)

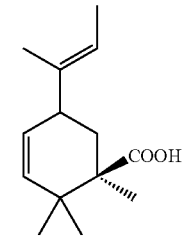 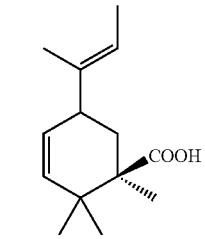

(7) (8)

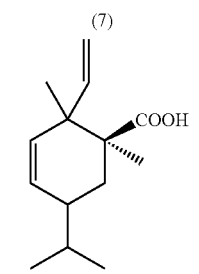 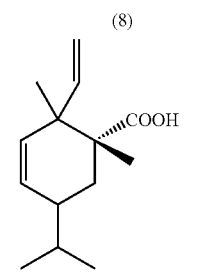

(9) (10)

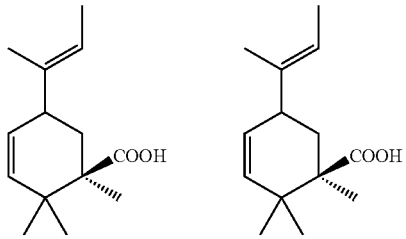

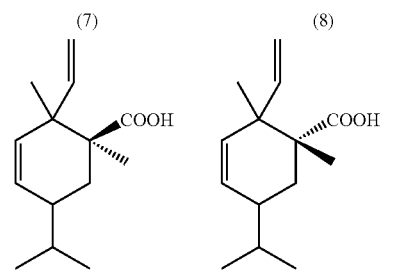

(11) (12)

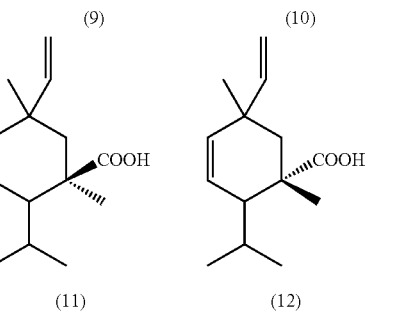

-continued

[Compound 17]

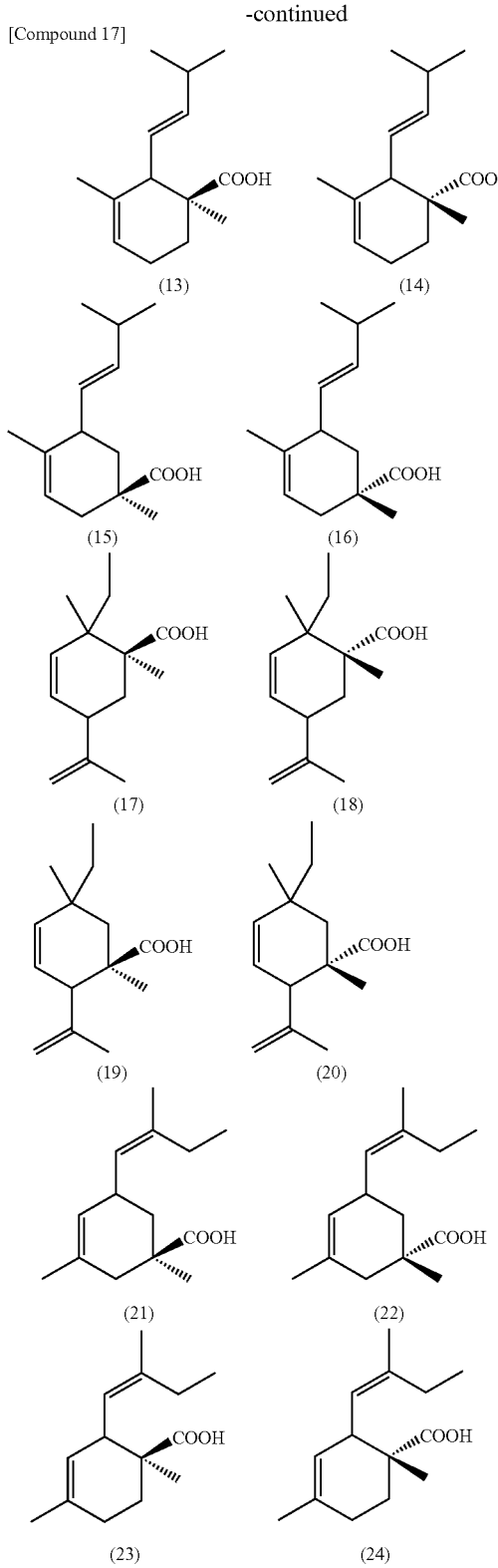

As described above, the compounding agent for an antifouling paint according to the invention comprises one or more substances selected from a cyclic carboxylic acid formed by the addition reaction of an unsaturated carboxylic acid with a conjugated diene compound, a derivative of the cyclic carboxylic acid (except a metal salt), a metal salt of the cyclic carboxylic acid and a metal salt of a derivative of the cyclic carboxylic acid. The cyclic carboxylic acid derivative for constituting the compounding agent for an antifouling paint is, for example, an esterification product, an amidation product, a hydrogenation product, a disproportionation product, a heat treatment product, a vinyl ether addition product, a Michael addition product or a Diels-Alder addition product of the cyclic carboxylic acid.

The esterification product of the cyclic carboxylic acid (cyclic carboxylic acid ester) is specifically an ester formed from the cyclic carboxylic acid and an alcohol of 1 to 18 carbon atoms, preferably 1 to 8 carbon atoms, and examples thereof include hydrocarbon esters of cyclic carboxylic acids, such as alkyl esters and aryl esters of cyclic carboxylic acids.

The amidation product of the cyclic carboxylic acid (cyclic carboxylic acid amide) is specifically an amide formed from the cyclic carboxylic acid and an amine of 1 to 18 carbon atoms, preferably 1 to 8 carbon atoms, and examples thereof include hydrocarbon group-containing amides, such as alkyl amides and aryl amides.

The hydrogenation product of the cyclic carboxylic acid is, for example, a compound obtained by the addition of hydrogen to hydrocarbon double bond in the cyclic carboxylic acid molecule or a compound obtained by cleavage of cyclocarbon ring by the addition of hydrogen in the cyclic carboxylic acid molecule.

The heat treatment product of the cyclic carboxylic acid is, for example, a compound obtained by heat-treating the cyclic carboxylic acid at 250 to 350° C. in an inert gas.

By carrying out such heat treatment, reaction between molecules of the cyclic carboxylic acid sometimes takes place to form a disproportionation product. As a matter of course, such a disproportionation product is employable as the cyclic carboxylic acid derivative of the invention.

The vinyl ether addition product of the cyclic carboxylic acid is a compound wherein one vinyl ether containing a hydrocarbon group such as an alkyl group of 1 to 18 carbon atoms, preferably 1 to 8 carbon atoms, or an aryl group is added to a carboxyl group of the cyclic carboxylic acid. Such a vinyl ether addition product is prepared by utilizing a process disclosed in, for example, Japanese Patent Laid-Open Publication No. 262076/2001.

The Michael addition product of the cyclic carboxylic acid is, for example, a compound formed by the addition reaction of an active methylene compound of 1 to 18 carbon atoms, preferably 1 to 8 carbon atoms, such as malonic acid ester, acetoacetic acid ester or cyanoacetic acid ester, with polarized carbon-carbon double bond in the cyclic carboxylic acid (or ester thereof).

Further, a compound wherein the carboxyl group is added to the double bond of the unsaturated cyclic carboxylic acid by self-Michael addition is also available.

The Diels-Alder addition product of the cyclic carboxylic acid is, for example, a compound formed by the addition of a diene component of 4 to 50 carbon atoms, preferably 4 to 20 carbon atoms, to the hydrocarbon double bond of the cyclic carboxylic acid.

The metal salt of the novel (bi)cycloalkenylcarboxylic acid of the invention is a monocarboxylic acid metal salt obtained by the reaction of a monocarboxylic acid represented by the formula [V] or [VI] with a metal compound, and is generally represented by the formula ($\alpha$): $(RCOO)_xM$ (RCOO is a cyclic carboxylic acid residue, M is a metal atom, and x is a valence of the metal atom).

To the formula ($\alpha$), a ligand such as water, acid or base may be bonded or coordinated, and the metal salt may be a metal salt which is not constituted of a metal and a carboxylic acid (more precisely, carboxyl group in the carboxylic acid) in an equivalent weight ratio (equivalent number of metal/equivalent number of carboxylic acid=1/1), that is, the metal salt may be an excess metal salt of a carboxylic acid in which the amount of the metal is larger than the equivalent weight ratio (equivalent number of metal/equivalent number of carboxylic acid>1/1) or may be a carboxylic acid metal salt in which the amount of the metal is less than the equivalent weight ratio (meaning of the term "excess metal salt of carboxylic acid": see Japanese Patent Laid-Open Publication No. 97406/2002 corresponding to Japanese Patent Application No. 290907/2000 previously proposed by the present applicant).

Examples of the metal salts of the cyclic carboxylic acids and the metal salts of the cyclic carboxylic acid derivatives include metal salts formed by the reaction of the cyclic carboxylic acids or the cyclic carboxylic acid derivatives (except metal salts) with metals, such as zinc, calcium, copper, magnesium, strontium, manganese and nickel, or with metal compounds containing these metals. Of such metal salts, metal salts of zinc or copper are particularly preferable from the viewpoints of coating film erodibility and antifouling property.

The carboxylic acid metal salts can be prepared by various processes publicly known, such as the following double decomposition process, melting process and direct process.

(Double Decomposition Process)

The double decomposition process is a process comprising introducing an aqueous solution of a metal salt (copper sulfate or the like) into a (aqueous) solution of a sodium salt of a carboxylic acid, a potassium salt thereof or the like, performing double decomposition to form a carboxylic acid metal salt and purifying it by solvent extraction or the like.

(Melting Process)

The melting process is a process comprising heating an oxide of a metal, an acetic acid salt thereof, a hydroxide thereof or the like together with a carboxylic acid of a metal carrier to distill off water or an acetic acid and thereby obtain a carboxylic acid metal salt.

In this process, it is possible that the reaction is carried out in an organic solvent, and water or an acetic acid is distilled off by azeotropic distillation or the like, when needed.

(Direct Process)

The direct process is a process comprising allowing a metal itself to directly react with a carboxylic acid to obtain a carboxylic acid metal salt.

The carboxylic acid metal salts mentioned above can be readily prepared also in the course of the production of paint using the carboxylic acids.

For example, the carboxylic acid zinc salt can be readily obtained by mixing zinc white (zinc oxide) with the carboxylic acid.

In this process, the carboxylic acid and zinc white are kneaded by a dispersing method using a disperser or various mills in the presence of a publicly known solvent for paint if necessary to obtain a carboxylic acid zinc salt and then compounding the salt with such various components as added to a paint composition, to prepare a desired paint composition (antifouling paint composition).

If the carboxylic acid and zinc white are present in the compounding ingredients for preparing a paint, a metal salt of the carboxylic acid is formed in the resulting paint.

In the above process, in order to increase a production rate of a metal salt, water may be added, or in order to remove water produced by the reaction or water content added, a dehydrating agent publicly known may be properly used.

The component (A) has excellent compatibility with the later-described copolymer (B) for a self-polishing type antifouling paint, particularly a silyl ester copolymer, and an antifouling paint composition containing the components (A) and (B) exhibits proper elusion into seawater and is excellent in properties such as coating film erosion acceleration property and antifouling performance improving property when a coating film is formed from the composition.

The compounding agent (A) for an antifouling paint is contained in an amount of 0.1 to 300 parts by weight, preferably 1 to 200 parts by weight, more preferably 5 to 100 parts by weight, particularly preferably 5 to 50 parts by weight, based on 100 parts by weight of the hydrolyzable copolymer (B) for a self-polishing type antifouling paint (non-volatile matter) contained in the below-described antifouling paint composition of the invention, particularly a silyl ester-based copolymer (non-volatile matter). When the component (A) is contained in such an amount, hydrolysis rate of a coating film (antifouling coating film, hydrolyzable resin film) formed from the resulting antifouling paint composition is appropriately controlled, and as a result, antifouling performance of the coating film, particularly antifouling performance in the highly fouling sea area or in the static environment, is exhibited over a long period of time, so that such an amount is preferable.

For the same reasons, the compounding agent (A) for an antifouling paint is desirably used in an amount of usually 0.01 to 90 parts by weight, preferably 0.1 to 50 parts by weight, in 100 parts by weight of the antifouling paint composition (except solvent).

<Antifouling Paint Composition>

The antifouling paint composition of the invention comprises the compounding agent (A) (or (AD)) for an antifouling paint and a copolymer (B) for a self-polishing type antifouling paint.

It is preferable that the antifouling paint composition does not substantially contain an antifouling agent which is a large burden to the environment, such as a tin compound, and consequently, a coating film having no evil influence on the environment can be formed. Moreover, the coating film contains the compounding agent (A) for an antifouling paint, which functions as a hydrolysis controlling agent or an elution assistant, so that the hydrolysis rate of the copolymer (B) for a self-polishing type antifouling paint contained in the coating film is favorably controlled, and the erosion rate of the coating film is maintained stable (constant) over a long period of time. Therefore, the elution rate of an antifouling agent is constant and the antifouling agent exhibits excellent controlled releasability. In addition, the antifouling paint composition of the invention has excellent long-term antifouling property and can be preferably applied particularly to ships running in the highly fouling sea area and to underwater structures, fishing tackles and fishing nets used in the static environment.

Copolymer (B) for Self-Polishing Type Antifouling Paint

As the copolymer (B) for a self-polishing type antifouling paint, which is a film-forming component, a polymerizable unsaturated carboxylic acid hydroxy metal salt-based copolymer (B-a) and/or "a polymerizable unsaturated carboxylic acid metal compound-based copolymer (B-b) containing a constituent unit derived from a polymerizable unsaturated carboxylic acid metal compound containing no hydroxyl group (—OH) directly bonded to a metal atom" is employed.

As the former polymerizable unsaturated carboxylic acid hydroxy metal salt-based copolymer (B-a), a (meth)acrylic acid hydroxy metal salt-based copolymer (i) is preferably employed, and as the latter "polymerizable unsaturated carboxylic acid metal compound-based copolymer (B-b) containing a constituent unit derived from a polymerizable unsaturated carboxylic acid metal compound containing no hydroxyl group (—OH) directly bonded to a metal atom", a (meth)acrylic acid metal salt-based copolymer (ii) containing no hydroxyl group bonded to a metal atom is preferably employed.

As the (meth)acrylic acid hydroxy metal salt-based copolymer (i), such a resin Rp-COOM—OH (Rp: base resin, M: zinc atom or copper atom (divalent metal atom)) as described in Japanese Patent Laid-Open Publication No. 209005/1996 or Japanese Patent Laid-Open Publication No. 286933/1997 is employable.

As the copolymer (ii), i.e., the (meth)acrylic acid metal salt-based copolymer (ii) containing no hydroxyl group bonded to a metal atom, a (meth)acrylic acid metal salt-based copolymer described in the paragraphs [0036] to [0049] of Japanese Patent Laid-Open Publication No. 323209/1999 previously proposed by the present applicant or a resin described in the paragraphs [0015] to [0044] of Japanese Patent Laid-Open Publication No. 302572/1999 is employable.

In the present invention, the polymerizable unsaturated carboxylic acid hydroxy metal salt-based copolymer (i) is preferably a copolymer having, in a molecule, a constituent unit derived from a polymerizable unsaturated carboxylic acid hydroxy metal salt represented by the following formula [I]:

R¹—COOM—OH [I]

wherein R¹ is an unsaturated bond-containing organic group of CH₂=C(CH₃)—, CH₂=CH—, HOOC—CH=CH— or HOOC—CH=C(CH₃)—, —COOH may form a metal salt or an ester, and M is a metal atom, such as Zn or Cu.

From the viewpoints of properties of the resulting coating film, the copolymer (i) is more preferably a (meth)acrylic acid hydroxy metal salt-based copolymer having a constituent unit derived from a (meth)acrylic acid hydroxy metal salt, still more preferably a (meth)acrylic acid hydroxy metal salt-based copolymer having a constituent unit derived from a (meth)acrylic acid hydroxy metal salt wherein the metal atom M is zinc (Zn) or copper (Cu), particularly preferably a (meth)acrylic acid hydroxy metal salt-based copolymer having a constituent unit derived from a (meth)acrylic acid hydroxy metal salt wherein M is zinc (Zn).

In the present invention, the (meth)acrylic acid metal salt-based copolymer (ii) containing no hydroxyl group bonded to a metal atom is, for example, a copolymer having, in a molecule, a constituent unit derived from a polymerizable unsaturated carboxylic acid metal compound represented by the following formula [II]:

R¹—COO—M—L_n [II]

wherein R¹ is an unsaturated bond-containing organic group selected from CH₂=C(CH₃)—, CH₂=CH—, HOOC—CH=CH— and HOOC—CH=C(CH₃)—, —COOH may form a metal salt or an ester, M is a metal atom, preferably a metal atom other than Si, L is an organic acid residue —OCOR² (R² is an alkyl group of 1 to 25 carbon atoms, a cycloalkyl group, an aromatic hydrocarbon group, preferably a phenyl group, or an aralkyl group, which may have a substituent; this organic acid residue may be an organic acid residue derived from the novel cycloalkenylcarboxylic acid-based compound [V] or the novel bicyclialkenylcarboxylic acid-based compound [VI] of the invention which is one kind of an organic acid), L may be the same as or different from R¹, and n is a number of "valence of the metal M(−1)".

Further, the copolymer (ii) is more preferably a copolymer containing a constituent unit derived from a (meth)acrylic acid metal compound containing no hydroxyl group bonded to a metal atom, and is particularly preferably a copolymer having Zn or Cu as the metal atom M and containing a constituent unit derived from a (meth)acrylic acid zinc salt or copper salt containing no hydroxyl group bonded to the zinc or copper atom.

The copolymer (B) for a self-polishing type antifouling paint for use in the invention, preferably a (meth)acrylic acid metal salt-based copolymer, has long-term slight water-solubility as a vehicle component and has a function of imparting long-term antifouling property to the coating film. Such a (meth)acrylic acid metal compound-based copolymer is, for example, a copolymer which is obtained by copolymerizing a (meth)acrylic acid metal compound (a) (polymerizable monomer) and "another monomer" (b) copolymerizable with the metal compound (a) (monomer (a)) and contains constituent units derived from the (meth)acrylic acid metal compound (a) in amounts of usually 0.01 to 99.99% by weight, preferably 2 to 50% by weight, and constituent units derived from the another monomer (b) copolymerizable with the monomer (a) in the residual amounts, i.e., 99.99 to 0.01% by weight, preferably 98 to 50% by weight ((a)+(b)=100% by weight).

In the present invention, the term "-based" used in expressions such as "(meth)acrylic acid metal compound-based copolymer" and "polymerizable unsaturated carboxylic acid hydroxy metal salt-based copolymer" means that in the preparation of the copolymer, the substance immediately before "-based" (e.g., (meth)acrylic acid metal compound in case of (meth)acarylic acid metal compound-based) or its analogous compound such as its derivative is used as an essential ingredient, but it is not always restricted to a case where the substance is used in the largest amount among the components used or in an amount of not less than 50%.

Examples of the metals M for constituting the (meth)acrylic acid metal compound include metals of Groups Ib, IIa, IIb, IIIa, IIIb, IVa, IVb, Va, Vb, VIb, VIIb and VIII of the periodic table, specifically divalent or higher metals, such as Cu, Zn, Ni, Co, Pb, Al, Sn and Mg. Of these, Cu and Zn are preferable.

The (meth)acrylic acid metal compound (a) is a salt, an ester or a complex.

Polymerizable Unsaturated Carboxylic Acid Metal Salt-Based Copolymer (B1)

When M in the formula (II) is a metal atom other than Si, such as Cu, Zn or Mg, the (meth)acrylic acid metal compound (monomer) is represented by the following formula (B-II).

R¹—COO—M—L_n (B-II)

In the formula (B-II), R¹, M, L and n are basically the same as those in the formula [II]. Particularly in this formula (B-II), R¹ is the same organic group as in the formula [II], M is the aforesaid metal atom other than Si, such as Cu, Zn or Mg, L is the aforesaid organic acid which may be the same or different from R¹, preferably the aforesaid carboxylic acid residue (—OCOR²), and n is the same as above.

When L in the formula (B-II) is a carboxylic acid residue (—OCOR²), the carboxylic acid (HOCOR²) from which such a group can be derived may be a chain carboxylic acid or may have an alicylic or aromatic ring, and examples thereof include monovalent carboxylic acids, such as propionic acid, valeric acid, oleic acid, linoleic acid, linolenic acid, stearic acid, versatic acid, abietic acid (acid contained in rosin), naphthenic acid, (meth)acrylic acid, benzoic acid, the novel cycloalkenylcarboxylic acid-based compound [V] of the invention and the novel bicycloalkenylcarboxylic acid-based compound [VI] of the invention.

Examples of the (meth)acrylic acid metal compounds represented by the formula (B-II) include zinc methacrylate [(CH$_2$=C(CH$_3$)—COO—)$_2$Zn], zinc acrylate [(CH$_2$=CH—COO—)$_2$Zn], magnesium methacrylate [(CH$_2$=C(CH$_3$)—COO—)$_2$Mg], magnesium acrylate [(CH$_2$=CH—COO—)$_2$Mg], copper methacrylate [(CH$_2$=C(CH$_3$)—COO—)$_2$Cu], copper acrylate [(CH$_2$=CH—COO—)$_2$Cu], zinc versatate methacrylate [(CH$_2$=C(CH$_3$)—COO—)((C$_3$H$_7$)$_3$C—COO—)Zn], zinc versatate acrylate [(CH$_2$=CH—COO—)((C$_3$H$_7$)$_3$C—COO—)Zn], zinc naphthenate methacrylate [(CH$_2$=C(CH$_3$)—COO—) (naphthenic acid residue)Zn], zinc naphthenate acrylate [(CH$_2$=CH—COO—)(naphthenic acid residue)Zn], zinc benzoate methacrylate [(CH$_2$=C(CH$_3$)—COO—)((C$_6$H$_5$)COO—)Zn], zinc benzoate acrylate [(CH$_2$=CH—COO—)((C$_6$H$_5$)COO—)Zn], magnesium benzoate methacrylate [(CH$_2$=C(CH$_3$)—COO—)((C$_6$H$_5$)COO—)Mg], magnesium versatate acrylate [(CH$_2$=CH—COO—)((C$_3$H$_7$)$_3$C—COO—)Mg], copper versatate methacrylate [(CH$_2$=C(CH$_3$)—COO—)((C$_3$H$_7$)$_3$C—COO—)Cu], copper benzoate methacrylate [(CH$_2$=C(CH$_3$)—COO—)((C$_6$H$_5$)COO—)Cu], copper naphthenate methacrylate [(CH$_2$=C(CH$_3$)—COO—)(naphthenic acid residue)Cu], copper naphthenate acrylate [(CH$_2$=CH—COO—)(naphthenic acid residue)Cu], and hydrates thereof.

The "another monomer (b)" copolymerizable with the (meth)acrylic acid metal compound (a) may be any of aliphatic type, alicyclic type and aromatic type and is, for example, a (meth)acrylic acid ester or a vinyl monomer having a hydroxyl group and/or an amino group.

Examples of the (meth)acrylic acid esters employable as the "another monomer (b)" include monomers of aliphatic type, such as methyl (meth)acrylate, ethyl (meth)acrylate, n-propyl (meth)acrylate, i-propyl (meth)acrylate, n-butyl (meth)acrylate, i-butyl (meth)acrylate, t-butyl (meth)acrylate, 2-ethylhexyl (meth)acrylate, lauryl (meth)acrylate, stearyl (meth)acrylate, glycidyl (meth)acrylate and 2-methoxyethyl (meth)acrylate; monomers of alicyclic type, such as cyclohexyl (meth)acrylate and isobornyl (meth)acrylate; and monomers of aromatic type, such as phenyl (meth)acrylate and benzyl (meth)acrylate.

The vinyl monomer (b) having a hydroxyl group and/or an amino group employable as the "another monomer (b)" copolymerizable with the (meth)acrylic acid metal compound (a) has only to have any one of a hydroxyl group and an amino group, and may be a monomer, a dimer, a trimer or the like, and examples thereof include compounds having one hydroxyl group, such as 2-hydroxyethyl (meth)acrylate, 2-hydroxypropyl (meth)acrylate, 3-hydroxypropyl (meth)acrylate and 2-hydroxybutyl (meth)acrylate. Further, adducts of 2-hydroxyethyl (meth)acrylate with ethylene oxide, propylene oxide, γ-butyrolactone, ε-caprolactone and the like; dimers or trimers, such as 2-hydroxyethyl (meth)acrylate and 2-hydroxypropyl (meth)acrylate; monomers having plural hydroxyl groups, such as glycerol (meth)acrylate; etc. are also employable.

The monomer (b) having an amino group may be any one of primary to tertiary monomers, and examples thereof include primary to secondary amino group-containing monomers, such as (meth)acrylamide and butylaminoethyl (meth)acrylate; and dimethylaminoethyl (meth)acrylate, diethylaminoethyl (meth)acrylate, dimethylaminopropyl (meth)acrylate, dimethylaminobutyl (meth)acrylate, dibutylaminoethyl (meth)acrylate, dimethylaminoethyl (meth)acrylamide and dimethylaminopropyl (meth)acrylamide. Further, heterocyclic basic monomers, such as vinylpyrrolidone, vinylpyridine and vinylcarbazole, are also employable.

Moreover, carboxylic acids, such as (meth)acrylic acid, itaconic acid, maleic acid and succinic acid, esters derived from these carboxylic acids, styrene, vinyltoluene, α-methylstyrene, (meth)acrylonitrile, vinyl acetate, vinyl propionate, etc. are also employable.

The (meth)acrylic acid metal compound (monomer (a)) and the "another monomer (b)" can be each used singly or in combination of two or more kinds.

The monomers (a) and (b) are copolymerized at the carbon-carbon unsaturated bond site to form a (meth)acrylic acid metal compound-based copolymer. In the copolymer, constituent units (a) and (b) derived from these monomers (a) and (b) may be arranged at random or blockwise, but they are often arranged at random.

The (meth)acrylic acid metal compound-based copolymer obtained by copolymerizing such monomers (a) and (b) has a weight-average molecular weight (Mw) of usually about 1,000 to 100,000 and a glass transition temperature Tg of about −20° C. to +100° C.

In the antifouling paint composition, the (meth)acrylic acid metal compound-based copolymer is preferably contained as a resin solid content in an amount of usually 1 to 99% by weight, preferably 10 to 70% by weight, more preferably 15 to 50% by weight. When the (meth)acrylic acid metal compound-based copolymer is contained in such an amount in the antifouling paint composition, the composition exerts satisfactory antifouling effect and exhibits persisting erodibility, so that such an amount is preferable.

It is desirable that the (meth)acrylic acid metal compound-based copolymer is contained in an amount of usually 1 to 99 parts by weight, preferably 10 to 70 parts by weight, based on the total 100 parts by weight of the components of the antifouling paint composition except a solvent. When the (meth)acrylic acid metal compound-based copolymer is contained in such an amount in the antifouling paint composition, the surface of the coating film tends to have excellent stable erodibility and antifouling property for a long period of time.

The (meth)acrylic acid metal compound-based copolymer can be readily prepared in accordance with or by making reference to the processes disclosed in, for example, Japanese Patent Publication No. 64985/1995, Japanese Patent Laid-Open Publication No. 80205/1992, Japanese Patent Laid-Open Publication No. 80269/1992, Japanese Patent Laid-Open Publication No. 80270/1992, Japanese Patent Laid-Open Publication No. 128008/1988, Japanese Patent Laid-Open Publication No. 128084/1988, Japanese Patent Laid-Open Publication No. 16809/1989, Japanese Patent Laid-Open Publication No. 171066/1993, Japanese Patent Laid-Open Publication No. 158547/1998 and Japanese Patent Laid-Open Publication No. 302572/1999. The (meth)acrylic acid metal compound-based copolymer can be prepared by, for example, any one of the following processes (1) to (4).

(1) In a first process, a (meth)acrylic acid metal compound (a) (monomer (a)) and another monomer (b) copolymerizable with the metal compound (monomer (a)), such as 2-methoxyethyl (meth)acrylate or methyl (meth)acrylate, are mixed with an organic solvent, and they are subjected to solution polymerization at a temperature of 60 to 180° C. for 5 to 14 hours in the presence of a radical polymerization initiator, such as t-butyl peroxyoctoate or azobisisobutyronitile (AIBN), whereby the copolymer can be formed.

(2) In a second process, a (meth)acrylic acid metal compound (a-1), another monomer (b) copolymerizable with the monomer (a-1), and a saturated aliphatic carboxylic acid metal compound or a saturated alicyclic carboxylic acid metal compound or an aromatic carboxylic acid metal compound are mixed with an organic solvent, and they are subjected to solution polymerization at a temperature of 60 to 180° C. for 5 to 14 hours in the presence of a radical polymerization initiator, such as t-butyl peroxyoctoate or azobisisobutyronitile (AIBN), whereby the copolymer can be formed.

(3) In a third process, an unsaturated double bond-containing carboxylic acid (a-1), such as (meth)acrylic acid, and another monomer (b) copolymerizable with the monomer (a-1) are mixed with an organic solvent, and they are subjected to solution polymerization at a temperature of 60 to 180° C. for 5 to 14 hours in the presence of a radical polymerization initiator, such as t-butyl peroxyoctoate or azobisisobutyronitile (AIBN), to form a copolymer having at the side chain end a carboxyl group derived from the unsaturated double bond-containing carboxylic acid (a-1).

Subsequently, the resulting copolymer, a carboxylic acid metal compound capable of introducing a metal atom M such as copper (Cu) into the carboxyl group of the copolymer, e.g., copper acetate, a carboxylic acid (HOCOR$^2$, R$^2$: the same as above) bonded to the metal atom M and capable of introducing an end group (L) such as a carboxylic acid residue (—OCOR$^2$, R$^2$: the same as above) into the side chain end, e.g., propionic acid, valeric acid, oleic acid or linoleic acid, and water (pure water) are placed in a reactor, then they are reacted at a temperature of 60 to 180° C. for 1 to 10 hours, and thereafter, the temperature is raised to 120 to 140° C. to separate and remove acetic acid or the like produced as a by-product, whereby a hydrolyzable (meth)acrylic acid metal compound-based copolymer in which —COO—M—L$_n$ (M, L$_n$: the same as above) is introduced into the side chain is obtained.

(4) In a fourth process, an unsaturated double bond-containing carboxylic acid (a-1), such as (meth)acrylic acid, and another monomer (b) copolymerizable with the monomer (a-1) are mixed with an organic solvent, and they are subjected to polymerization in the presence of a radical polymerization initiator, such as t-butyl peroxyoctoate or AIBN, to form a copolymer having at the side chain end a carboxyl group derived from the unsaturated double bond-containing carboxylic acid (a-1), similarly to the third process.

Subsequently, the resulting copolymer, a metal oxide capable of introducing a metal atom M such as zinc (Zn) into the carboxyl group of the copolymer, e.g., zinc oxide (zinc white), a carboxylic bonded to the metal atom M and capable of introducing an end group (L) such as a carboxylic acid residue into the side chain end, e.g., propionic acid, valeric acid, oleic acid or linoleic acid, and water are placed in a reactor, then they are reacted at a temperature of 60 to 180° C. for 1 to 10 hours, and thereafter, the temperature is raised to 110 to 120° C. to separate and remove reaction water or the like produced as a by-product, whereby a hydrolyzable (meth)acrylic acid metal compound-based copolymer in which —COO—M—L$_n$ (M, L$_n$: the same as above) is introduced into the side chain is obtained.

Polymerizable Unsaturated Carboxylic Acid Silyl Ester-Based Copolymer (B2)

Next, a case where the copolymer (B) is a polymerizable unsaturated carboxylic acid silyl ester-based copolymer is described.

When M is Si as described above, n in the formula [II] becomes 3, and in this case, the copolymer becomes a polymerizable unsaturated carboxylic acid silyl ester (monomer) represented by the following formula (B-12):

$$R^1\text{—COO—Si—L}_3 \qquad (B\text{-}12)$$

wherein R$^1$ is the same organic group as in the formula [II], and each L may be the same or different and is any one of a chain alkyl group of 1 to 25 carbon atoms, preferably 1 to 20 carbon atoms, more preferably 1 to 10 carbon atoms, which may have a branch, a cycloalkyl group, an aromatic hydrocarbon group, preferably a phenyl group, and an alkylsilyloxy group wherein the alkyl group is the same as above, each of which may have a substituent.

Therefore, the polymerizable unsaturated carboxylic acid silyl ester-based copolymer is a copolymer having, in a molecule, a constituent unit derived from the polymerizable unsaturated carboxylic acid silyl ester.

That is to say, R$^1$ is an unsaturated bond-containing organic group represented by CH$_2$=C(CH$_3$)—, CH$_2$=CH—, HOOC—CH=CH— or HOOC—CH=C(CH$_3$)—, and —COOH may form a metal salt or an ester.

Three of L, namely, L$^1$, L$^2$ and L$^3$ may be the same as or different from one another and are each a hydrogen atom or any one of a chain alkyl group of 1 to 25 carbon atoms, preferably 1 to 20 carbon atoms, more preferably 1 to 10 carbon atoms, which may have a branch, a cycloalkyl group, an aromatic hydrocarbon group, preferably a phenyl group, and an alkylsilyloxy group wherein the alkyl group is the same as above, each of which may have a substituent.

It is preferable that L$^1$, L$^2$ and L$^3$ may be the same as or different from one another and are each any one of a chain alkyl group of 1 to 25 carbon atoms, preferably 1 to 20 carbon atoms, more preferably 1 to 18 carbon atoms, still more preferably 1 to 10 carbon atoms, particularly preferably 1 to 6 carbon atoms, which may have a branch, a cycloalkyl group of preferably 3 to 10 carbon atoms, more preferably 3 to 8 carbon atoms, and a phenyl group which may have a substituent. These L may be the same or different from R$^1$.

Such a copolymer (B) is a copolymer having, in a molecule, a constituent unit derived from a silyl unsaturated carboxylate monomer represented by the following formula [IIIA] and a constituent unit derived from an unsaturated monomer copolymerizable with the silyl unsaturated carboxylate monomer.

$$R^1\text{—COO—Si}(L^1L^2L^3) \qquad [\text{IIIA}]$$

In the formula [IIIA], R$^1$, L, L$^2$ and L$^3$ are the same as above, and three of L, namely, L$^1$, L$^2$ and L$^3$ are the same as R$^{12}$, R$^{13}$ and R$^{14}$ in the below-described formula [III], respectively.

The polymerizable unsaturated carboxylic acid silyl ester-based copolymer (B2) (also referred to as a "silyl ester compound") containing a constituent unit derived from the polymerizable unsaturated carboxylic acid silyl ester (B-12) is described below in detail.

The silyl ester compound (B2) for use in the invention contains a constituent unit derived from the polymerizable unsaturated carboxylic acid silyl ester.

(a) Constituent Unit Derived from Polymerizable Unsaturated Carboxylic Acid Silyl Ester Examples of the polymerizable unsaturated carboxylic acid silyl esters include silyl esters of unsaturated monocarboxylic acids such as acrylic acid and methacrylic acid, silyl esters of α,β-unsaturated dicarboxylic acids such as itaconic acid, maleic acid, fumaric acid and citraco-dibasic acid, and silyl esters which are half esters of α,α-unsaturated dicarboxylic acids.

The constituent unit derived from the polymerizable unsaturated carboxylic acid silyl ester is preferably a silyl (meth)acrylate constituent unit represented by the following formula [III]:

[Compound 18]

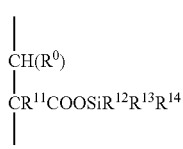

[III]

wherein $R^0$ is a hydrogen atom or —COOH, preferably a hydrogen atom (H), —COOH may form a metal salt or an ester, $R^{11}$ is a hydrogen atom or a methyl group, and $R^{12}$, $R^{13}$ and $R^{14}$ may be the same or different and are each a hydrogen atom, an alkyl group of the same number of carbon atoms as previously mentioned (i.e., chain alkyl group of 1 to 25 carbon atoms, preferably 1 to 20 carbon atoms, more preferably 1 to 18 carbon atoms, still more preferably 1 to 10 carbon atoms, particularly preferably 1 to 6 carbon atoms, which may have a branch), a cycloalkyl group of the same number of carbon atoms as previously mentioned (i.e., cycloalkyl group of preferably 3 to 10 carbon atoms, more preferably 3 to 8 carbon atoms), an aromatic hydrocarbon group of 6 to 12 carbon atoms which may have a substituent, preferably a phenyl group, or an alkylsilyloxy group wherein the alkyl group has the same number of carbon atoms as mentioned above.

Examples of the substituents with which a hydrogen atom of the aromatic hydrocarbon group such as a phenyl group can be replaced include alkyl, aryl and halogen.

The silyl (meth)acrylate(s) from which such silyl (meth)acrylate (type) consitituent unit can be derived is represented by the following formula (III-a0):

Formula (III-a0):

[Compound 19]

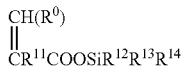

[III-a0]

wherein $R^0$ is the same as $R^0$ in the formula [III] and is a hydrogen atom or —COOH, preferably a hydrogen atom (H), $R^{11}$ is the same as $R^{11}$ in the formula [III] and is a hydrogen atom or a methyl group, and $R^{12}$, $R^{13}$ and $R^{14}$ are the same as $R^{12}$, $R^{13}$ and $R^{14}$ in the formula [III], may be the same or different and are each the same hydrogen atom, alkyl group, cycloalkyl group, phenyl group which may have a substituent or alkylsilyloxy group as mentioned above.

Examples of the silyl (meth)acrylates (III-a0) include silyl (meth)acrylates wherein $R^{12}$, $R^{13}$ and $R^{14}$ are the same as one another, such as trimethylsilyl (meth)acrylate, triethylsilyl (meth)acrylate, tripropylsilyl (meth)acrylate, triisopropylsilyl (meth)acrylate, tributylsilyl (meth)acrylate, tri-sec-butylsilyl (meth)acrylate and triisobutylsilyl (meth)acrylate; and silyl (meth)acrylates wherein $R^{12}$, $R^{13}$ and $R^{14}$ are partially or completely different from one another, such as di-sec-butylmethylsilyl (meth)acrylate, sec-butyldimethylsilyl (meth)acrylate, dimethylpropylsilyl (meth)acrylate, monomethyldipropylsilyl (meth)acrylate and methylethylpropylsilyl (meth)acrylate.

The above silyl (meth)acrylates can be used in combination.

Of such silyl (meth)acrylates, preferable are those wherein $R^{12}$, $R^{13}$ and $R^{14}$ are each independently an alkyl group of about 1 to 18 carbon atoms, such as methyl, ethyl, n-propyl, isopropyl, sec-butyl, tert-butyl or isobutyl, and more preferable are those wherein $R^{12}$ is a branched alkyl group or a cycloalkyl group. $R^{13}$ and $R^{14}$ may be each the same as $R^{12}$. Also preferable are those wherein the total number of carbon atoms of $R^{12}$, $R^{13}$ and $R^{14}$ is about 5 to 21. Of such silyl (meth)acrylates, triisopropylsilyl (meth)acrylate, trisobutylsilyl (meth)acrylate, di-sec-butylmethylsilyl (meth)acrylate, sec-butyldimethylsilyl (meth)acrylate and tri-sec-butylsilyl (meth)acrylate are most preferably employed, taking into consideration ease of preparation of the silyl (meth)acrylate copolymer and film-forming property, storage stability and ease of control of self-polishing property of an antifouling paint composition comprising the silyl (meth)acrylate copolymer.

(b) Constituent Unit Derived from Polar Group-Containing (Meth)Acrylate

In the present invention, (b) a constituent unit derived from polar group-containing (meth)acrylate is desirably contained together with the constituent unit (a) derived from the polymerizable unsaturated carboxylic acid silyl ester. The constituent unit (b) does not have to be necessarily contained in the silyl ester copolymer.

The constituent unit derived from polar group-containing (meth)acrylate is not specifically restricted provided that it is a constituent unit derived from a (meth)acrylate-based monomer having a polar group, but preferable is a constituent unit represented by the following formula [IV]:

[Compound 20]

[IV]

wherein $R^0$ is a hydrogen atom or —COOH, preferably a hydrogen atom (H), $R^{15}$ is a hydrogen atom or a methyl group, Z is an oxygen atom or —$NR^{17}$, when Z is an oxygen atom, $R^{16}$ is a hydroxyalkyl group which may have a substituent, a hydroxycycloalkyl group, a polyalkylene glycol group represented by the formula —$(R^{18}O)_nH$ ($R^{18}$ is an alkylene group, and n is an integer of 2 to 50) or an alkoxypolyalkylene glycol group represented by the formula —$(R^xO)_nR^y$ ($R^x$ is an alkylene group, $R^y$ is an alkyl group, and n is an integer of 1 to 100), and when Z is —$NR^{17}$, $R^{17}$ is an alkyl group which may be substituted with any one of a halogen, a hydroxyl group, an amino group, a substituted amino group, an acyl group and an alkoxy group, and $R^{16}$ is a hydrogen atom.

In the formula [IV], the number of carbon atoms of the hydroxyalkyl group is preferably 1 to 18, more preferably 2 to 9, and the number of carbon atoms of the hydroxycycloalkyl group is preferably 3 to 10, more preferably 3 to 8. The number of carbon atoms of the alkylene group in the polyalkylene glycol group is preferably 1 to 8, more preferably 2 to 4. The number of carbon atoms of the alkylene group in the alkoxypolyalkylene glycol group is preferably 1 to 8, more preferably 2 to 4. The number of carbon atoms of the alkyl group is preferably 1 to 8, more preferably 2 to 4, and this alkyl group may form a cyclic structure. The substituted amino group is, for example, a mono- or dialkylamino group of 1 to 6 carbon atoms, and the acyl group is, for example, an alkanoyl group of 1 to 6 carbon atoms or an alkoxy group of 1 to 6 carbon atoms.

The unsaturated monomer from which the unsaturated monomer constituent unit (b) can be derived is represented by the following formula (IV-a):

[Compound 21]

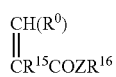

[IV-a]

wherein $R^0$ is a hydrogen atom or —COOH, preferably a hydrogen atom (H), $R^{15}$ is the same as $R^{15}$ in the formula [IV] and is a hydrogen atom or a methyl group, Z is the same as Z in the formula [IV] and is an oxygen atom or —$NR^{17}$, when Z is an oxygen atom, $R^{16}$ is a hydroxyalkyl group which may have a substituent, a hydroxycycloalkyl group, a polyalkylene glycol group represented by the formula —$(R^{18}O)_nH$ ($R^{18}$ is an alkylene group, and n is an integer of 2 to 50) or an alkoxypolyalkylene glycol group represented by the formula —$(R^xO)_nR^y$ ($R^x$ is an alkylene group, $R^y$ is an alkyl group, and n is an integer of 1 to 100), and when Z is —$NR^{17}$, $R^{17}$ is an alkyl group which may be substituted with any one of a halogen, a hydroxyl group, an amino group, a substituted amino group, an acyl group and an alkoxy group, and $R^{16}$ is a hydrogen atom.

In the case where Z in the formula (IV-a) is an oxygen atom, examples of the unsaturated monomers (IV-a) include 2-hydroxyethyl acrylate, 2-hydroxyethyl methacrylate, 2-hydroxypropyl acrylate, 2-hydroxypropyl methacrylate, 3-chloro-2-hydroxypropyl methacrylate, 3-phenoxy-2-hydroxypropyl acrylate, 4-hydroxybutyl acrylate, 2-hydroxybutyl acrylate, 2-hydroxybutyl methacrylate, 6-hydroxyhexyl acrylate, 1,4-cyclohexanedimethanol monoacrylate, polyethylene glycol monomethacrylate (n=2), polyethylene glycol monomethacrylate (n=4), polyethylene glycol monomethacrylate (n=5), polyethylene glycol monomethacrylate (n=8), polyethylene glycol monomethacrylate (n=10), polyethylene glycol monomethacrylate (n=15), polypropylene glycol monomethacrylate (n=5), polypropylene glycol monomethacrylate (n=9), polypropylene glycol monomethacrylate (n=12), 2-methoxyethyl acrylate and methoxypolyethylene glycol monomethacrylate (n=45).

In the case where Z in formula (IV-a) is —$NR^{17}$ examples of such monomers include N-methylolacrylamide, N-methoxymethylacrylamide, N-ethoxymethylacrylamide, N,N-dimethylaminopropylacrylamide, N,N-dimethylaminopropyl methacrylamide, diacetone acrylamide.

These unsaturated monomers (IV-a) can be used singly or in combination of two or more kinds.

Of these unsaturated monomers (IV-a), hydroxyl group-containing monomers are preferable. Of the hydroxyl group-containing monomers, 2-hydroxypropyl acrylate, 2-hydroxybutyl methacrylate and the like are preferably used because an antifouling coating film having appropriate elution property can be obtained.

(c) Unsaturated Monomer Constituent Unit

The silyl ester copolymer usually contains an unsaturated monomer constituent unit (c) in addition to the constituent unit (a) and the constituent unit (b). The unsaturated monomer constituent unit (c) is a constituent unit different from both the constituent units (a) and (b).

Examples of unsaturated monomers (c-1) from which the unsaturated monomer constituent unit (c) can be derived include:

(meth)acrylic acid esters, such as methyl (meth)acrylate, ethyl (meth)acrylate and octyl (meth)acrylate;

styrenes, such as styrene, vinyltoluene and α-methylstyrene;

vinyl esters, such as vinyl acetate, vinyl benzoate, vinyl propionate and vinyl butyrate; and crotonic acid esters, itaconic acid esters, fumaric acid esters and maleic acid esters. Of these, (meth)acrylic acid esters, styrenes and vinyl esters are preferable because an antifouling coating film having proper film strength is obtained.

The above unsaturated monomers are used singly or in combination.

In the present invention, it is desirable that in the silyl ester copolymer (B2), the polymerizable unsaturated carboxylic acid silyl ester constituent units (a) are contained in amounts of 20 to 80% by weight, preferably 30 to 70% by weight, the polar group-containing (meth)acrylate constituent units (b) are contained in amounts of 0 to 40% by weight, preferably 0.01 to 20% by weight, and the other unsaturated monomer constituent units (c) are contained in amounts of 5 to 80% by weight, preferably 10 to 60% by weight ((a)+(b)+(c)=100% by weight), from the viewpoints of coating film strength and erodibility.

The weight-average molecular weight (Mw) of the silyl ester copolymer (B2), as measured by gel permeation chromatography (GPC), is desired to be not more than 200,000, preferably 5,000 to 100,000, from the viewpoints of ease of preparation of an antifouling paint containing the silyl ester copolymer (B2), storage stability and painting workability of the resulting antifouling paint, and erosion rate and crack resistance of an antifouling coating film.

Preparation of Silyl Ester Copolymer (B2)

In order to obtain the silyl (meth)acrylate copolymer (B2), 20 to 80% by weight of the silyl (meth)acrylate (a1) represented by the formula (III-a0), 0 to 40% by weight of the unsaturated monomer (b1) represented by the formula (IV-a) and 5 to 80% by weight of another unsaturated monomer (c1) copolymerizable with the monomer (III-a0) and the monomer (IV-a) ((a1)+(b1)+(c1)=100% by weight) have only to be random-copolymerized by various processes, such as solution polymerization, bulk polymerization, emulsion polymerization and suspension polymerization, in the presence of a radical polymerization initiator. In the polymerization, a chain transfer agent may be employed.

As the radical polymerization initiator, hitherto known azo compounds, peroxides, etc. can be widely employed. Examples of the azo compounds include 2,2'-azobisisobutyronitrile, 2,2'-azobis(2-methylbutyronitrile) and 2,2'-azobis (2,4-dimethylvaleronitrile). Examples of the peroxides include benzoyl peroxide, tert-butyl peroxyacetate, tert-butyl peroxyoctoate, cumene hydroperoxide, tert-butyl peroxide, tert-butyl peroxybenzoate, tert-butyl peroxyisopropyl carbonate, tert-butyl hydroperoxide and persulfuric acid salts (potassium salt, ammonium salt).

As the chain transfer agent, a hitherto known compound is employable, and examples thereof include the following mercapto compounds described in the paragraphs [0077] to [0086] of Japanese Patent Laid-Open Publication No. 206069/2002.

[Compound 22]
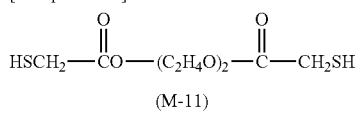
(M-11)
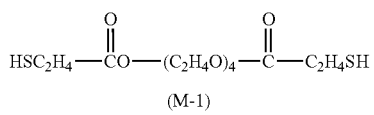
(M-1)
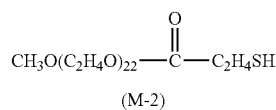
(M-2)
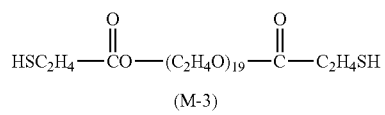
(M-3)
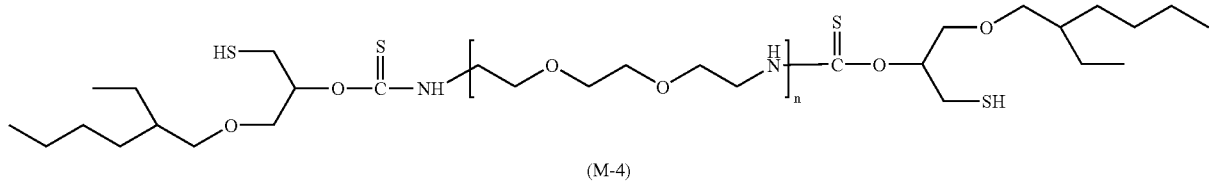
(M-4)
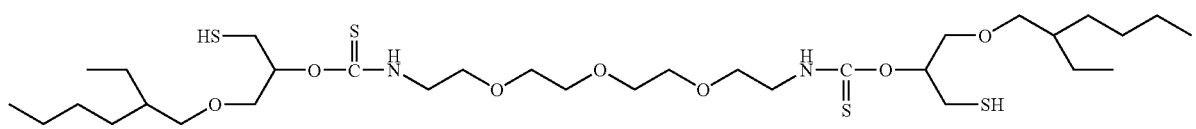
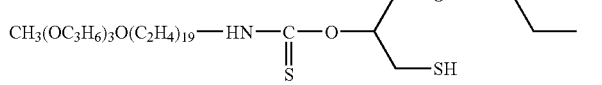
(M-6)
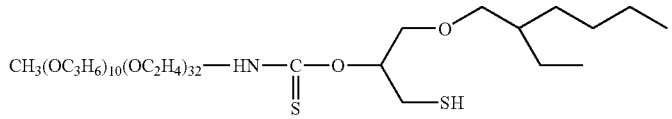
(M-7)
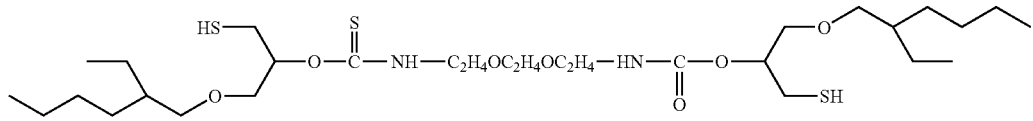
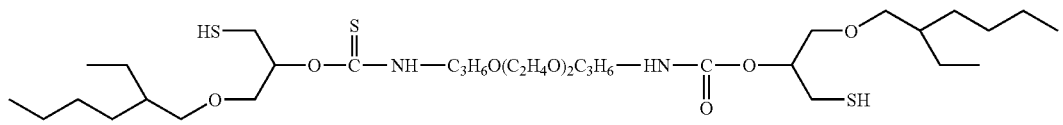
(M-10)
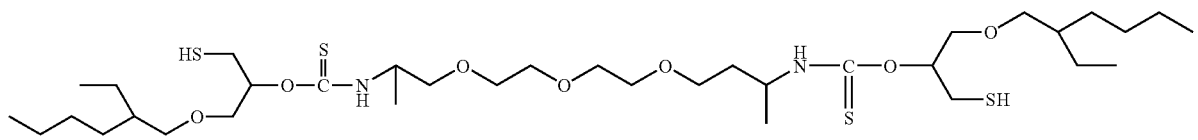
$CH_3OC_2H_4OCCH_2SH$    $CH_3O(C_2H_4O)_{10}(C_3H_6O)_5CCH_2SH$    $HSC_2H_4CO(C_3H_6O)_{10}CC_2H_4SH$
    $\|$                                            $\|$                                      $\|$       $\|$
    O                                           O                               O     O
[Compound 23]
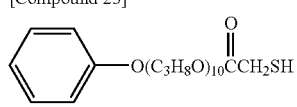
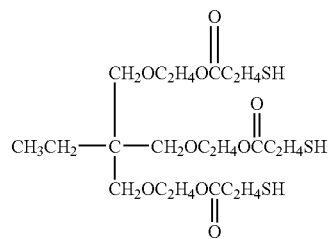

-continued

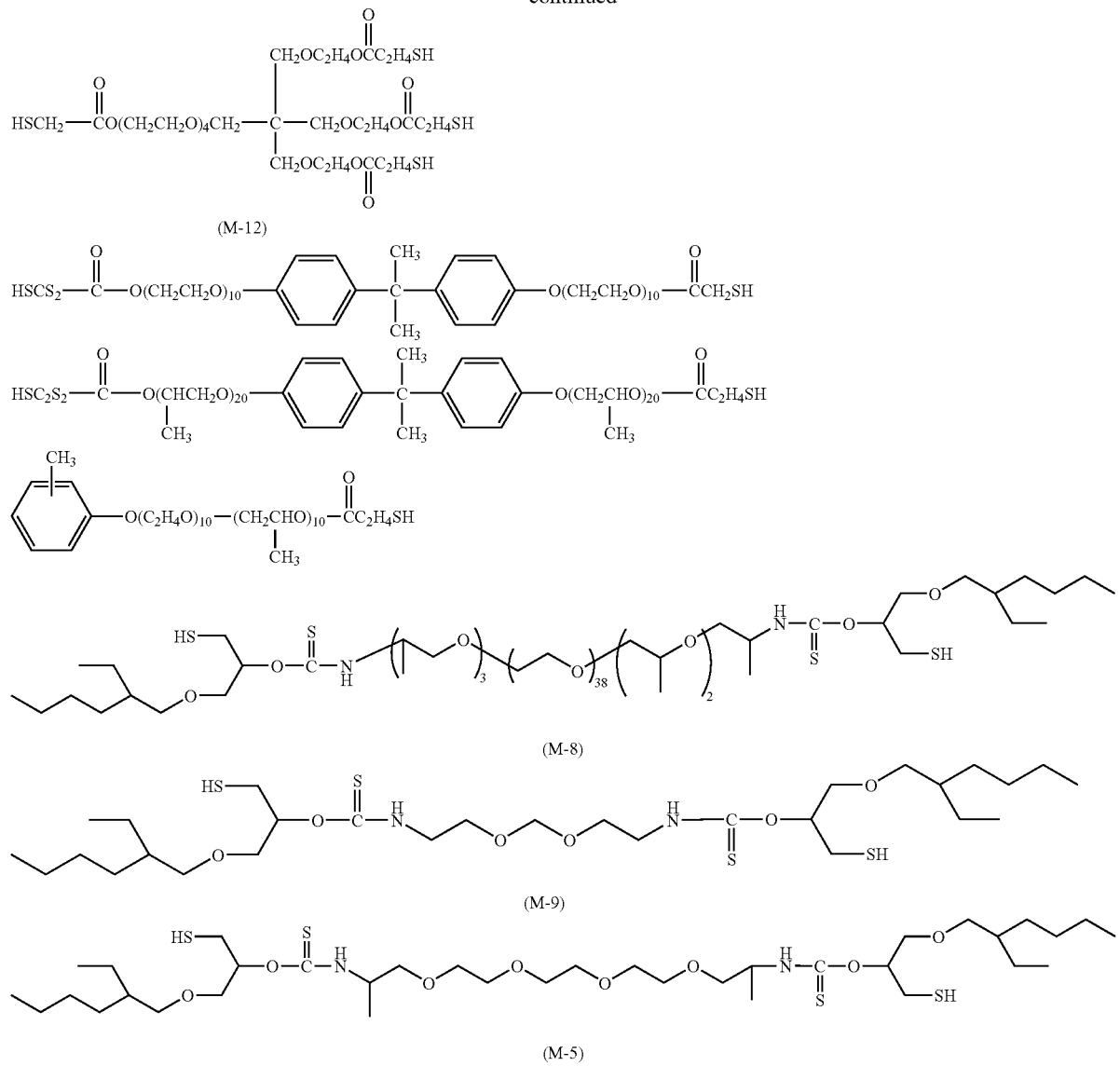

In the later-described Preparation Example (S-8) of a polymer (copolymer), the chain transfer agent represented by the above formula (M-1) (poly(n=4) ethylene glycol bis(3-mercaptopropionate) was used.

In the case where the above polymer is used in an antifouling paint, the solution polymerization process or the bulk polymerization process wherein the polymerization is carried out in an organic solvent is preferable among the aforesaid various polymerization processes. Examples of the organic solvents used in the solution polymerization include:

aromatic hydrocarbons, such as xylene and toluene;
aliphatic hydrocarbons, such as hexane and heptane;
esters, such as ethyl acetate and butyl acetate;
alcohols, such as isopropyl alcohol and butyl alcohol;
ethers, such as dioxane and diethyl ether; and ketones, such as methyl ethyl ketone and methyl isobutyl ketone.

These solvents are used singly or in combination of two or more kinds.

Silyl Ester Copolymer (B2-1)

In the present invention, also employable as the silyl ester copolymer (B2) is a silyl (meth)acrylate copolymer containing:

a silyl (meth)acrylate constituent unit (d) represented by the following formula (III-a):

[Compound 24]

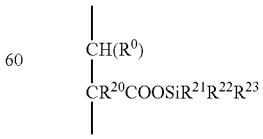

[III-a]

wherein $R^0$ is a hydrogen atom or —COOH, preferably a hydrogen atom (H), $R^{20}$ is a hydrogen atom or a methyl group, $R^{21}$ and $R^{22}$ are each independently a straight-chain alkyl group of 1 to 10 carbon atoms, a phenyl group which may be substituted or a trimethylsilyloxy group, and $R^{23}$ is an alkyl group of 1 to 18 carbon atoms which may have a ring structure or a branch, a phenyl group of 6 to 10 carbon atoms which may be substituted or a trimethylsilyloxy group; and a silyl (meth)acrylate constituent unit (e) represented by the following formula (III-b):

[Compound 25]

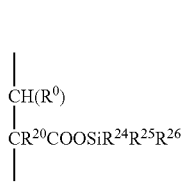

(III-b)

wherein $R^0$ is a hydrogen atom or —COOH, preferably a hydrogen atom (H), $R^{20}$ is a hydrogen atom or a methyl group, $R^{24}$ and $R^{25}$ are each independently a branched alkyl or cycloalkyl group of 3 to 10 carbon atoms, and $R^{26}$ is a straight-chain alkyl group of 1 to 10 carbon atoms, a branched alkyl or cycloalkyl group of 3 to 10 carbon atoms, a phenyl group of 6 to 10 carbon atoms which may be substituted or a trimethylsilyloxy group.

The constituent units (d), (e) and (f) for constituting the silyl (meth)acrylate copolymer (B2-1) are described below in order.

(d) Silyl (Meth)Acrylate Constituent Unit

The silyl (meth)acrylate constituent unit (d) is represented by the following formula (III-a).

[Compound 26]

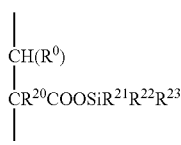

(III-a)

In the formula (III-a), $R^0$ is a hydrogen atom or —COOH, preferably a hydrogen atom (H), $R^{20}$ is a hydrogen atom or a methyl group, $R^{21}$ and $R^{22}$ are each independently a straight-chain alkyl group of 1 to 10 carbon atoms, preferably 1 to 8 carbon atoms, more preferably 1 to 6 carbon atoms, a phenyl group which may be substituted or a trimethylsilyloxy group. Examples of the straight-chain alkyl groups include methyl, ethyl, n-propyl, n-butyl, n-pentyl, n-hexyl, n-heptyl, n-octyl, n-nonyl and n-decyl.

Examples of substituents with which a hydrogen atom in the phenyl group can be replaced include alkyl, aryl and halogen.

$R^{23}$ is an alkyl group of 1 to 18 carbon atoms, preferably 1 to 12 carbon atoms, more preferably 1 to 9 carbon atoms, which may have a ring structure or a branch, a phenyl group of 6 to 10 carbon atoms, preferably 6 to 8 carbon atoms, which may be substituted, or a trimethylsilyloxy group ($(CH_3)_3SiO$—).

Examples of such alkyl groups include:
the above-exemplified straight-chain alkyl groups;
branched alkyl groups, such as isopropyl, isobutyl, sec-butyl, tert-butyl and neopentyl; and
alicyclic alkyl groups having alicyclic structure (cyclohexane ring, norbornene ring), such as cyclohexyl and ethylidenenorbornyl.

$R^{21}$, $R^{22}$ and $R^{23}$ may be the same or different and are each preferably methyl, ethyl, n-propyl, n-butyl, n-hexyl, trimethylsilyloxy, particularly preferably methyl, n-propyl, n-butyl or n-hexyl, among the above groups.

The silyl (meth)acrylate (d1) from which the silyl (meth) acrylate constituent unit (d) can be derived is represented by the following formula (III-a-1):

[Compound 27]

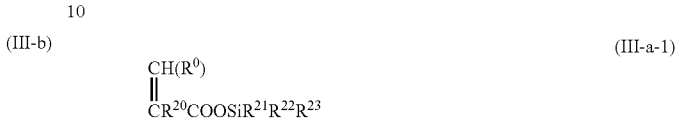

(III-a-1)

wherein $R^0$, $R^{20}$, and $R^{21}$ to $R^{23}$ are the same as $R^0$, $R^{20}$, and $R^{21}$ to $R^{23}$ in the formula (III-a) representing the constituent unit (d).

Examples of the silyl (meth)acrylates (III-a-1) include:
aliphatic silyl (meth)acrylates wherein $R^{21}$, $R^{22}$ and $R^{23}$ are the same as one another, such as trimethylsilyl (meth)acrylate, triethylsilyl (meth)acrylate, tri-n-propylsilyl (meth)acrylate, tri-n-butylsilyl (meth)acrylate, tri-n-pentylsilyl (meth)acrylate, tri-n-hexylsilyl (meth)acrylate, tri-n-heptylsilyl (meth)acrylate, tri-n-octylsilyl (meth)acrylate, tri-n-nonylsilyl (meth)acrylate and tri-n-decylsilyl (meth)acrylate;

aromatic or siloxane-based silyl (meth)acrylates wherein $R^{21}$, $R^{22}$ and $R^{23}$ are the same as one another, such as triphenylsilyl (meth)acrylate and tris(trimethylsilyloxy)silyl (meth)acrylate; and aliphatic silyl (meth)acrylates wherein $R^{21}$, $R^{22}$ and $R^{23}$ are partially or completely different from one another, such as dimethyl-n-propylsilyl (meth)acrylate, isopropyldimethylsilyl (meth)acrylate, di-n-butyl-isobutylsilyl (meth)acrylate, n-hexyldimethylsilyl (meth)acrylate, sec-butyldimethylsilyl (meth)acrylate, monomethyl-di-n-propylsilyl (meth)acrylate, methylethyl-n-propylsilyl (meth)acrylate, ethylidenenorbornyldimethylsilyl (meth)acrylate and trimethylsilyloxydimethylsilyl (meth)acrylate ($CH_2=C(CH_3)COO—Si(CH_3)_2(OSi(CH_3)_3$, $CH_2=CHCOOSi(CH_3)_2)(OSi(CH_3)_3$).

In the present invention, the silyl (meth)acrylates (III-a-1) can be used singly or in combination of two or more kinds.

(e) Silyl (Meth)Acrylate Constituent Unit

The silyl (meth)acrylate constituent unit (e) is represented by the following formula (III-b).

[Compound 28]

(III-b)

In the formula (III-b), $R^0$ is a hydrogen atom or —COOH, preferably a hydrogen atom, $R^{20}$ is a hydrogen atom or a methyl group, and $R^{24}$ and $R^{25}$ are each independently a branched alkyl group of 3 to 10 carbon atoms, preferably 3 to 8 carbon atoms, or a cycloalkyl group of 3 to 10 carbon atoms, preferably 3 to 9 carbon atoms.

Examples of the branched alkyl groups include isopropyl, isobutyl, sec-butyl, tert-butyl and neopentyl, similarly to those in the formula (III-a).

Examples of the cycloalkyl groups include cyclohexyl and ethylidenenorbornyl.

$R^{26}$ is a straight-chain alkyl group of 1 to 10 carbon atoms, preferably 1 to 8 carbon atoms, more preferably 1 to 6 carbon atoms, a branched alkyl or cycloalkyl group of 3 to 10 carbon atoms, preferably 3 to 9 carbon atoms, a phenyl group of 6 to 10 carbon atoms, preferably 6 to 8 carbon atoms, which may be substituted, or a trimethylsilyloxy group.

Examples of the straight-chain alkyl groups, the branched alkyl or cycloalkyl groups and the phenyl groups include the same groups as describe above.

$R^{24}$, $R^{25}$ and $R^{26}$ may be the same as or different from one another, and when they are the same, they are each preferably isopropyl, sec-butyl or isobutyl, particularly preferably isopropyl or sec-butyl, among the above groups.

When $R^{24}$, $R^{25}$ and $R^{26}$ are partially or completely different from one another, $R^{24}$ and $R^{25}$ may be the same or different and are each preferably isopropyl, isobutyl, sec-butyl or tert-butyl, and $R^{26}$ is preferably methyl, ethyl, propyl, isopropyl, n-butyl, isobutyl or trimethylsilyloxy.

The silyl (meth)acrylate (e1) from which the silyl (meth)acrylate constituent unit (e) can be derived is represented by the following formula (III-b-1):

[Compound 29]

(III-b-1)

wherein $R^0$, $R^{20}$, $R^{24}$, $R^{25}$ and $R^{26}$ are the same as $R^0$, $R^{20}$, $R^{24}$, $R^{25}$ and 26 in the formula (III-b) representing the constituent unit (e).

Examples of the silyl (meth)acrylates (III-b-1) include:

silyl (meth)acrylates wherein $R^{24}$, $R^{25}$ and $R^{26}$ are the same as one another, such as triisopropylsilyl (meth)acrylate, triisobutylsilyl (meth)acrylate and tri-sec-butylsilyl (meth)acrylate; and silyl (meth)acrylates wherein $R^{24}$, $R^{25}$ and $R^{26}$ are partially or completely different from one another, such as diisopropylcyclohexylsilyl (meth)acrylate, diisopropylphenylsilyl (meth)acrylate, diisopropyltrimethylsiloxysilyl (meth)acrylate, di-sec-butylmethylsilyl (meth)acrylate, di-sec-butylethylsilyl (meth)acrylate, di-sec-butyltrimethylsilyloxysilyl (meth)acrylate and isopropyl-sec-butylmethylsilyl (meth)acrylate.

In the present invention, the silyl (meth)acrylates (III-b-1) can be used singly or in combination of two or more kinds.

Taking into consideration ease of synthesis of the silyl (meth)acrylate copolymer and film-forming property, storage stability and ease of control of self-polishing property of an antifouling paint composition comprising the silyl (meth)acrylate copolymer, it is preferable to use a combination of one or more compounds selected from trimethylsilyl (meth)acrylate, triethylsilyl (meth)acrylate, tri-n-propylsilyl (meth)acrylate, tri-n-butylsilyl (meth)acrylate, n-hexyldimethylsilyl (meth)acrylate, n-octyldimethylsilyl (meth)acrylate, isopropyldimethylsilyl (meth)acrylate, ethylidenenorbornyldimethylsilyl (meth)acrylate, trimethylsilyloxydimethylsilyl (meth)acrylate, bis(trimethylsilyloxy)methylsilyl (meth)acrylate and tris(trimethylsilyloxy)silyl (meth)acrylate among the silyl (meth)acrylate (III-b-1) and one or more compounds selected from triisopropylsilyl (meth)acrylate, triisobutylsilyl (meth)acrylate, tri-sec-butylsilyl (meth)acrylate, di-sec-butylmethylsilyl (meth)acrylate, diisopropyltrimethylsilyloxysilyl (meth)acrylate and di-sec-butyltrimethylsilyloxysilyl (meth)acrylate among the silyl (meth)acrylates (III-b-1).

It is more preferable to use a combination of tri-n-butylsilyl (meth)acrylate among the silyl (meth)acrylates (III-b-1) and triisopropylsilyl (meth)acrylate among the silyl (meth)acrylates (III-b-1).

(f) Unsaturated Monomer Constituent Unit

The unsaturated monomer constituent unit (f) constitutes the silyl (meth)acrylate copolymer of the invention together with the constituent unit (d) and the constituent unit (e), and is different from both the constituent units (d) and (e). The unsaturated monomer (f1) from which the unsaturated monomer constituent unit (f) can be derived is, for example, the polar group-containing (meth)acrylate (b) represented by the formula (IV-a) or the unsaturated monomer (c-1) from which the unsaturated monomer constituent unit (c) can be derived.

Examples of such monomers include:

hydrophobic (methyl)acrylic acid esters, such as methyl (meth)acrylate, ethyl (meth)acrylate, n-, iso-, -tert-butyl (meth)acrylate, 2-ethylhexyl (meth)acrylate and cyclohexyl (meth)acrylate; hydrophilic (meth)acrylic acid esters, such as 2-hydroxyethyl (meth)acrylate, 2-hydroxypropyl (meth)acrylate, 2-hydroxybutyl (meth)acrylate, 4-hydroxybutyl (meth)acrylate, 2-methoxyethyl (meth)acrylate, alkoxypolyethylene glycol mono(meth)acrylate and alkoxypolypropylene glycol mono(meth)acrylate;

styrenes, such as styrene, vinyltoluene and □-methylstyrene;

vinyl esters, such as vinyl acetate, vinyl benzoate, vinyl propionate and vinyl butyrate; and organic carboxylic acid esters, such as itaconic acid esters and maleic acid esters.

Of these, (meth)acrylic acid esters, strenes and organic carboxylic acid vinyl esters are preferable because an antifouling coating film having proper film strength is obtained.

By the use of the hydrophilic (meth)acrylic acid esters, erodibility of the coating film can be increased, and for this purpose, comonomers having hydrophilicity, such as acrylamide derivatives, are also employable.

The unsaturated monomers (f1) are used singly or in combination of two or more kinds.

In the present invention, it is desirable that in the silyl (meth)acrylate copolymer, the silyl (meth)acrylate constituent units (d) are contained in amounts of 0.5 to 50% by weight, preferably 0.5 to 25% by weight, the silyl (meth)acrylate constituent units (e) are contained in amounts of 10 to 70% by weight, preferably 30 to 65% by weight, and the unsaturated monomer constituent units (f) other than the constituent units (d) and (e) are contained in amounts of 20 to 70% by weight, preferably 30 to 60% by weight ((d)+(e)+(f)=100% by weight), from the viewpoints of prevention of occurrence of cracks in a coating film and peeling resistance, film strength and erodibility of a coating film.

The weight-average molecular weight (Mw) of the silyl (meth)acrylate copolymer (B2-1), as measured by gel permeation chromatography (GPC), is desired to be not more than 200,000, preferably 3,000 to 100,000, more preferably 5,000 to 100,000, particularly preferably 5,000 to 80,000, from the viewpoints of ease of preparation of an antifouling paint containing the silyl (meth)acrylate copolymer, storage stability and painting workability of the resulting antifouling paint, and erosion rate and crack resistance of an antifouling coating film.

Preparation of Silyl (Meth)Acrylate Copolymer (B2-1)

In order to obtain the silyl (meth)acrylate copolymer (B2-1), 0.5 to 50% by weight of the silyl (meth)acrylate (d1)

represented by the formula (III-a-1), 10 to 70% by weight of the silyl (meth)acrylate (e1) represented by the formula (III-b-1) and 20 to 70% by weight of the unsaturated monomer (f1) copolymerizable with the monomers (d1) and (e1) ((d1)+(e1)+(f1)=100% by weight) have only to be random-copolymerized by various processes, such as solution polymerization, bulk polymerization, emulsion polymerization and suspension polymerization, in the presence of a radical polymerization initiator. In the polymerization, such a chain transfer agent as previously mentioned may be used.

As the radical polymerization initiator, hitherto known azo compounds, peroxides, etc. can be widely employed. Examples of the azo compounds include 2,2'-azobisisobutyronitrile, 2,2'-azobis(2-methylburyronitrile) and 2,2'-azobis (2,4-dimethylvaleronitrile). Examples of the peroxides include benzoyl peroxide, tert-butyl peroxyacetate, tert-butyl peroxyoctoate, cumene hydroperoxide, tert-butyl peroxide, tert-butyl peroxybenzoate, tert-butyl peroxyisopropyl carbonate, tert-butyl hydroperoxide and persulfuric acid salts (potassium salt, ammonium salt).

In the case where the above polymer is used for an antifouling paint, the solution polymerization process or the bulk polymerization process wherein the polymerization is carried out in an organic solvent is preferable among the aforesaid various polymerization processes. Examples of the organic solvents used in the solution polymerization include:

- aromatic hydrocarbons, such as xylene and toluene;
- aliphatic hydrocarbons, such as hexane and heptane;
- esters, such as ethyl acetate and butyl acetate;
- alcohols, such as isopropyl alcohol and butyl alcohol;
- ethers, such as dioxane and diethyl ether; and
- ketones, such as methyl ethyl ketone and methyl isobutyl ketone. These solvents are used singly or in combination of two or more kinds.

In the antifouling paint composition of the invention, the compounding agent (A) for an antifouling paint and the copolymer (B) for a self-polishing type antifouling paint are contained as essential components, and it is desirable that the component (A) is contained in an amount of usually 0.01 to 80% by weight, preferably 0.1 to 50% by weight, and the component (B) is contained in an amount of usually 1 to 60% by weight, preferably 3 to 40% by weight.

When the components (A) and (B) are contained in such amounts in the antifouling paint composition or the antifouling coating film, hydrolysis rate of the component (A) contained is favorably controlled, and as a result, the coating film tends to become excellent in the long-term antifouling property, particularly antifouling performance in the highly fouling sea area or in the static environment.

Further, it is desirable that the compounding agent (A) for an antifouling paint is contained in an amount of usually 0.01 to 90 parts by weight, preferably 0.1 to 75 parts by weight, and the copolymer component (B) (non-volatile matter) is contained in the residual amount, i.e., usually 10 to 99.99 parts by weight, preferably 25 to 99.9 parts by weight, in the total 100 parts by weight of the components (A) and (B) ((A)+(B)), from the viewpoints of antifouling property of the coating film, proper erodibility of the coating film and coating film properties.

According to the antifouling paint composition containing the components (A) and (B), a paint having excellent storage stability is obtained. Moreover, an antifouling coating film which rarely suffers occurrence of cracks, is favorably controlled in hydrolysis rate and is excellent in antifouling performance, particularly antifouling performance in the highly fouling environment and long-term antifouling performance, is obtained.

The antifouling paint composition of the invention may further contain various additives.

That is to say, the antifouling paint composition of the invention contains the compounding agent (A) for an antifouling paint and the copolymer (B) for a self-polishing type antifouling paint as essential components, and in addition to the components (A) and (B), various additives, e.g., an antifouling agent (C) (particularly (C1) copper and/or copper compound, (C2) organic antifouling agent), zinc oxide (zinc white) (D), a dehydrating agent (E), an anti-sagging/anti-setting agent, an elution acceleration component (F) such as rosin, various pigments such as coloring pigment and extender pigment, various resins such as acrylic resin and polyalkyl vinyl ether (vinyl ether-based (co)polymer) (G), a plasticizer (H) such as chlorinated paraffin, an anti-foaming agent, a segregation preventing agent, a leveling agent and a solvent, may be contained.

Next, such various additives are described.

Antifouling Agent (C)

The antifouling agent (C) may be any of an inorganic antifouling agent and an organic antifouling agent, and hitherto known antifouling agents can be widely employed. In the present invention, (C1) copper and/or a copper compound or (C2) an organic antifouling agent is preferable.

The copper and/or the copper compound (C1) (except organic copper compound such as pyrithione, the same shall apply hereinafter) which may be contained in the antifouling paint composition of the invention is described below.

As the copper compound (C1) for use in the invention, any of inorganic copper compounds is employable, and examples of the inorganic copper compounds include cuprous oxide, copper thiocyanate (cuprous thiocyanate, copper rhodanide), basic copper sulfate, copper chloride and copper oxide. Of these, cuprous oxide and copper thiocyanide (copper rhodanide) are preferably employed.

Such copper compounds can be used singly or in combination, instead of copper or together with copper.

The copper and/or the copper compound (C1) is desirably contained in the total amount of usually 1 to 70% by weight, preferably 3 to 65% by weight, in 100% by weight of the antifouling paint composition of the invention. Further, based on 100 parts by weight of the copolymer (B) (non-volatile matter) for a self-polishing type antifouling paint contained in the antifouling paint composition, preferably the silyl ester-based copolymer (B) (non-volatile matter), the copper and/or the copper compound (C1) is desirably contained in the total amount of usually 3 to 1400 parts by weight, preferably 10 to 1300 parts by weight.

When the copper and/or the copper compound is contained in the above amount in the antifouling paint composition, an antifouling coating film having excellent antifouling property can be formed.

In the present invention, an organic antifouling agent (C2) can be used together with the copper and/or the copper compound (C1) or instead of the copper and/or the copper compound (C1). Examples of the organic antifouling agents (C2) employable include metallic pyrithiones and organic copper compounds. In particular, metallic pyrithiones are preferable.

Examples of the metallic pyrithiones include metallic pyrithiones of sodium, magnesium, calcium, barium, aluminum, copper, zinc, iron and lead. Of the metallic pyrithiones, preferable are copper pyrithione and zinc pyrithione, and particularly preferable is copper pyrithione.

Examples of the organic copper compounds include basic copper acetate, oxine-copper, copper nonylphenolsulfonate, copper bis(ethylenediamine)-bis(dodecylbenzenesulfonate), copper naphthenate, copper rosinate and copper bis(pentachlorophenolate).

In the antifouling paint composition of the invention, the organic antifouling agent is desirably contained in an amount of usually 0.1 to 50% by weight, preferably 0.5 to 25% by weight. Further, based on 100 parts by weight of the copolymer (B) (non-volatile matter) for a self-polishing type antifouling paint contained in the antifouling paint composition, preferably the silyl ester-based copolymer (B) (non-volatile matter), the organic antifouling agent is desirably contained in an amount of usually 0.3 to 300 parts by weight, preferably 2 to 200 parts by weight.

In the present invention, the following antifouling agents (other antifouling agents) may be contained together with the pyrithione compound or instead of the pyrithione compound. As the other antifouling agents, various antifouling agents hitherto known are employable, and examples thereof include tetramethylthiuram disulfide, carbamate compounds (e.g., zinc dimethyldithiocarbamate, manganese 2-ethylenebisdithiocarbamate), 2,4,5,6-tetrachloroisophthalonitrile, N,N-dimethyldichlorophenylurea, 2-methylthio-4-tert-butylamino-6-cyclopropylamino-s-triazine, 4,5-dichloro-2-n-octyl-4-isothiazoline-3-one, 2,4,6-trichlorophenylmaleimide, pyridine-triphenylborane and amine-triphenylborane.

In the present invention, such antifouling agents can be used singly or in combination of two or more kinds, together with the pyrithione compounds (metallic pyrithiones) such as zinc pyrithione and copper pyrithione. For example, copper pyrithione and/or zinc pyrithione, and 4,5-dichloro-2-n-octyl-4-isothiazoline-3-one can be used in combination.

The total amount of various antifouling gents contained in the antifouling paint composition, such as copper and/or the copper compound (C1) and the organic antifouling agent (C2), depends upon the types of the antifouling agents and the film-forming copolymer used in the preparation of the antifouling paint composition or the types of ships (e.g., for ocean route or coastal route, for various sea areas, for wooden or steel ship), etc. to be coated with the antifouling paint composition, and cannot be determined indiscriminately. However, it is desirable that such antifouling agents are contained in the total amount of usually 10 to 1400 parts by weight, preferably 20 to 1300 parts by weight, based on 100 parts by weight of the copolymer (B) (non-volatile matter) for a self-polishing type antifouling paint, preferably the silyl ester-based copolymer (B) (non-volatile matter).

When the total amount of the antifouling agents is in the above range, crack resistance and antifouling property tend to become excellent.

In the case where copper pyrithione and cuprous oxide ($Cu_2O$) are used in combination as the antifouling agents of the antifouling paint composition, it is desirable that the copper pyrithione is contained in an amount of 2 to 100 parts by weight based on 100 parts by weight of the copolymer (B) (non-volatile matter) for a self-polishing type antifouling paint, preferably the silyl ester-based copolymer (B) (non-volatile matter), and the cuprous oxide is contained in an mount of usually about 10 to 1300 parts by weight based on 100 parts by weight of the copolymer (B) (non-volatile matter).

Zinc Oxide (Zinc White)(D)

In the antifouling paint composition of the invention, zinc oxide (zinc white) D may be contained. By the use of the antifouling paint composition containing zinc oxide, strength of the resulting coating film can be enhanced and self-polishing property of the coating film can be effectively controlled. From the viewpoints of control of erodibility and control of coating film hardness, zinc oxide is desirably contained in an amount of usually 0.5 to 35% by weight, preferably 1 to 25% by weight, in the antifouling paint composition. Further, based on 100 parts by weight of the copolymer (B) (non-volatile matter) for a self-polishing type antifouling paint, preferably the silyl ester-based copolymer (B) (non-volatile matter), zinc oxide is desirably contained in an amount of usually 1.5 to 1200 parts by weight, preferably 4 to 600 parts by weight, in the antifouling paint composition.

Inorganic Dehydrating Agent (E)

To the antifouling paint composition of the invention, a dehydrating agent of inorganic or organic type, preferably a dehydrating agent of inorganic type (inorganic dehydrating agent (E), may be added. By the addition of the dehydrating agent to the antifouling paint composition, storage stability of the composition can be further improved.

Examples of the dehydrating agents include anhydrous gypsum ($CaSO_4$), synthetic zeolite type adsorbents (trade name: Molecular Sieves, etc.), ortho esters, such as methyl orthoformate and methyl orthoacetate, orthoboric acid esters, silicates, and isocyanates (trade name: Additive T1, etc.). In particular, anhydrous gypsum and Molecular Sieves are preferably used as the inorganic dehydrating agents (D). These inorganic dehydrating agents (D) can be used singly or in combination of two or more kinds.

The dehydrating agents, particularly the inorganic dehydrating agents, are desirably added in the total amount of usually 0.02 to 100 parts by weight, preferably 0.2 to 50 parts by weight, based on 100 parts by weight of the copolymer (B) (non-volatile matter) for a self-polishing type antifouling paint, preferably the silyl ester-based copolymer (B) (non-volatile matter).

Further, the inorganic dehydrating agents are desirably contained in the total amount of usually 0.01 to 20% by weight, preferably 0.1 to 8% by weight, in the antifouling paint composition. When the inorganic dehydrating agents are contained in the above amount in the antifouling paint composition, storage stability tends to be enhanced.

Elution Acceleration Component (F)

In the antifouling paint composition of the invention, an elution acceleration component (F) may be contained (the component (B) is not included in the elution acceleration component (F)), and examples thereof include rosin, rosin derivatives, organic carboxylic acids and organic carboxylic acid metal salts.

As the rosin, there can be mentioned gum rosin, wood rosin, tall oil rosin, etc., and any of them can be employed in the invention. Examples of the rosin derivatives include disproportionated rosin, low-melting point disproportionated rosin, hydrogenated rosin, polymerized rosin, maleic rosin, aldehyde modified rosin, polyoxyalkylene ester of rosin, reduced rosin (rosin alcohol), metal salts of rosin (e.g., copper salt, zinc salt and magnesium salt of rosin) and rosin amide. These rosin and rosin derivatives can be used singly or in combination of two or more kinds.

Examples of the organic carboxylic acids include aliphatic acids of about 5 to 30 carbon atoms, synthetic aliphatic acids and napthenic acid. Examples of the metal salts of organic carboxylic acids include Cu salt, Zn salt, Mg salt and Ca salt. As the metal salt of an organic carboxylic acid, an excess metal salt of an organic carboxylic acid may be used, or a salt composed of an organic acid and a metal in an equal equivalent ratio or lower may be used.

The above elution acceleration components can be used singly or in combination of two or more kinds.

In the case where the antifouling paint composition contains these solution acceleration components, the solution acceleration components are desirably contained in the total amount of 0.1 to 30% by weight, preferably 0.1 to 20% by weight, more preferably 0.5 to 15% by weight, in 100 parts by weight of the antifouling paint composition. From the viewpoints of antifouling performance and water resistance of the resulting coating film, the amount of the elution acceleration components added is desirably in the above range.

Further, based on 100 parts by weight of the copolymer (B) (non-volatile matter) for a self-polishing type antifouling paint contained in the antifouling paint composition, preferably the silyl ester-based copolymer (B) (non-volatile matter), the elution acceleration components are desirably contained in the total amount of usually 0.3 to 600 parts by weight, preferably 2 to 300 parts by weight.

When the solution acceleration components are contained in the above amount, antifouling property and erodibility of the resulting coating film tend to become excellent.

Vinyl Ether-Based (Co)Polymer (G)

The vinyl ether-based (co)polymer has a vinyl ether constituent unit, contributes to improvements in crack resistance, peeling resistance and elution rate stability of the resulting coating film and functions also as a film-forming component.

Examples of the vinyl ether-based (co)polymers include polyvinyl methyl ether, polyvinyl ethyl ether, polyvinyl isopropyl ether and polyvinyl isobutyl ether.

These vinyl ether-based (co)polymers (G) are desirably contained in the total amount of usually 0.1 to 10 parts by weight, preferably 0.2 to 5 parts by weight, in 100 parts by weight of the antifouling paint composition. Further, based on 100 parts by weight of the copolymer (B) (non-volatile matter) for a self-polishing type antifouling paint contained in the antifouling paint composition, preferably the silyl ester-based copolymer (B) (non-volatile matter), the vinyl ether-based (co)polymers are desirably contained in the total amount of usually 0.3 to 60 parts by weight, preferably 0.6 to 40 parts by weight.

When the vinyl ether base (co)polymers are contained in the above amount, crack resistance, peeling resistance and elution rate stability of the resulting coating film tend to become excellent.

Instead of the vinyl ether-based (co)polymer or together with the vinyl ether-based (co)polymer, various hydrophilic group-containing polymers can be employed. Examples of the hydrophilic group-containing polymers include various (alkoxy)polyalkylene glycol mono(meth)acrylate (co)polymers such as a (methoxy)polyethylene glycol mono(meth)acrylate copolymer. By the use of such a polymer, it becomes possible to obtain the same effects as obtained by the use of the vinyl ether-based (co)polymer.

Plasiticizer (H)

As the plasticizer, a plasticizer usually used for paints, such as orthophosphoric acid ester, chlorinated paraffin, phthalic acid ester or adipic acid ester, is employable. These plasticizers can be used singly or in combination of two or more kinds.

In the case where such a plasticizer is used, the amount of the plasticizer added to the antifouling paint composition is, for example, 0.1 to 10% by weight.

The plasticizer contributes to enhancement of crack resistance of a coating film (also referred to as an "antifouling coating film" in this specification) obtained from the antifouling paint composition. Of the above plasticizers, chlorinated paraffin or orthophosphoric acid ester such as tricresyl phosphate (TCP) is preferably employed.

The chlorinated paraffin may be straight-chain or may have a branch, and may be liquid or solid (powder) at room temperature. As such chlorinated paraffin, "Toyoparax 150" or "Toyoparax A-70" available from Tosoh Corporation can be mentioned. In the present invention, two or more kinds of chlorinated paraffins different in chlorine content, number of carbon atoms, etc. can be used in combination.

In the case where the chlorinated paraffin is used as the plasticizer (H), it is desirably contained in an amount of usually 0.05 to 20 parts by weight, preferably 0.1 to 15 parts by weight, in 100 parts by weight of the antifouling paint composition. Further, based on 100 parts by weight of the copolymer (B) (non-volatile matter) for a self-polishing type antifouling paint contained in the antifouling paint composition, preferably the silyl ester-based copolymer (B) (non-volatile matter), the chlorinated paraffin is desirably contained in an amount of 1 to 50 parts by weight, preferably 2 to 40 parts by weight. When the amount of the chlorinated paraffin is in this range, the resulting coating film tends to become excellent in inhibition of cracks, film strength and damage (impact) resistance.

In the case where the orthophosphoric acid ester is used as the plasticizer (H), it is desirably contained in an amount of usually 0.05 to 20% by weight, preferably 0.1 to 15% by weight, in 100% by weight of the antifouling paint composition.

Further, based on 100 parts by weight of the copolymer (B) (non-volatile matter) for a self-polishing type antifouling paint contained in the antifouling paint composition, preferably the silyl ester-based copolymer (B) (non-volatile matter) containing a constituent unit derived from the polymerizable unsaturated carboxylic acid silyl ester, the orthophosphoric acid ester is desirably contained in an amount of 1 to 50 parts by weight, preferably 2 to 40 parts by weight.

When the orthophosphoric acid ester is contained in the above amount as the plasticizer (H), a coating film little suffering cracking and peeling can be formed, and erodibility of the coating film can be increased.

Other Components

The antifouling paint composition of the invention may contain, in addition to the above components, various additives, such as an anti-sagging/anti-setting agent, various pigments (e.g., coloring pigment and extender pigment), various resins except the above-mentioned vinyl ether-based (co)polymer (e.g., acrylic resin), an anti-foaming agent, a segregation preventing agent, a leveling agent and a solvent, which are described below.

Anti-Sagging/Anti-Setting Agent

As the anti-sagging/anti-setting agent, a hitherto known agent may be added in an arbitrary amount. Examples of the anti-sagging/anti-setting agents include stearates of Al, Ca and Zn, lecithin salt and alkylsulfonic acid salt, polyethylene wax, hydrogenated castor oil wax, polyamide wax, mixtures thereof, synthetic powder silica and polyethylene oxide wax. Of these, hydrogenated castor oil wax, polyamide wax, synthetic powder silica and polyethylene oxide wax are preferably employed. As such an anti-sagging/anti-setting agent, an agent that is on the marked under the trade name of "Disperon A-603-20X" or "Disperson 4200-20" available from Kusumoto Chemicals, Ltd. can be mentioned.

Pigment, Solvent

Examples of the pigments employable in the invention include hitherto known organic or inorganic various pigments, such as titanium white, red iron oxide, organic red pigment and talc). Various colorants such as dyes may be also included.

By the use of a pigment in a needle, flat or scaly form, it becomes possible to further enhance crack resistance of a coating film.

Examples of the solvents employable in the invention include various solvents usually added to antifouling paints, such as aliphatic solvents, aromatic solvents (e.g., xylene, toluene), ketone-based solvents, ester-based solvents and ether-based solvents. Further, the solvent used for preparing the polymerizable unsaturated carboxylic acid metal compound-based copolymer may be included in the solvent contained in the antifouling paint composition of the invention.

Various Resins

Examples of various resins include acrylic resins which are other resin components, such as acrylic acid (co)polymer, acrylic acid ester (co)polymer, methacrylic acid (co)polymer, methacrylic acid ester (co)polymer and 2-hydroxyethyl acrylate (co)polymer. Further, silyl ester-based (co)polymers described in, for example, Japanese Patent Laid-Open Publication No. 264170/1992, Japanese Patent Laid-Open Publication No. 264169/1992, Japanese Patent Laid-Open Publication No. 264168/1992, Japanese Patent Laid-Open Publication No. 196869/1990, National Publication of International Patent No. 500452/1985, Japanese Patent Laid-Open Publication No. 215780/1988, National Publication of International Patent No. 500452/1985 (Japanese Patent Publication No. 32433/1993) and Japanese Patent Laid-Open Publication No. 18216/1995 may be contained in the antifouling paint composition of the invention.

Preparation of Antifouling Paint Composition

The antifouling paint composition of the invention can be prepared by properly using a hitherto known process. For example, the compounding agent (A) for an antifouling paint, the copolymer (B) for a self-polishing type antifouling paint, and if necessary, the antifouling agent (C) (particularly (C1) copper and/or copper compound, (C2) organic antifouling agent), zinc oxide (D), the dehydrating agent (E) (e.g., anhydrous gypsum, Molecular Sieves), the elution acceleration component (F), the vinyl ether-based (co)polymer (G), the plasticizer (H), the anti-sagging/anti-setting agent, the pigment and the solvent are added at the same time or in an arbitrary order, and they are stirred, mixed or dispersed.

The antifouling paint composition is one-pack type, has excellent storage stability and satisfies various requirements for antifouling paints, such as adhesion, durability and antifouling property.

By coating surfaces of various molded articles (base materials), such as underwater/water surface structures, i.e., marine structures (e.g., water feed or drainage opening of atomic power plant), polluted sludge diffusion preventive films in various marine engineering of bay coast roads, submarine tunnels, port facilities, canals and channels, and ships and fishing tackles (e.g., rope, fishing net) with the antifouling paint composition once or plural times in a conventional manner and curing the composition, antifouling paint film coated ships, marine structures, etc. which exhibit excellent crack resistance and antifouling performance can be obtained. The antifouling paint composition may be directly applied to surfaces of the above ships or marine structures, or may be applied to surfaces of the above ships or marine structures having been coated with an undercoating material, such as anticorrosion agent or primer. Further, the surfaces of ships or marine structures having been previously coated with a conventional antifouling paint or the antifouling paint composition of the invention may be topcoated with the antifouling paint composition of the invention for repairing. The thickness of the antifouling coating film formed on the surfaces of the ships or the marine structures in the above manner is not specifically restricted, but it is, for example, about 30 to 150 μm/one coating time.

EFFECT OF THE INVENTION

According to the present invention, there can be obtained an antifouling paint composition having high storage stability and capable of forming an antifouling coating film which is favorably controlled in the hydrolysis rate, is excellent in antifouling performance (antifouling activity), particularly antifouling property in the highly fouling sea area or in the static environment or long-term antifouling property, rarely suffering occurrence of cracks, has proper hardness and has an excellent balance of these properties.

According to the present invention, further, a coating film having the above-mentioned excellent properties, and a ship, an underwater structure, a fishing tackle and a fishing net coated with the coating film are provided.

According to the present invention, furthermore, an antifouling method using the antifouling paint composition, in which there is very little fear of environmental pollution, is provided.

EXAMPLES

The present invention is further described with reference to the following examples, but it should be construed that the invention is in no way limited to those examples.

In the following examples and comparative examples, the term "part(s)" means "part(s) by weight" unless it departs from the purpose thereof.

The conditions for measuring IR and MS spectra are as follows.

(IR Spectrum Measuring Conditions)
  Perkin-Elmer FT-IR Spectrum One
  Measuring method: neat method, using KBr plate (MS Spectrum Measuring Conditions)
  Agilent 5973MSD
  Measuring method: EI method Preparation of Cyclopentadiene by Thermal Decomposition of Dicyclopentadiene In a reaction vessel equipped with a stirrer, a dehydrator, a condenser and a heating or cooling jacket, 600 parts of dicyclopentadiene were placed, and the dicyclopentadiene was heated at 160 to 170° C. for 8 hours with stirring to obtain 400 parts of cyclopentadiene.

Preparation Examples of Compounding Agents for Antifouling Paint (Preparation of Compounding Agent (AD-1) for Antifouling Paint)

In a reaction vessel equipped with a stirrer, a condenser and a heating or cooling jacket, 720 parts of acrylic acid (AA) were placed, and thereto were dropwise added 660 parts of cyclopentadiene (CPD) over a period of 2 hours with stirring at 25 to 35° C. After the dropwise addition, stirring was performed at room temperature for 2 hours to obtain a compounding agent (AD-1) for an antifouling paint, which had a GC (gas chromatography) purity of 93%.

An IR spectrum of the compounding agent (AD-1) for an antifouling paint is shown in FIG. 1.

This compounding agent (AD-1) for an antifouling paint corresponds to a cyclic carboxylic acid (compound A-1) represented by the aforesaid formula (1) and is the aforesaid isomer mixture.

[Compound 30]

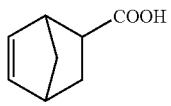
Compound A-1

(Preparation of Compounding Agent (AD-2) for Antifouling Paint)

In a reaction vessel equipped with a stirrer, a condenser and a heating or cooling jacket, 1380 parts of the compounding agent (AD-1) for an antifouling paint and 2.7 parts of activated clay as an acid catalyst were placed.

[Compound 31]

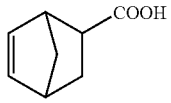
(AD-1)

Then, they were heated at 170° C. for 40 hours with stirring to obtain a brown solid compounding agent (AD-2) for an antifouling paint, which had a molecular weight of about 1600, that is, a polyester-monocarboxylic acid produced by the self-Michael addition of the compound (AD-1) in the presence of the acid catalyst.

[Compound 32]

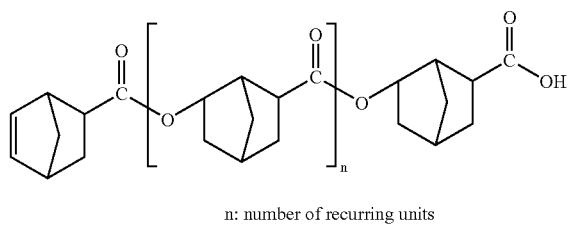
(AD-2)

n: number of recurring units

Figure 2:
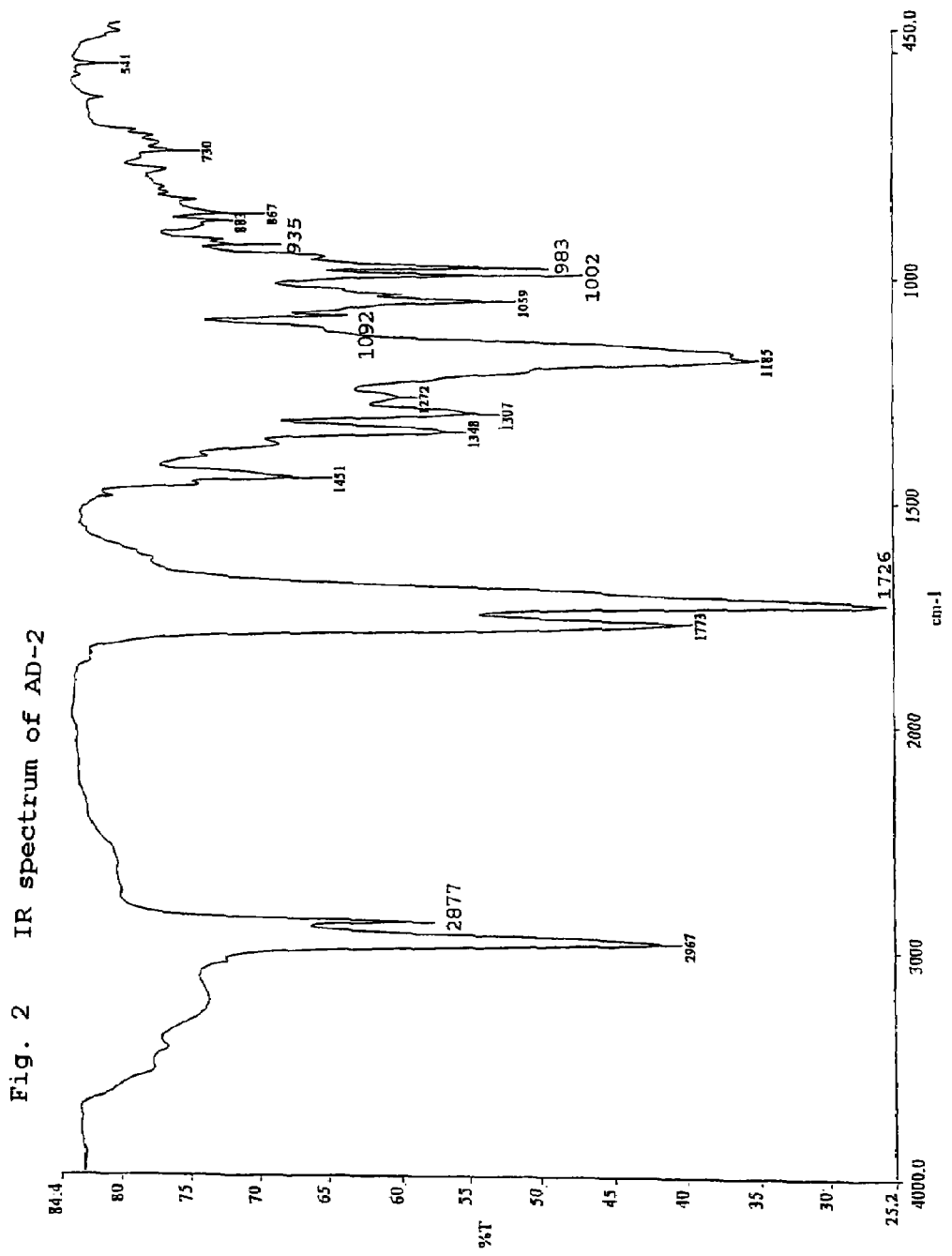
FIG. 2 shows an IR spectrum of a compounding agent (AD-2) for an antifouling paint, said compounding agent being used in an example of the invention or a comparative example.

An IR spectrum of the compounding agent (AD-2) for an antifouling paint is shown in FIG. 2.

(Preparation of Compounding Agent (AD-3) for Antifouling Paint)

In a reaction vessel equipped with a stirrer, a condenser and a heating or cooling jacket, 860 parts of methacrylic acid (MAA) and 792 parts of cyclopentadiene were placed, and they were heated at 40° C. for 24 hours with stirring to obtain a compounding agent (AD-3 (A-2)) for an antifouling paint, which had a GC (gas chromatography) purity of 80%.

[Compound 33]

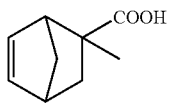
Compound A-2

Figure 3:
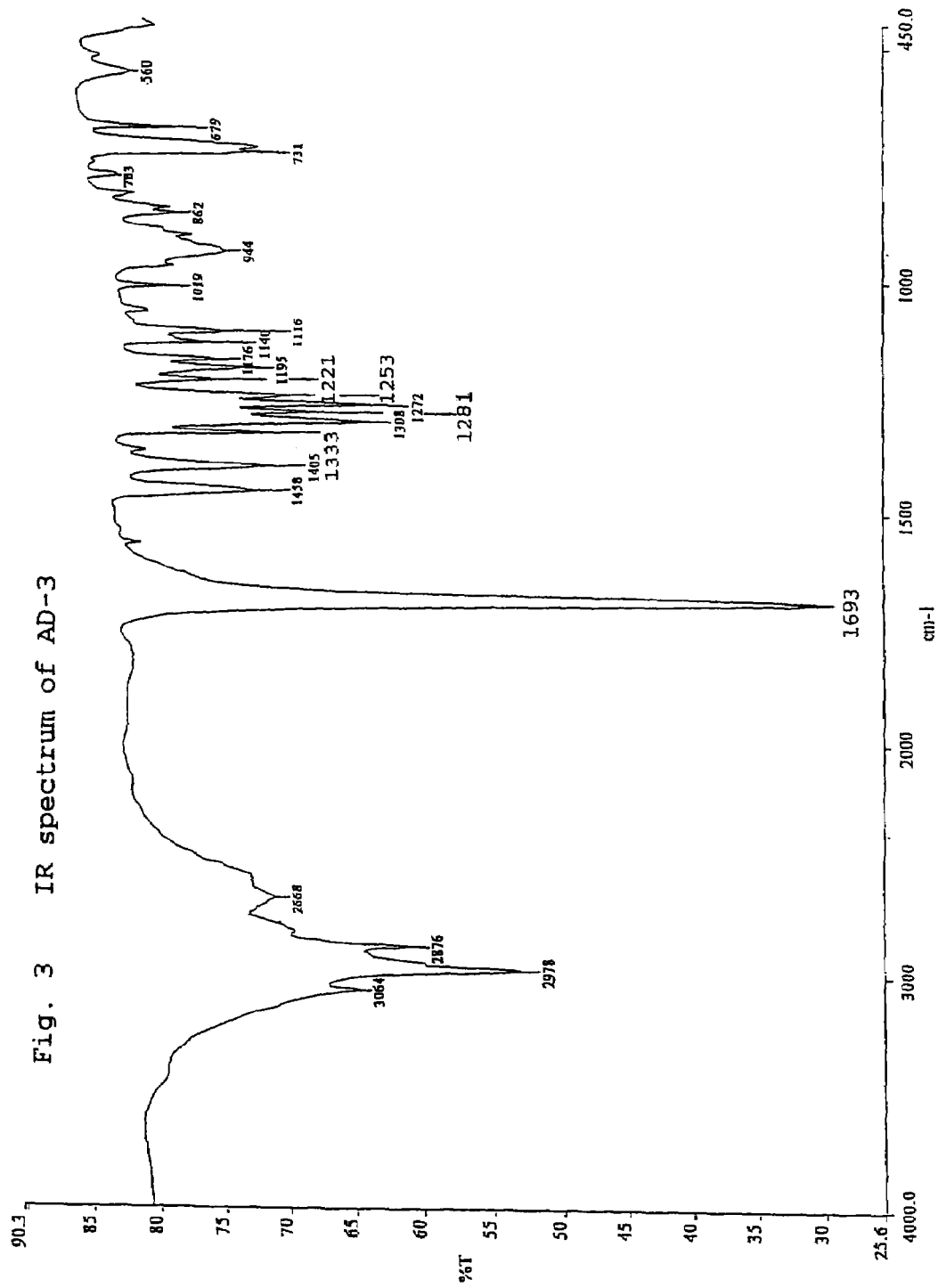
FIG. 3 shows an IR spectrum of a compounding agent (AD-3) for an antifouling paint, said compounding agent being used in an example of the invention or a comparative example.
Figure 4:
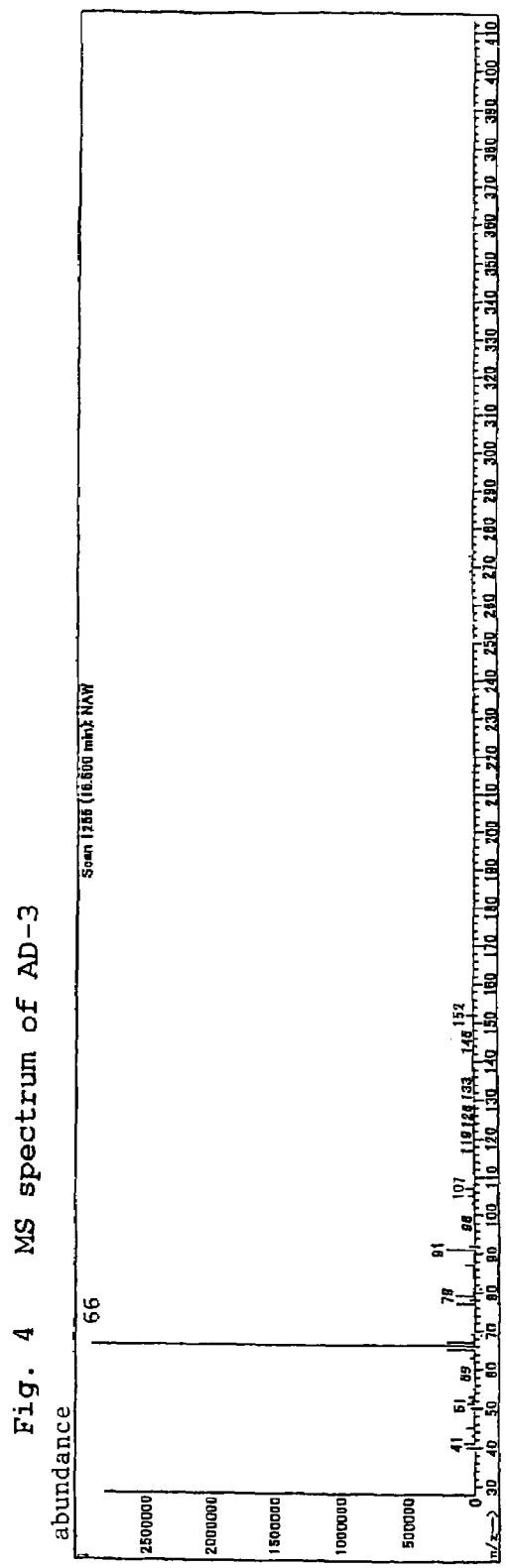
FIG. 4 shows a MS spectrum of a compounding agent (AD-3) for an antifouling paint, said compounding agent being used in an example of the invention or a comparative example.

An IR spectrum of the compounding agent (AD-3) for an antifouling paint is shown in FIG. 3, and a MS spectrum thereof is shown in FIG. 4.

This compounding agent (AD-3) for an antifouling paint corresponds to a cyclic carboxylic acid (compound A-2) represented by the aforesaid formula (2) and is the aforesaid isomer mixture. In case of this mixture, the same IR spectrum is obtained with good reproducibility.

(Preparation of Compounding Agent (AD-4) for Antifouling Paint)

In a reaction vessel equipped with a stirrer, a condenser and a heating or cooling jacket, 960 parts of alloocimene, 525 parts of methacrylic acid and 0.5 part of hydroquinone monomethyl ether were placed, and they were heated at 40° C. for 24 hours with stirring. Thereafter, the unreacted materials were distilled off under reduced pressure to obtain 220 parts of a brown viscous liquid compounding agent (AD-4) for an antifouling paint.

Figure 5:
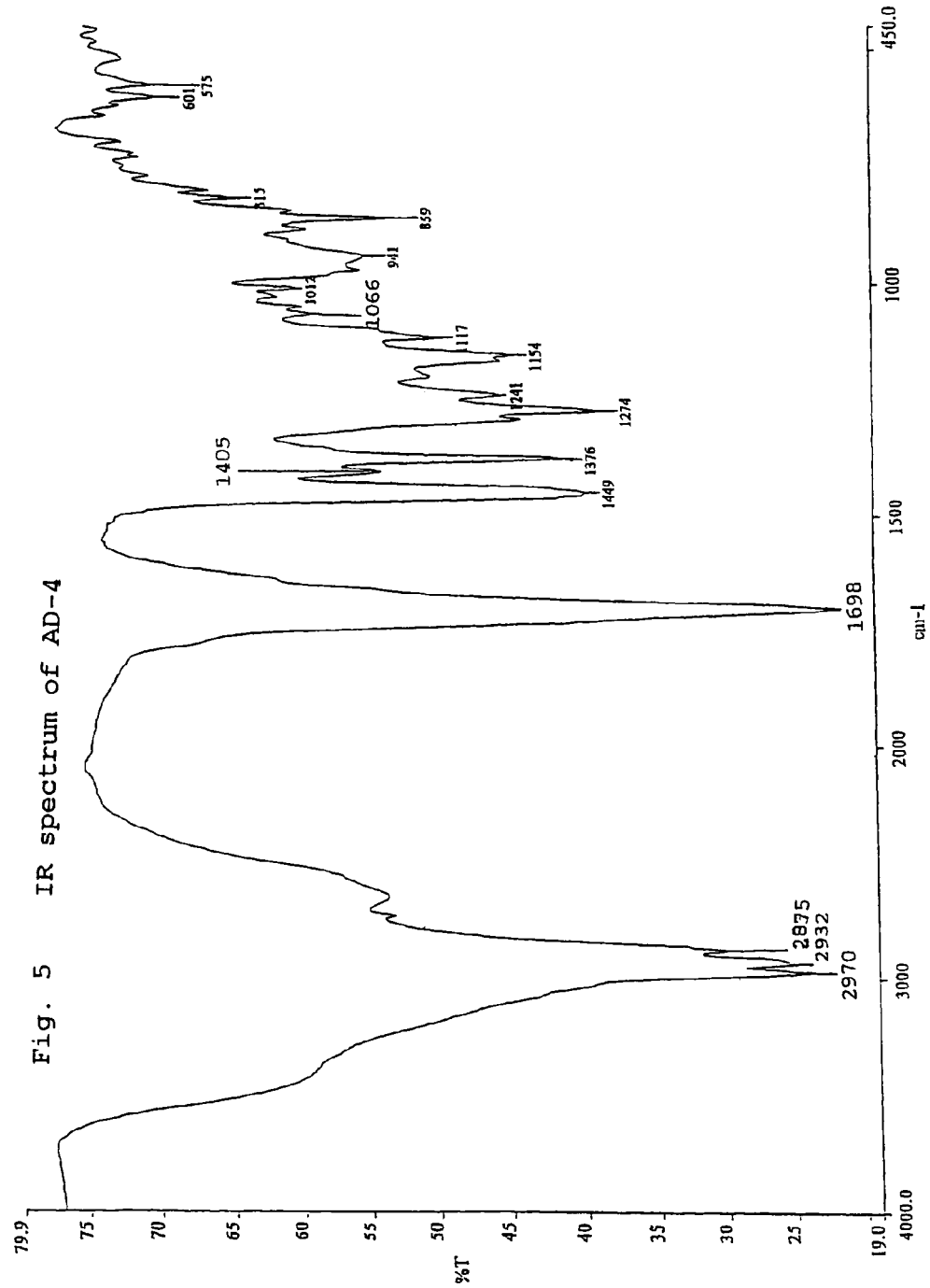
FIG. 5 shows an IR spectrum of a compounding agent (AD-4) for an antifouling paint, said compounding agent being used in an example of the invention or a comparative example.

An IR spectrum of the compounding agent (AD-4) for an antifouling paint is shown in FIG. 5.

This compounding agent (AD-4) for an antifouling paint corresponds to a cyclic carboxylic acid (compound A-3) represented by the aforesaid formula (3) (i.e., the following formula (3)) and is the aforesaid isomer mixture.

[Compound 34]

(3)

Compound A-3a (Mw: 222)    Compound A-3b (Mw: 222)

(Preparation of Compounding Agent (AD-5) for Antifouling Paint)

In a reaction vessel equipped with a stirrer, a condenser and a heating or cooling jacket, 1016 parts of alloocimene, 540 parts of methacrylic acid, 0.9 part of activated clay and 1.0 part of hydroquinone monomethyl ether were placed, and they were heated at 90° C. for 24 hours with stirring to complete reaction. Thereafter, the aimed product was purified (160 to 170° C./2 mmHg) by vacuum distillation to obtain 1055 g of a yellow transparent liquid compounding agent (AD-5) for an antifouling paint.

The compounding agent (AD-5) for an antifouling paint was then solidified by crystallinzation at room temperature.

A melting point of the thus crystallized compounding agent (AD-5) for an antifouling paint was measured by DSC, and as a result, it was 58° C.

Figure 6:
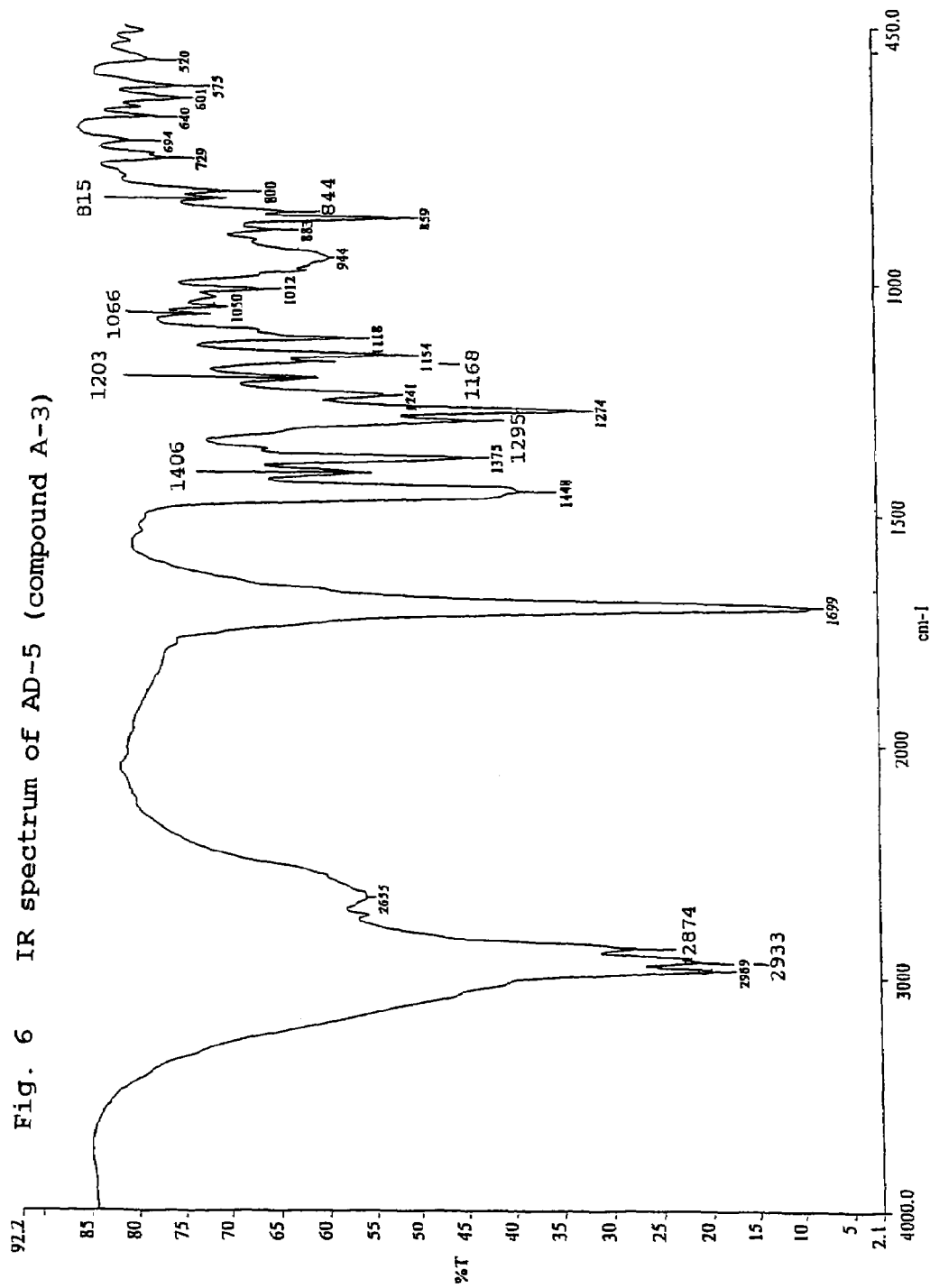
FIG. 6 shows an IR spectrum of a compounding agent (AD-5, compound A-3) for an antifouling paint, said compounding agent being used in an example of the invention or a comparative example.
Figure 7:
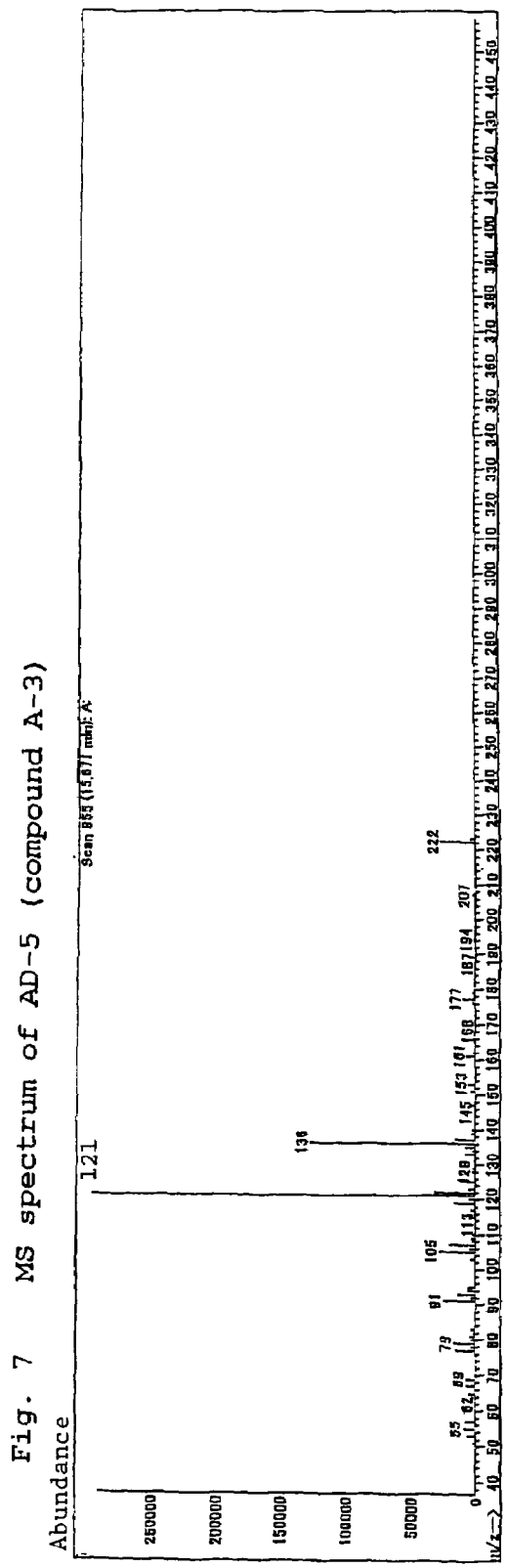
FIG. 7 shows a MS spectrum of a compounding agent (AD-5, compound A-3) for an antifouling paint, said compounding agent being used in an example of the invention or a comparative example.

An IR spectrum of the compounding agent (AD-5) for an antifouling paint is shown in FIG. 6, and a MS spectrum thereof is shown in FIG. 7.

This compounding agent (AD-5) for an antifouling paint corresponds to a cyclic carboxylic acid (compound A-3) represented by the aforesaid formula (3) and is the aforesaid isomer mixture.

(Preparation of Compounding Agent (AD-6) for Antifouling Paint)

In a reaction vessel equipped with a stirrer, a condenser and a heating or cooling jacket, 1030 parts of myrcene, 470 parts of methacrylic acid and 0.5 part of hydroquinone monomethyl ether were placed, and they were heated at 90° C. for 8 hours with stirring to complete reaction. Thereafter, the unreacted materials were distilled off under reduced pressure to obtain 890 parts of a brown viscous liquid compounding agent (AD-6) for an antifouling paint.

Figure 8:
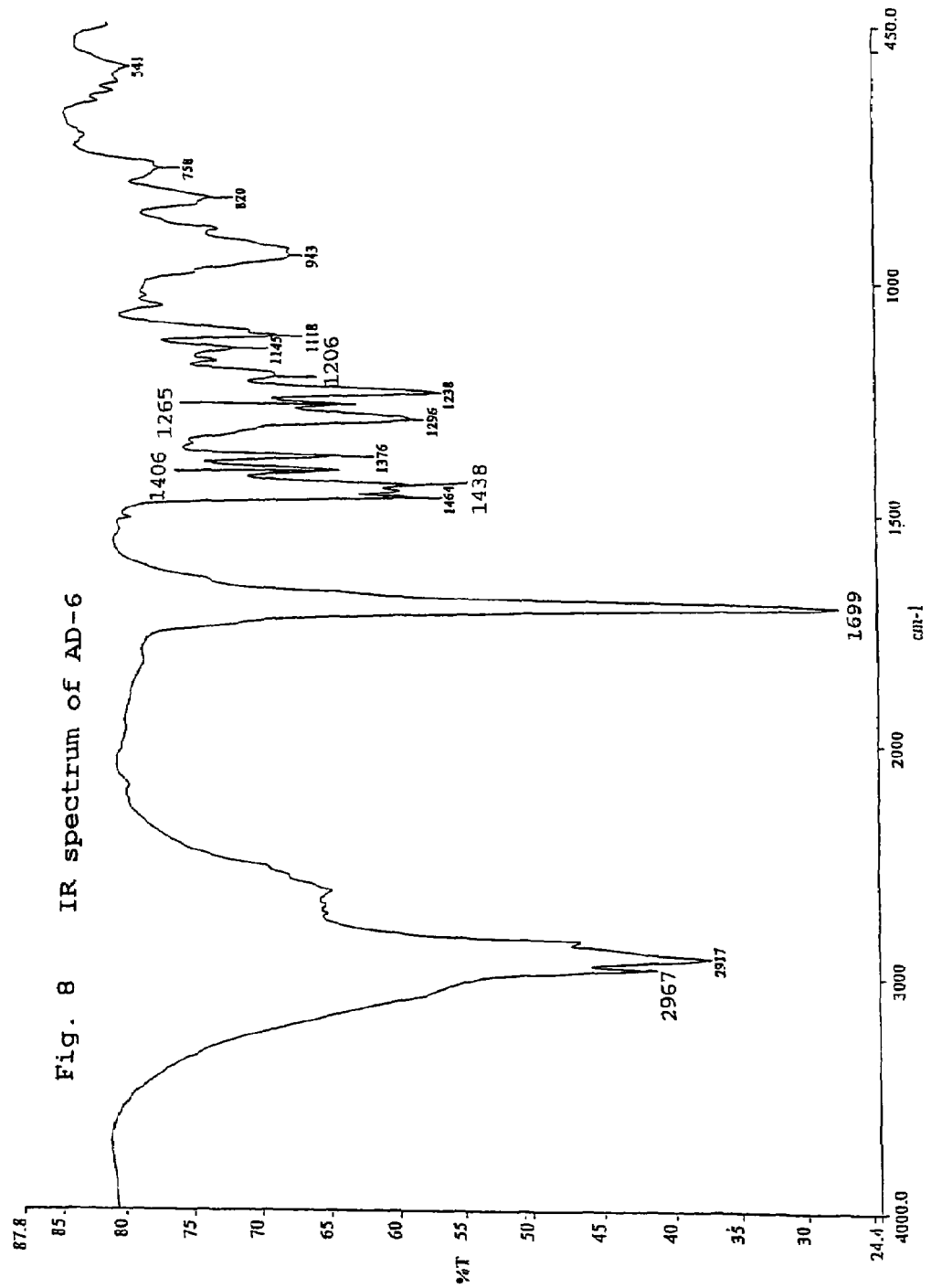
FIG. 8 shows an IR spectrum of a compounding agent (AD-6) for an antifouling paint, said compounding agent being used in an example of the invention or a comparative example.

An IR spectrum of the compounding agent (AD-6) for an antifouling paint is shown in FIG. 8.

This compounding agent (AD-6) for an antifouling paint corresponds to a cyclic carboxylic acid (compound A-5) represented by the aforesaid formula (5) (i.e., the following formula (5)) and is the aforesaid isomer mixture.

[Compound 35]

(5)

(5a)
Compound A-5a (Mw: 222)

(5b)
Compound A-5b (Mw: 222)

(Preparation of Compounding Agent (AD-7) for Antifouling Paint)

In a reaction vessel equipped with a stirrer, a condenser and a heating or cooling jacket, 1070 parts of myrcene, 506 parts of methacrylic acid, 0.9 part of activated clay and 1.0 part of hydroquinone monomethyl ether were placed, and they were heated at 90° C. for 16 hours with stirring to complete reaction. Thereafter, the aimed product was purified (160 to 170° C./2 mmHg) by vacuum distillation to obtain 861 parts of a yellow transparent liquid compounding agent (AD-7) for an antifouling paint.

Figure 9:
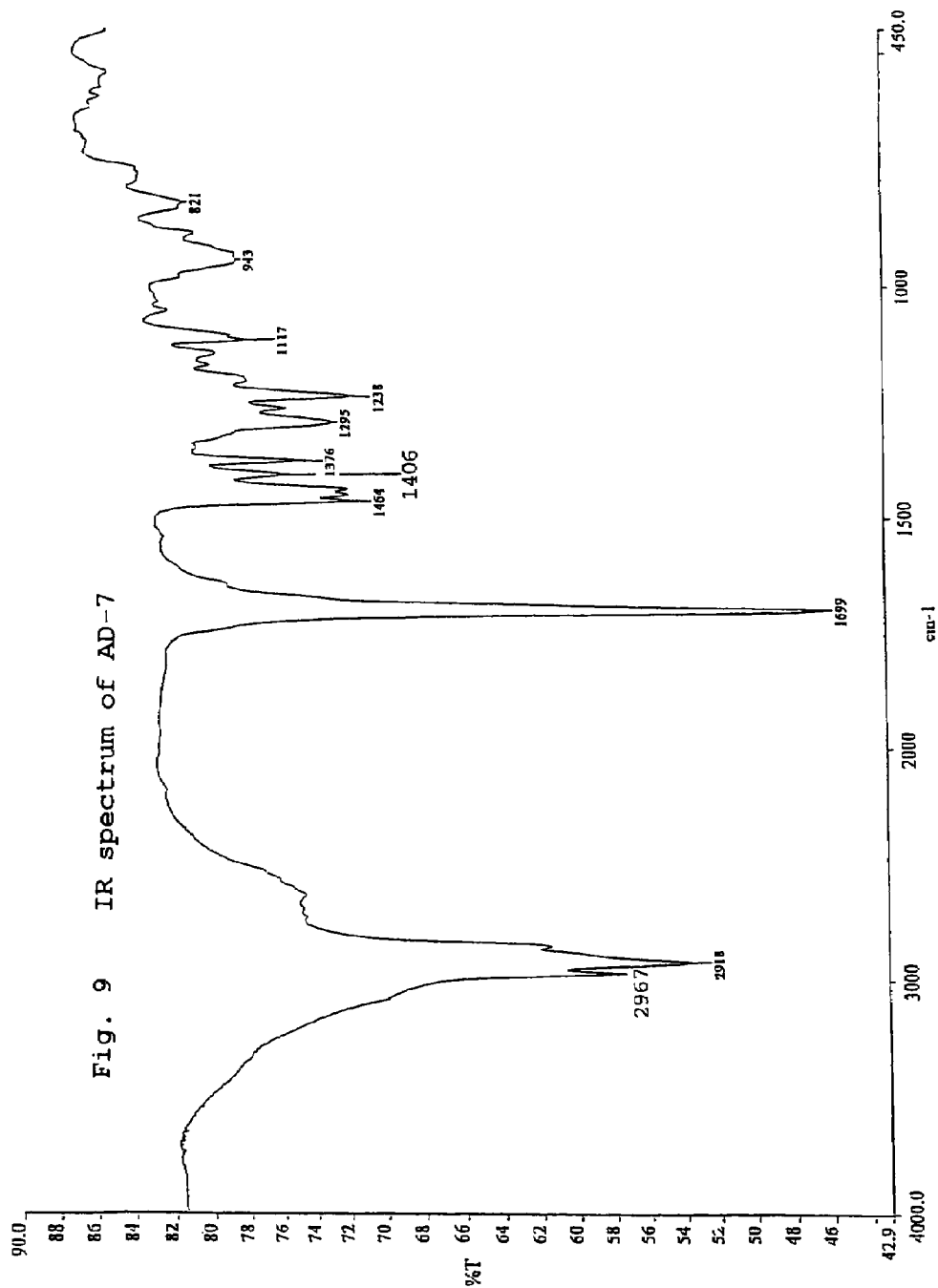
FIG. 9 shows an IR spectrum of a compounding agent (AD-7) for an antifouling paint, said compounding agent being used in an example of the invention or a comparative example.
Figure 10:
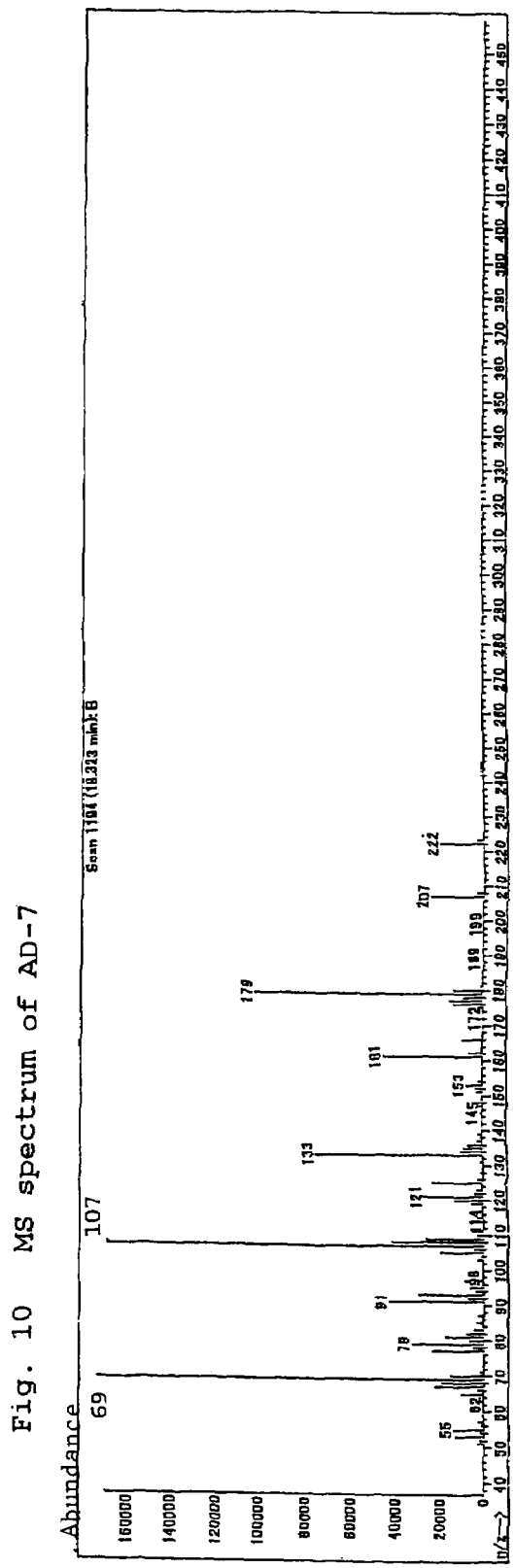
FIG. 10 shows a MS spectrum of a compounding agent (AD-7) for an antifouling paint, said compounding agent being used in an example of the invention or a comparative example.

An IR spectrum of the compounding agent (AD-7) for an antifouling paint is shown in FIG. 9, and a MS spectrum thereof is shown in FIG. 10.

This compounding agent (AD-7) for an antifouling paint corresponds to a cyclic carboxylic acid (compound A-5) represented by the aforesaid formula (5) and is the aforesaid isomer mixture.

(Preparation of Compounding Agent (AD-8) for Antifouling Paint)

In a reaction vessel equipped with a stirrer, a condenser and a heating or cooling jacket, 953 parts of alloocimene, 867 parts of monomethylmaleic acid and 1.0 part of hydroquinone monomethyl ether were placed, and they were heated at 40° C. for 24 hours with stirring to complete reaction. Thereafter, the unreacted materials were distilled off under reduced pressure to obtain 1450 parts of a yellow transparent liquid compounding agent (AD-8) for an antifouling paint.

Figure 11:
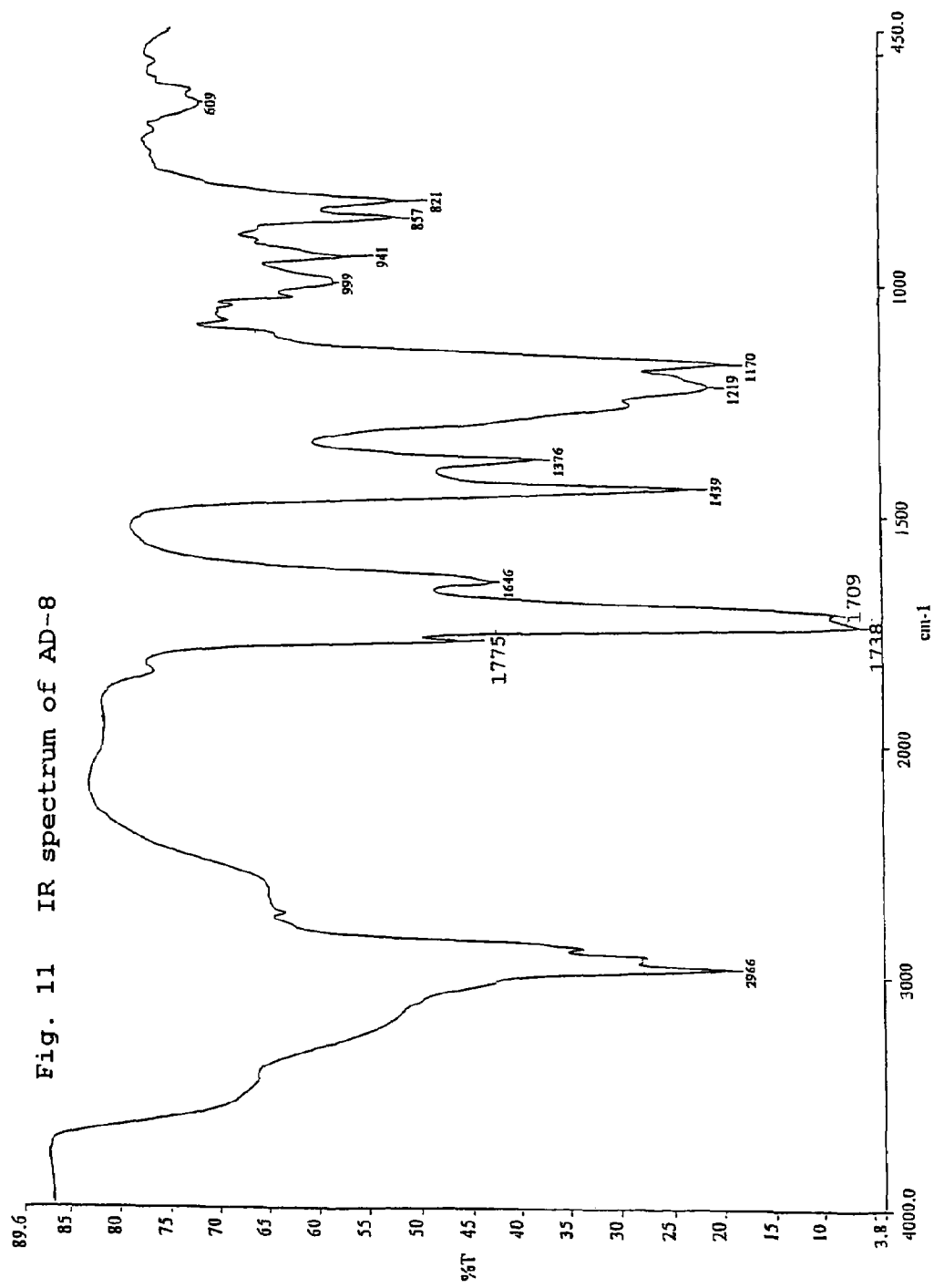
FIG. 11 shows an IR spectrum of a compounding agent (AD-8) for an antifouling paint, said compounding agent being used in an example of the invention or a comparative example.

An IR spectrum of the compounding agent (AD-8) for an antifouling paint is shown in FIG. 11, and a MS spectrum thereof is shown in FIG. 12.

This compounding agent (AD-8) for an antifouling paint corresponds to a cyclic carboxylic acid represented by the following formula (8) and is the aforesaid isomer mixture.

[Compound 36]

(8)

[Vg]
(8a)
(Me: methyl group)
(Mw:266)

[Vh]
(8b)
(Mw:266)

Preparation Examples of Copolymers (Preparation of Copolymer (S-1))

In a reaction vessel equipped with a stirrer, a condenser, a thermometer, a dropping device, a nitrogen feed pipe and a heating or cooling jacket, 100 parts of xylene were placed, and the xylene was heated in a stream of nitrogen under the temperature conditions of 85° C. with stirring. With maintaining the same temperature, a mixture of 50 parts of triisopropylsilyl acrylate, 50 parts of methyl methacrylate and 1 part of 2,2'-azobisisobutyronitrile as a polymerization initiator was dropwise added over a period of 2 hours by means of the dropping device. Thereafter, stirring was performed at the same temperature for 4 hours, then 0.4 part of 2,2'-azobisisobutyronitrile was added, and stirring was further performed at the same temperature for 4 hours to obtain a colorless transparent copolymer (S-1) solution.

The heating residue of the resulting copolymer (S-1) (heating residue after drying for 3 hours in a 105° C. hot air dryer) was 51.2% by weight, and the copolymer had a viscosity at 25° C. of 408 cps, a number-average molecular weight (Mn), as measured by GPC, of 6618 and a weight-average molecular weight (Mw) of 19434. The GPC measuring conditions are as follows.

(GPC Measuring Conditions)

Apparatus: HLC-8120GPC manufactured by Tosoh Corporation

Column: Super H2000+H4000 manufactured by Tosoh Corporation, 6 mm I.D., 15 cm

Eluting solution: THF (tetrahydrofuran)

Flow rate: 0.500 ml/min

Detector: RI

Column constant-temperature bath temperature: 40° C.

(Preparation of Copolymers (S-2) to (S-8))

Copolymers (S-2) to (S-8) were prepared in the same manner as above, except that the monomer components dropwise added for copolymerization in the preparation of the copolymer (S-1) were changed as shown in Table 1. Then, property values of the copolymers (solutions) were measured in the same manner as above.

The results are shown in Table 1.

(Preparation of Copolymer (S-9))

Preparation of Monomer (K-1)

In a reaction vessel equipped with a stirrer, a condenser, a thermometer, a dropping device and a heating or cooling jacket, 85.4 parts of propylene glycol monomethyl ether (solvent) and 40.7 parts of zinc oxide were placed, and they were heated to 75° C. with stirring. Thereafter, a mixture of 43.1 parts of methacrylic acid, 36.1 parts of acrylic acid and 5.0 parts of water was dropwise added at the same temperature over a period of 3 hours by means of the dropping device. Then, stirring was performed at the same temperature for 2 hours, and thereafter, 36.0 parts of propylene glycol monomethyl ether were added to complete reaction, whereby a monomer solution (K-1) was obtained.

Preparation of Copolymer (S-9)

In a reaction vessel equipped with a stirrer, a condenser, a thermometer, a dropping device, a nitrogen feed pipe and a heating or cooling jacket, 15.0 parts of propylene glycol monomethyl ether, 57.0 parts of xylene and 4 parts of ethyl acrylate were placed, and they were heated in a stream of nitrogen under the temperature conditions of 100° C. with stirring. With maintaining the same temperature, a mixture of 1.0 part of methyl methacrylate, 66.2 parts of ethyl acrylate, 5.4 parts of 2-methoxyethyl acrylate, 52 parts of the monomer solution (K-1) prepared above, 10 parts of xylene, 1.0 part of an α-methylstyrene dimer, 2.5 parts of 2,2'-azobisisobutyronitrile as a polymerization initiator and 7.0 parts of 2,2'-azobismethylbutyronitrile as a polymerization initiator was dropwise added over a period of 6 hours by means of the dropping device. Thereafter, a mixture of 0.5 part of t-butyl peroctoate and 7.0 parts of xylene was dropwise added, then stirring was performed for 1.5 hours under heating at the same temperature, and thereafter 4.4 parts of xylene were added to obtain a light yellow transparent copolymer (S-9) solution.

The heating residue of the resulting copolymer (S-9) solution (heating residue after drying for 3 hours in a 105° C. hot air dryer) was 45.6% by weight, and the copolymer had a Gardner viscosity at 25° C. of Y. (The copolymer was adsorbed in the column, so that accurate molecular weight measurement of the copolymer was impossible.)

Preparation Examples of Antifouling Paint Compositions

Examples 1 to 24, Comparative Examples 1 to 7

The compounding ingredients in the compounding ratios shown in Table 2 to Table 4 were placed in a paint shaker containing glass beads as media (mixing dispersion media), shaken for 2 hours and then filtered through a 100-mesh filter to obtain desired antifouling paint compositions.

After the antifouling paint compositions were stored for 2 months at ordinary temperature, storage stability was evaluated.

The evaluation results are shown in Table 2 to Table 4.

Storage Stability

Evaluation of storage stability was carried out in the following manner. A viscosity (Ku value determined by Stormer's viscometer at 25° C.) of the paint (paint composition) was measured immediately after preparation of the paint and after storage for 2 months at ordinary temperature, then the measured values were compared, and an increase in viscosity was evaluated based on the following criteria.

(Evaluation Criteria)

5: An increase in viscosity is less than 10.

4: An increase in viscosity is not less than 10 and less than 20.

3: An increase in viscosity is not less than 20 and less than 30.

2: An increase in viscosity is not less than 30.

1: Because of bad fluidity, measurement of Ku value is impossible.

Further, static antifouling property, erodibility and appearance of coating films formed from the antifouling paint compositions were evaluated in the following manner.

The results are shown in Table 2 to Table 4.

Static Antifouling Test

A sandblasted steel plate having a size of 100 mm×300 mm×2 mm (thickness) was coated with an epoxy type zinc-rich primer so that the dry film thickness should become 20 µm. On the next day, the steel plate was further coated with a modified epoxy type anticorrosion paint so that the dry film thickness should become 200 µm. On the next day, the steel plate was furthermore coated with the antifouling paint composition under test shown in Table 2 to table 4 so that the dry film thickness should become 100 µm, whereby a test plate was obtained.

The test plate was suspended at the depth of about 1 m from a test raft set up in Nagasaki Bay, and after a lapse of 24 months, an area of the test plate where macro organisms (barnacle, serpula, etc.) had adhered was evaluated.

(Evaluation Criteria)

5: Nothing adheres.

4: The adhesion area is less than 5%.

3: The adhesion area is not less than 5% and less than 15%.

2: The adhesion area is not less than 15% and less than 40%.

1: The adhesion area is not less than 40%.

Evaluation of Erodibility and Appearance of Coating Film (I) Evaluation of Erodibility of Coating Film A sandblasted steel disc plate having a diameter of 300 mm and a thickness of 3 mm was coated with an epoxy type zinc-rich primer so that the dry film thickness should become 20 µm. On the next day, the steel plate was further coated with a modified epoxy type anticorrosion paint so that the dry film thickness should become 200 µm, followed by drying indoors for 7 days.

Thereafter, the sandblasted steel disc plate was radially coated with the antifouling paint composition under test in the radius direction from the center of the disc plate by means of an applicator having a gap of 500 µm, whereby a test plate was obtained. (This applicator is an application device which is a box container with legs having a leg length (gap) of 500 µm, at the bottom of said container being provided with a paint outlet. By placing the container containing a paint on a steel plate that is a coating object and then moving it on the steel plate in a given direction to allow the paint to run out from the outlet, painting (coating) can be carried out to give a coating thickness corresponding to the leg length (gap).)

The test plate was fixed to a motor and continuously rotated for 2 months at a circumferential velocity of 15 knots in a constant-temperature bath containing seawater of 25° C., and erodibility (decrease in film thickness) in the vicinity of the circumference was measured.

Further, appearance of the coating film in the measurement of decrease in film thickness was visually observed and evaluated based on the following criteria.

(Evaluation Criteria)

5: Nothing abnormal is observed on the coating film.

4: Fine cracks are observed on a part of the coating film.

3: Fine cracks are observed on the whole of the coating film.

2: Conspicuous cracks are observed on a part of the coating film.

1: Conspicuous cracks are observed on the whole of the coating film.

Compound names and manufacturing or selling companies of the compounding ingredients indicated by the trade names shown in the following tables are as follows.
(1) WW rosin: WW rosin made in China
(2) tall oil rosin: trade name "Hartall R—X" (available from Harima Chemicals, Inc.)
(3) copper rhodanide: available from Nihon Kagaku Sangyo Co., Ltd.
(4) Anhydrous gypsum D-1: available from Noritake Co., Ltd., IIICaSO$_4$, white powder, mean particle diameter 15 μm
(5) Disperon 4200-20: polyethylene oxide wax, available from Kusumoto Chemicals, Ltd., 20% xylene paste
(6) Disperon A630-20X: aliphatic amide wax, available from Kusumoto Chemicals, Ltd., 20% xylene paste

TABLE 1

| Type of polymer | Compounding ingredients, part(s) by weight | | S-1 | S-2 | S-3 | S-4 | S-5 | S-6 | S-7 | S-8 |
|---|---|---|---|---|---|---|---|---|---|---|
| Solvent | Xylene | | 100 | 100 | 100 | 100 | 100 | 100 | 100 | 100 |
| Ingredient dropped | Triisopropylsilyl acrylate | | 50 | 50 | 40 | 50 | 65 | 50 | 50 | 40 |
| | Tri-n-butylsilyl methacrylate | | | | | | | 5 | | |
| | Methyl methacrylate | | 50 | 45 | 55 | 45 | 30 | 45 | 45 | 55 |
| | 2-Methoxyethyl acrylate | | | 5 | | | | | | |
| | Ethyl acrylate | | | | 5 | 5 | 5 | | | |
| | 2-Hydroxybutyl acrylate | | | | | | | | 5 | |
| | Poly(n = 4)ethylene glycol bis(3-mercaptopropionate) | | | | | | | | | 5 |
| | 2,2'-Azobisisobutyronitrile (initial stage) | | 1 | 1 | 1 | 1 | 1 | 1 | 1 | 1 |
| | | Total | 201 | 201 | 201 | 201 | 201 | 201 | 201 | 201 |
| Additional ingredient | 2,2'-Azobisisobutyronitrile (later stage) | | 0.4 | 0.4 | 0.4 | 0.4 | 0.4 | 0.4 | 0.4 | 0.4 |
| Properties of product | Heating residue (wt %) | | 51.2 | 50.1 | 49.5 | 50.8 | 50.1 | 50.7 | 50.9 | 50.5 |
| | Viscosity (cps/25° C.) | | 408 | 111 | 364 | 343 | 335 | 264 | 297 | 72 |
| | GPC measured value | Mn | 6618 | 4449 | 4998 | 4596 | 5113 | 5223 | 5167 | 2748 |
| | | Mw | 19434 | 15773 | 16229 | 16049 | 16038 | 19196 | 17963 | 5603 |
| | | Mw/Mn | 2.9 | 3.5 | 3.2 | 3.5 | 3.1 | 3.7 | 3.5 | 2.0 |

TABLE 2

| | | Examples | | | | | | | | | |
|---|---|---|---|---|---|---|---|---|---|---|---|
| Compounding ingredient (part(s) by weight) | | 1 | 2 | 3 | 4 | 5 | 6 | 7 | 8 | 9 | 10 |
| Copolymer solution | S-1 | 22 | | | | | | | | | |
| | S-2 | | 16 | | | | | | | | |
| | S-3 | | | 22 | 18 | 22 | 18 | | | | |
| | S-4 | | | | | | | 22 | 22 | 22 | 22 |
| | S-5 | | | | | | | | | | |
| | S-6 | | | | | | | | | | |
| | S-7 | | | | | | | | | | |
| | S-8 | | | | | | | | | | |
| | S-9 | | | | | | | | | | |
| Compounding agent for antifouling paint | AD-1 | 2 | | | | | | | | | |
| | AD-2 | | 5 | | | | | | | | |
| | AD-3 | | | 2 | 4 | | | | | | |
| | AD-4 | | | | | 2 | 4 | 2 | | | |
| | AD-5 | | | | | | | | 2 | | |
| | AD-6 | | | | | | | | | 2 | |
| | AD-7 | | | | | | | | | | 2 |
| WW rosin | | | | | | | | | | | |
| Tall oil rosin | | | | | | | | | | | |
| Antifouling agent | Cuprous oxide | 45 | 45 | 45 | 45 | 45 | 45 | 45 | 45 | 45 | 45 |
| | 2-Pyridinethiol-1-oxide copper salt | 3 | 3 | 3 | 3 | 3 | 3 | 3 | 3 | 3 | 3 |
| | 4,5-Dichloro-2-n-octylisothiazoline-3-one | | | | | | | | | | |
| | 2,4,5,6-Tetrachloroisophthalonitrile | | | | | | | | | | |
| | 2-Methylthio-4-t-butylamino-6-cyclopropylamino-s-triazine | | | | | | | | | | |
| | N-(2,4,6-trichlorophenyl)maleimide | | | | | | | | | | |
| | Pyridine-triphenylborane | | | | | | | | | | |
| | Copper rhodanide | | | | | | | | | | |
| Titanium white | | 2 | 2 | 2 | 2 | 2 | 2 | 2 | 2 | 2 | 2 |
| Red iron oxide | | | | | | | | | | | |

TABLE 2-continued

|  | | Examples | | | | | | | | | |
| --- | --- | --- | --- | --- | --- | --- | --- | --- | --- | --- | --- |
| Compounding ingredient (part(s) by weight) | | 1 | 2 | 3 | 4 | 5 | 6 | 7 | 8 | 9 | 10 |
| Anhydrous gypsum D-1 | | 1 | 1 | 1 | 1 | 1 | 1 | 1 | 1 | 1 | 1 |
| zinc white | | 6 | 6 | 6 | 6 | 6 | 6 | 6 | 6 | 6 | 6 |
| Talc | | | | | | | | | | | |
| Disperon 4200-20 | | 1.5 | 1.5 | 1.5 | 1.5 | 1.5 | 1.5 | 1.5 | 1.5 | 1.5 | 1.5 |
| Disperon A-603-20X | | 4 | 4 | 4 | 4 | 4 | 4 | 4 | 4 | 4 | 4 |
| Xylene | | 13.5 | 16.5 | 13.5 | 15.5 | 13.5 | 15.5 | 13.5 | 13.5 | 13.5 | 13.5 |
| | Total | 100 | 100 | 100 | 100 | 100 | 100 | 100 | 100 | 100 | 100 |
| Evaluation results | Storage stability | 5 | 5 | 5 | 5 | 5 | 5 | 5 | 5 | 5 | 5 |
| | Antifouling property | 4 | 4 | 4 | 5 | 5 | 5 | 5 | 5 | 5 | 5 |
| | Erodibility | 8 | 9 | 11 | 15 | 12 | 16 | 15 | 16 | 13 | 15 |
| | Appearance of coating film | 5 | 5 | 5 | 4 | 5 | 5 | 5 | 5 | 5 | 5 |

TABLE 3

|  | | Example | | | | | | | | | |
| --- | --- | --- | --- | --- | --- | --- | --- | --- | --- | --- | --- |
| Compounding ingredient (part(s) by weight) | | 11 | 12 | 13 | 14 | 15 | 16 | 17 | 18 | 19 | 20 |
| Copolymer solution | S-1 | | | | | | | | | 18 | |
| | S-2 | | | | | | | | | | |
| | S-3 | | | | | | | | | | |
| | S-4 | | | | | | | | | | 18 |
| | S-5 | | 22 | 18 | 22 | | | | | | |
| | S-6 | | | | | 22 | | | | | |
| | S-7 | | | | | | 22 | | | | |
| | S-8 | | | | | | | 22 | 18 | | |
| | S-9 | 35 | | | | | | | | | |
| Compounding agent for antifouling paint | AD-1 | | | | | | | | | | |
| | AD-2 | | | | | | | | | | |
| | AD-3 | | | | | | | | | | |
| | AD-4 | | | | | | | | | | |
| | AD-5 | 2 | 2 | 4 | | | 2 | 2 | 4 | | 4 |
| | AD-6 | | | | | 2 | | | | 4 | |
| | AD-7 | | | | 2 | | | | | | |
| WW rosin | | | | | | | | | | | |
| Tall oil rosin | | | | | | | | | | | |
| Antifouling agent | Cuprous oxide | 45 | 45 | 45 | 45 | 45 | 45 | 45 | 45 | 45 | 45 |
| | 2-Pyridinethiol-1-oxide copper salt | 3 | 3 | 3 | 3 | 3 | | 3 | 3 | | |
| | 4,5-Dichloro-2-n-octylisothiazoline-3-one | | | | | | 3 | | | 3 | |
| | 2,4,5,6-Tetrachloroisophthalonitrile | | | | | | | | | | 5 |
| | 2-Methylthio-4-t-butylamino-6-cyclopropylamino-s-triazine | | | | | | | | | | |
| | N-(2,4,6-trichlorophenyl)maleimide | | | | | | | | | | |
| | Pyridine-triphenylborane | | | | | | | | | | |
| | Copper rhodanide | | | | | | | | | | |
| Titanium white | | 2 | 2 | 2 | 2 | 2 | 2 | 2 | 2 | 2 | 2 |
| Red iron oxide | | | | | | | | | | | |
| Anhydrous gypsum D-1 | | 1 | 1 | 1 | 1 | 1 | 1 | 1 | 1 | 1 | 1 |
| zinc white | | 6 | 6 | 6 | 6 | 6 | 6 | 6 | 6 | 6 | 6 |
| Talc | | | | | | | | | | | |
| Disperon 4200-20 | | 1.5 | 1.5 | 1.5 | 1.5 | 1.5 | 1.5 | 1.5 | 1.5 | 1.5 | 1.5 |
| Disperon A-603-20X | | 4 | 4 | 4 | 4 | 4 | 4 | 4 | 4 | 4 | 4 |
| Xylene | | 0.5 | 13.5 | 15.5 | 13.5 | 13.5 | 13.5 | 13.5 | 15.5 | 15.5 | 13.5 |
| | Total | 100 | 100 | 100 | 100 | 100 | 100 | 100 | 100 | 100 | 100 |
| Evaluation results | Storage stability | 5 | 5 | 5 | 5 | 5 | 5 | 5 | 5 | 5 | 5 |
| | Antifouling property | 4 | 5 | 5 | 5 | 5 | 5 | 5 | 5 | 5 | 5 |
| | Erodibility | 31 | 20 | 28 | 19 | 18 | 17 | 25 | 30 | 10 | 18 |
| | Appearance of coating film | 5 | 5 | 5 | 5 | 5 | 5 | 5 | 5 | 5 | 5 |

TABLE 4

| Compounding ingredient (part(s) by weight) | | Example | | | | Comparative Example | | | | | | |
|---|---|---|---|---|---|---|---|---|---|---|---|---|
| | | 21 | 22 | 23 | 24 | 1 | 2 | 3 | 4 | 5 | 6 | 7 |
| Copolymer solution | S-1 | | | | | 26 | | | | | | |
| | S-2 | | | | | | 26 | | | | | |
| | S-3 | | | | | | | 26 | 22 | 22 | | |
| | S-4 | | | | 22 | | | | | | | |
| | S-5 | | 22 | 30 | | | | | | | | |
| | S-6 | | | | | | | | | | | |
| | S-7 | 18 | | | | | | | | | | |
| | S-8 | | | | | | | | | | | |
| | S-9 | | | | | | | | | | 40 | 35 |
| Compounding agent for antifouling paint | AD-1 | | | | | | | | | | | |
| | AD-2 | | | | | | | | | | | |
| | AD-3 | | | | | | | | | | | |
| | AD-4 | | | | | | | | | | | |
| | AD-5 | | 2 | 6 | 2 | | | | | | | |
| | AD-6 | | | | | | | | | | | |
| | AD-7 | 4 | | | | | | | | | | |
| WW rosin | | | | | | | | | | 2 | | 2 |
| Tall oil rosin | | | | | | | | | | 2 | | |
| Antifouling agent | Cuprous oxide | 45 | 45 | | 50 | 45 | 45 | 45 | 45 | 45 | 40 | 40 |
| | 2-Pyridinethiol-1-oxide copper salt | | | | 1 | 3 | 3 | 3 | 3 | 3 | | |
| | 4,5-Dichloro-2-n-octylisothiazoline-3-one | | | | 2 | | | | | | 3 | 3 |
| | 2,4,5,6-Tetrachloroisophthalonitrile | | | | | | | | | | | |
| | 2-Methylthio-4-t-butylamino-6-cyclopropylamino-s-triazine | 5 | | | | | | | | | | |
| | N-(2,4,6-trichlorophenyl)maleimide | | 5 | | | | | | | | | |
| | Pyridine-triphenylborane | | | 5 | | | | | | | | |
| | Copper rhodanide | | | 15 | | | | | | | | |
| Titanium white | | 2 | 2 | 2 | 1 | 2 | 2 | 2 | 2 | 2 | 2 | 2 |
| Red iron oxide | | | | 2 | 1 | | | | | | | |
| Anhydrous gypsum D-1 | | 1 | 1 | 1 | 1 | 1 | 1 | 1 | 1 | 1 | | |
| zinc white | | 6 | 6 | 6 | | 6 | 6 | 6 | 6 | 6 | 6 | 6 |
| Talc | | | | 2 | | | | | | | | |
| Disperon 4200-20 | | 1.5 | 1.5 | 1.5 | 1.5 | 1.5 | 1.5 | 1.5 | 1.5 | 1.5 | 1.5 | 1.5 |
| Disperon A-603-20X | | 4 | 4 | 4 | 4 | 4 | 4 | 4 | 4 | 4 | 4 | 4 |
| Xylene | | 13.5 | 11.5 | 25.5 | 14.5 | 11.5 | 11.5 | 11.5 | 13.5 | 13.5 | 3.5 | 6.5 |
| | Total | 100 | 100 | 100 | 100 | 100 | 100 | 100 | 100 | 100 | 100 | 100 |
| Evaluation results | Storage stability | 5 | 5 | 5 | 5 | 5 | 5 | 5 | 5 | 5 | 5 | 5 |
| | Antifouling property | 5 | 5 | 5 | 5 | 1 | 1 | 1 | 3 | 2 | 1 | 2 |
| | Erodibility | 25 | 18 | 39 | 14 | 4 | 5 | 5 | 7 | 6 | 17 | 20 |
| | Appearance of coating film | 5 | 5 | 5 | 5 | 5 | 5 | 5 | 4 | 3 | 5 | 5 |

The invention claimed is:

1. A novel cycloalkenylcarboxylic acid represented by the following formula [V] or a salt thereof:

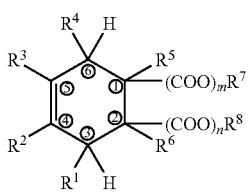

[V]

wherein $R^1$ is a 3-methyl-2-butenyl group or a 2-methyl-1-propenyl group, when $R^1$ is a 3-methyl-2-butenyl group, $R^2$ is a methyl group and $R^3$ and $R^4$ are each a hydrogen atom, when $R^1$ is a 2-methyl-1-propenyl group, $R^2$ is a hydrogen atom and $R^3$ and $R^4$ are each a methyl group, $R^5$ and $R^6$ are each a hydrogen atom or an alkyl group of 1 to 10 carbon atoms, m and n are each a number of 0 or 1 (with the proviso that it does not occur that m and n are 0 at the same time), $R^7$ and $R^8$ are each a hydrogen atom or a hydrocarbon group, when m is 0, $R^7$ is a hydrogen atom, when m is 1, $R^7$ is a hydrogen atom or a hydrocarbon group, when n is 0, $R^8$ is a hydrogen atom, when n is 1, $R^8$ is a hydrogen atom or a hydrocarbon group, with the proviso that $R^7$ and $R^8$ are not both hydrocarbon groups, when $R^1$ is a 2-methyl-1-propenyl group, $R^2$ is a hydrogen atom, $R^3$ and $R^4$ are each a methyl group and m=1, n=0, $R^5$ is an alkyl group of 1 to 10 carbon atoms, $R^6$, $R^7$ and $R^8$ are each a hydrogen atom, and when $R^1$ is a 2-methyl-1-propenyl group, $R^2$ is a hydrogen atom, $R^3$ and $R^4$ are each a methyl group and m=0, n=1, $R^6$ is an alkyl group of 1 to 10 carbon atoms, $R^5$, $R^7$ and $R^8$ are each a hydrogen atom.

2. The cycloalkenylcarboxylic acid or the salt thereof as claimed in claim 1, wherein the cycloalkenylcarboxylic acid represented by the formula [V] is represented by the following formula [Va], [Vb], [Vc], [Vd], [Vg] or [Vh], in said formulas, a hydrogen atom bonded to a carbon atom being omitted;

[Va]
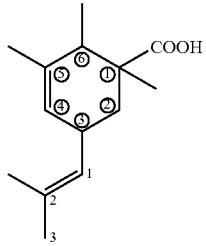

[Vb]
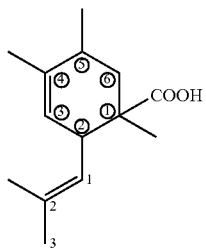

[Vc]
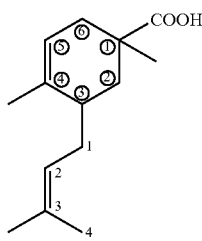

[Vd]
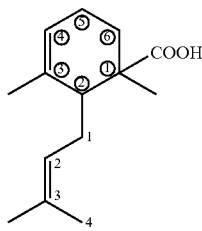

[Ve]
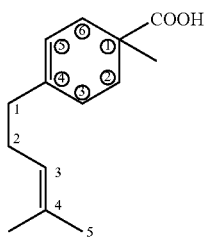

[Vf]
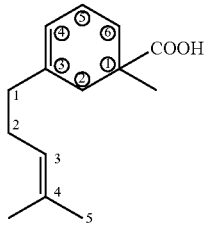

[Vg]
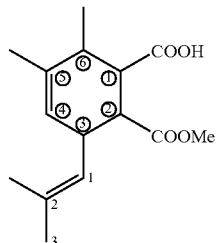

[Vh]
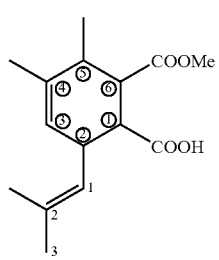

[VIa]
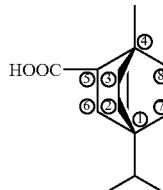

[VIb]
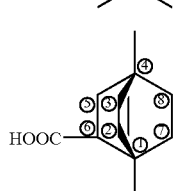

[VIc]
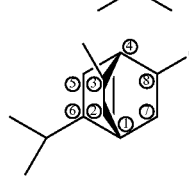

[VId]
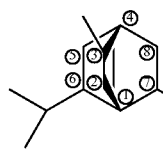

wherein Me is a methyl group.

3. A process for preparing the cycloalkenylcarboxylic acid of claim 1, comprising reacting at least one terpene-based diene compound (conjugated diene compound) selected from the group consisting of alloocimene, ocimene, myrcene, α-terpinene and α-phellandrene and at least one unsaturated carboxylic acid selected from α,β-unsaturated monocarboxylic acids and monoesters of α,β-unsaturated dicarboxylic acids.

4. A compounding agent for an antifouling paint comprising one or more substances selected from the group consisting of a cyclic carboxylic acid formed by the addition reaction of an unsaturated carboxylic acid with a conjugated diene compound, a derivative of the cyclic carboxylic acid (except a metal salt), the metal salt of the cyclic carboxylic acid, and the metal salt of a derivative of the cyclic carboxylic acid, wherein the cyclic carboxylic acid is the cycloalkenylcarboxylic acid or the salt thereof of claim 1.

5. An antifouling paint composition comprising:
(A) a compounding agent for an antifouling paint, comprising one or more substances selected from the group consisting of a cyclic carboxylic acid formed by the addition reaction of an unsaturated carboxylic acid with a conjugated diene compound, a derivative of the cyclic carboxylic acid (except a metal salt), a metal salt of the cyclic carboxylic acid, and a metal salt of a derivative of the cyclic carboxylic acid, and
(B) a copolymer for a self-polishing antifouling paint.

6. The antifouling paint composition as claimed in claim 5, further comprising (C) an antifouling agent.

7. The antifouling paint composition as claimed in claim 6, wherein copper or a copper compound is contained as the antifouling agent (C).

8. The antifouling paint composition as claimed in claim 6, wherein an organic antifouling agent is contained as the antifouling agent (C).

9. The antifouling paint composition as claimed in claim 5, wherein the copolymer (B) for a self-polishing antifouling paint is a polymerizable unsaturated carboxylic acid hydroxy metal salt-based copolymer.

10. The antifouling paint composition as claimed in claim 5, wherein the copolymer (B) for a self-polishing antifouling paint is a copolymer derived from a polymerizable unsaturated carboxylic acid hydroxy metal compound represented by the following formula [I]:

$$R^1\text{—COO—M—OH} \qquad [I]$$

wherein $R^1$ is an unsaturated bond-containing organic group of $CH_2=C(CH_3)$—, $CH_2=CH$—, $HOOC$—$CH=CH$— or $HOOC$—$CH=C(CH_3)$—, —$COOH$, or a metal salt or an ester thereof, and M is a metal atom.

11. The antifouling paint composition as claimed in claim 5, wherein the copolymer (B) for a self-polishing antifouling paint is a copolymer derived from a (meth)acrylic acid hydroxy metal salt.

12. The antifouling paint composition as claimed in claim 5, wherein the copolymer (B) for a self-polishing antifouling paint is a copolymer derived from a (meth)acrylic acid hydroxy zinc salt or copper salt.

13. The antifouling paint composition as claimed in claim 5, wherein the copolymer (B) for a self-polishing antifouling paint is a polymerizable unsaturated carboxylic acid metal compound-based copolymer derived from a polymerizable unsaturated carboxylic acid metal compound containing no hydroxyl group bonded to a metal atom.

14. The antifouling paint composition as claimed in claim 5, wherein the copolymer (B) for a self-polishing antifouling paint is a copolymer derived from a polymerizable unsaturated carboxylic acid metal compound represented by the following formula [II]:

$$R^1\text{—COO—M—L}_n \qquad [II]$$

wherein $R^1$ is an unsaturated bond-containing organic group of $CH_2=C(CH_3)$—, $CH_2=CH$—, $HOOC$—$CH=CH$— or $HOOC$—$CH=C(CH_3)$—, —$COOH$, or a metal salt or an ester thereof, M is a metal atom, L is an organic acid residue —$OCOR^2$ wherein $R^2$ is an alkyl group, a cycloalkyl group, an aromatic hydrocarbon group, or an aralkyl group, and n is a number which is one less than the valence of M.

15. The antifouling paint composition as claimed in claim 5, wherein the copolymer (B) for a self-polishing antifouling paint is a copolymer derived from a (meth)acrylic acid metal compound containing no hydroxyl group bonded to a metal atom.

16. The antifouling paint composition as claimed in claim 5, wherein the copolymer (B) for a self-polishing antifouling paint is a copolymer derived from a (meth)acrylic acid zinc salt or copper salt containing no hydroxyl group bonded to a zinc atom or a copper atom.

17. The antifouling paint composition as claimed in claim 5, wherein the copolymer (B) for a self-polishing antifouling paint is a polymerizable unsaturated carboxylic acid metal salt-based copolymer obtained by copolymerizing (a) a (meth)acrylic acid zinc salt or copper salt monomer and (b) another monomer copolymerizable with the monomer (a) and containing constituent units derived from the (meth)acrylic acid zinc salt or copper salt monomer (a) in amounts of 2 to 50% by weight and constituent units derived from the copolymerizable another monomer (b) in amounts of 50 to 98% by weight wherein (a)+(b)=100% by weight.

18. The antifouling paint composition as claimed in claim 5, wherein the copolymer (B) for a self-polishing antifouling paint is a polymerizable unsaturated carboxylic acid silyl ester-based copolymer.

19. The antifouling paint composition as claimed in claim 18, wherein the copolymer (B) for a self-polishing antifouling paint is a copolymer derived from a silyl unsaturated carboxylate monomer and an unsaturated monomer copolymerizable with the silyl unsaturated carboxylate monomer, said silyl unsaturated carboxylate monomer being represented by the following formula [IIIA]:

$$R^1\text{—COO—Si}(L^1L^2L^3) \qquad [IIIA]$$

wherein $R^1$ is an unsaturated bond-containing organic group of $CH_2=C(CH_3)$—, $CH_2=CH$—, $HOOC$—$CH=CH$— or $HOOC$—$CH=C(CH_3)$—, —$COOH$, or a metal salt or an ester thereof, $L^1$, $L^2$ and $L^3$ may be the same or different and are each independently a hydrogen atom, an alkyl group, a cycloalkyl group, an aromatic hydrocarbon group, an aralkyl group or an alkylsilyloxy group.

20. The antifouling paint composition as claimed in claim 19, wherein the copolymer (B) for a self-polishing antifouling paint is a copolymer obtained by copolymerizing silyl (meth) acrylate and an unsaturated monomer copolymerizable with the silyl (meth)acrylate.

21. An antifouling coating film prepared from the antifouling paint composition of claim 5.

22. A ship or an underwater structure coated with a coating film prepared from the antifouling paint composition of claim 5.

23. A fishing tackle or a fishing net coated with a coating film prepared from the antifouling paint composition of claim 5.

24. A method of coating a ship or an underwater structure, comprising coating a surface of a ship or an underwater structure with a coating film comprising the antifouling paint composition of claim 5.

25. A method of coating a fishing tackle or a fishing net, comprising coating a surface of a fishing tackle or a fishing net with a coating film comprising the antifouling paint composition of claim 5.

26. The antifouling paint composition as claimed in claim 7, wherein an organic antifouling agent is contained as the antifouling agent (C).

27. The antifouling paint composition as claimed in claim 20, wherein the copolymer (B) for a self-polishing antifouling paint is a copolymer obtained by copolymerizing silyl (meth) acrylate and an unsaturated monomer copolymerizable with the silyl (meth)acrylate.

28. An antifouling paint composition comprising:
(A) a compounding agent for an antifouling paint comprising one or more substances selected from the group consisting of a cyclic carboxylic acid formed by the addition reaction of an unsaturated carboxylic acid with a conjugated diene compound, a derivative of the cyclic carboxylic acid (except a metal salt), the metal salt of the cyclic carboxylic acid, and the metal salt of a derivative of the cyclic carboxylic acid, wherein the cyclic carboxylic acid is a novel cycloalkenylcarboxylic acid represented by the following formula [V] or a novel bicycloalkenylcarboxylic acid represented by the following formula [VI] or a salt thereof:

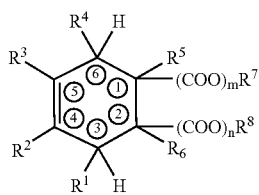

[V]

wherein $R^1$ is a hydrogen atom, a 3-methyl-2-butenyl group or a 2-methyl-1-propenyl group,
when $R^1$ is a hydrogen atom, $R^2$ is a 4-methyl-3-pentenyl group and $R^3$ and $R^4$ are each a hydrogen atom,
when $R^1$ is a 3-methyl-2-butenyl group, $R^2$ is a methyl group and $R^3$ and $R^4$ are each a hydrogen atom,
when $R^1$ is a 2-methyl-1-propenyl group, $R^2$ is a hydrogen atom and $R^3$ and $R^4$ are each a methyl group,
$R^5$ and $R^6$ are each a hydrogen atom or an alkyl group of 1 to 10 carbon atoms,
m and n are each a number of 0 or 1 (with the proviso that it does not occur that m and n are 0 at the same time),
$R^7$ and $R^8$ are each a hydrogen atom or a hydrocarbon group,
when m is 0, $R^7$ is a hydrogen atom,
when m is 1, $R^7$ is a hydrogen atom or a hydrocarbon group,
when n is 0, $R^8$ is a hydrogen atom, and
when n is 1, $R^8$ is a hydrogen atom or a hydrocarbon group, with the proviso that $R^7$ and $R^8$ are not both hydrocarbon groups;

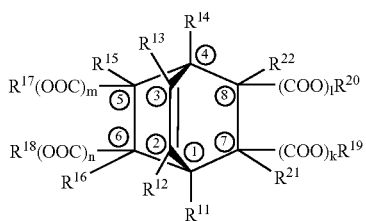

[VI]

wherein any one of $R^{11}$ and $R^{16}$ is an isopropyl group,
[A] in the case where $R^{11}$ is an isopropyl group,
$R^{12}$ and $R^{13}$ are each a hydrogen atom,
$R^{14}$ is a methyl group,
$R^{15}$ and $R^{16}$ are each a hydrogen atom or an alkyl group of 1 to 10 carbon atoms, m and n are each a number of 0 or 1 (with the proviso that it does not occur that m and n are 0 at the same time),
$R^{17}$ and $R^{18}$ are each a hydrogen atom or a hydrocarbon group,
k and l are each 0,
$R^{19}$ and $R^{20}$ are each a hydrogen atom,
$R^{21}$ and $R^{22}$ are each a hydrogen atom or an alkyl group of 1 to 10 carbon atoms,
when m is 0, $R^{17}$ is a hydrogen atom,
when m is 1, $R^{17}$ is a hydrogen atom or a hydrocarbon group,
when n is 0, $R^{18}$ is a hydrogen atom, and
when n is 1, $R^{18}$ is a hydrogen atom or a hydrocarbon group, with the proviso that $R^{17}$ and $R^{18}$ are not both hydrocarbon groups, and
[B] in the case where $R^{16}$ is an isopropyl group,
$R^{11}$ and $R^{12}$ are each a hydrogen atom,
$R^{13}$ is a methyl group,
$R^{14}$ is a hydrogen atom,
$R^{15}$ is a hydrogen atom or an alkyl group of 1 to 10 carbon atoms,
m and n are each 0,
$R^{17}$ and $R^{18}$ are each a hydrogen atom,
k and l are each a number of 0 or 1 (with the proviso that it does not occur that k and l are 0 at the same time),
$R^{19}$ and $R^{20}$ are each a hydrogen atom or a hydrocarbon group,
$R^{21}$ and $R^{22}$ are each a hydrogen atom or an alkyl group of 1 to 10 carbon atoms,
when k is 0, $R^{19}$ is a hydrogen atom,
when k is 1, $R^{19}$ is a hydrogen atom or a hydrocarbon group,
when l is 0, $R^{20}$ is a hydrogen atom, and
when l is 1, $R^{20}$ is a hydrogen atom or a hydrocarbon group, with the proviso that $R^{19}$ and $R^{20}$ are not both hydrocarbon groups, and
(B) a copolymer for a self-polishing antifouling paint.

29. The antifouling paint composition as claimed in claim 28, further comprising (C) an antifouling agent.

30. The antifouling paint composition as claimed in claim 29, wherein copper or a copper compound is contained as the antifouling agent (C).

31. The antifouling paint composition as claimed in claim 29, wherein an organic antifouling agent is contained as the antifouling agent (C).

32. The antifouling paint composition as claimed in claim 28, wherein the copolymer (B) for a self-polishing antifouling paint is a polymerizable unsaturated carboxylic acid hydroxy metal salt-based copolymer.

33. The antifouling paint composition as claimed in claim 28, wherein the copolymer (B) for a self-polishing antifouling paint is a copolymer derived from a polymerizable unsaturated carboxylic acid hydroxy metal compound represented by the following formula [I]:

$$R^1\text{—COO—M—OH} \quad [I]$$

wherein $R^1$ is an unsaturated bond-containing organic group of $CH_2=C(CH_3)-$, $CH_2=CH-$, $HOOC-CH=CH-$ or $HOOC-CH=C(CH_3)-$, $-COOH$, or a metal salt or an ester thereof, and M is a metal atom.

34. The antifouling paint composition as claimed in claim 28, wherein the copolymer (B) for a self-polishing antifouling paint is a copolymer derived from a (meth)acrylic acid hydroxy metal salt.

35. The antifouling paint composition as claimed in claim 28, wherein the copolymer (B) for a self-polishing antifouling paint is a copolymer derived from a (meth)acrylic acid hydroxy zinc salt or copper salt.

36. The antifouling paint composition as claimed in claim 28, wherein the copolymer (B) for a self-polishing antifouling paint is a polymerizable unsaturated carboxylic acid metal compound-based copolymer derived from a polymerizable unsaturated carboxylic acid metal compound containing no hydroxyl group bonded to a metal atom.

37. The antifouling paint composition as claimed in claim 28, wherein the copolymer (B) for a self-polishing antifouling paint is a copolymer derived from a polymerizable unsaturated carboxylic acid metal compound represented by the following formula [II]:

$$R^1\text{—COO—M—}L_n \qquad [II]$$

wherein $R^1$ is an unsaturated bond-containing organic group of $CH_2\!=\!C(CH_3)\text{—}$, $CH_2\!=\!CH\text{—}$, $HOOC\text{—}CH\!=\!CH\text{—}$ or $HOOC\text{—}CH\!=\!C(CH_3)\text{—}$, —COOH, or a metal salt or an ester thereof, M is a metal atom, L is an organic acid residue —$OCR^2$ wherein $R^2$ is an alkyl group, a cycloalkyl group, an aromatic hydrocarbon group, or an aralkyl group, and n is a number which is one less than the valence of M.

38. The antifouling paint composition as claimed in claim 28, wherein the copolymer (B) for a self-polishing antifouling paint is a copolymer derived from a (meth)acrylic acid metal compound containing no hydroxyl group bonded to a metal atom.

39. The antifouling paint composition as claimed in claim 28, wherein the copolymer (B) for a self-polishing antifouling paint is a copolymer derived from a (meth)acrylic acid zinc salt or copper salt containing no hydroxyl group bonded to a zinc atom or a copper atom.

40. The antifouling paint composition as claimed in claim 28, wherein the copolymer (B) for a self-polishing antifouling paint is a polymerizable unsaturated carboxylic acid metal salt-based copolymer obtained by copolymerizing (a) a (meth)acrylic acid zinc salt or copper salt monomer and (b) another monomer copolymerizable with the monomer (a) and containing constituent units derived from the (meth)acrylic acid zinc salt or copper salt monomer (a) in amounts of 2 to 50% by weight and constituent units derived from the copolymerizable another monomer (b) in amounts of 50 to 98% by weight wherein (a)+(b)=100% by weight.

41. The antifouling paint composition as claimed in claim 28, wherein the copolymer (B) for a self-polishing antifouling paint is a polymerizable unsaturated carboxylic acid silyl ester-based copolymer.

42. The antifouling paint composition as claimed in claim 41, wherein the copolymer (B) for a self-polishing antifouling paint is a copolymer derived from a silyl unsaturated carboxylate monomer and an unsaturated monomer copolymerizable with the silyl unsaturated carboxylate monomer, said silyl unsaturated carboxylate monomer being represented by the following formula [IIIA]:

$$R^1\text{—COO—Si}(L^1L^2L^3) \qquad [IIIA]$$

wherein $R^1$ is an unsaturated bond-containing organic group of $CH_2\!=\!C(CH_3)\text{—}$, $CH_2\!=\!CH\text{—}$, $HOOC\text{—}CH\!=\!CH\text{—}$ or $HOOC\text{—}CH\!=\!C(CH_3)\text{—}$, —COOH, or a metal salt or an ester thereof, $L^1$, $L^2$ and $L^3$ may be the same or different and are each independently a hydrogen atom, an alkyl group, a cycloalkyl group, an aromatic hydrocarbon group, an aralkyl group or an alkylsilyloxy group.

43. The antifouling paint composition as claimed in claim 42, wherein the copolymer (B) for a self-polishing antifouling paint is a copolymer obtained by copolymerizing silyl (meth)acrylate and an unsaturated monomer copolymerizable with the silyl (meth)acrylate.

44. An antifouling coating film prepared from the antifouling paint composition of claim 28.

45. A ship or an underwater structure coated with a coating film prepared from the antifouling paint composition of claim 28.

46. A fishing tackle or a fishing net coated with a coating film prepared from the antifouling paint composition of claim 28.

47. A method of coating a ship or an underwater structure, comprising coating a surface of a ship or an underwater structure with a coating film comprising the antifouling paint composition of claim 28.

48. A method of coating a fishing tackle or a fishing net, comprising coating a surface of a fishing tackle or a fishing net with a coating film comprising the antifouling paint composition of claim 28.

49. The antifouling paint composition as claimed in claim 30, wherein an organic antifouling agent is contained as the antifouling agent (C).

50. The antifouling paint composition as claimed in claim 43, wherein the copolymer (B) for a self-polishing antifouling paint is a copolymer obtained by copolymerizing silyl (meth)acrylate and an unsaturated monomer copolymerizable with the silyl (meth)acrylate.

* * * * *